US012708670B2

(12) United States Patent
Roberts et al.

(10) Patent No.: US 12,708,670 B2
(45) Date of Patent: Aug. 18, 2026

(54) METHODS OF MAKING TARGETED VESICLES, AND COMPOSITIONS MADE THEREBY

(71) Applicant: University of Georgia Research Foundation, Inc., Athens, GA (US)

(72) Inventors: Arthur Roberts, Athens, GA (US); Mandi Murph, Athens, GA (US); Sudeepti Kuppa, Athens, GA (US); Pragati Jain, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1253 days.

(21) Appl. No.: 17/486,381

(22) Filed: Sep. 27, 2021

(65) Prior Publication Data

US 2022/0088215 A1 Mar. 24, 2022

Related U.S. Application Data

(63) Continuation-in-part of application No. PCT/US2020/025333, filed on Mar. 27, 2020.

(60) Provisional application No. 62/824,901, filed on Mar. 27, 2019.

(51) Int. Cl.

*G01N 31/00* (2006.01)
*A61K 47/69* (2017.01)
*C12N 15/113* (2010.01)
*G01N 33/53* (2006.01)

(52) U.S. Cl.

CPC ...... *A61K 47/6901* (2017.08); *A61K 47/6913* (2017.08); *C12N 15/113* (2013.01); *C12N 2310/141* (2013.01); *C12N 2320/32* (2013.01)

(58) Field of Classification Search

None

See application file for complete search history.

(56) References Cited

U.S. PATENT DOCUMENTS 5,034,506 A 7/1991 Summerton
5,356,802 A 10/1994 Chandrasegaran
5,539,082 A 7/1996 Nielsen
5,683,886 A 11/1997 van der Bruggen
5,698,685 A 12/1997 Summerton
6,140,081 A 10/2000 Barbas
6,677,157 B1 1/2004 Cohen
6,699,475 B1 3/2004 Panicali
2002/0025313 A1 2/2002 Micklus
2003/0018169 A1 1/2003 Kochendoerfer
2007/0154989 A1 7/2007 Barbas
2009/0220587 A1 9/2009 Allon
2010/0272636 A1 10/2010 Byrd et al.
2011/0145940 A1 6/2011 Voytas
2014/0356382 A1 12/2014 Wood
2015/0346198 A1 12/2015 Naumann
2017/0313685 A1 11/2017 St. John
2018/0000950 A1 1/2018 Savel
2018/0009909 A1 1/2018 Yu
2018/0177727 A1 6/2018 Kalluri

FOREIGN PATENT DOCUMENTS

WO 2003016496 2/2003
WO 2011072246 6/2011

OTHER PUBLICATIONS

Mcgregor et al. Nature Biotechnology, vol. 21, No. 2, Feb. 2003, pp. 171-176.*

Akao, et al., “Role of anti-oncomirs miR-143 and -145 in human colorectal tumors”, Cancer Gene Ther., 17:398-408 (2010).

Baker, et al., Low, Membrane Separation, in: Reference Module in Chemistry, Molecular Sciences and Chemical Engineering, Elsevier, (2015).

Baroni, et al., “Exosome-mediated delivery of miR-9 induces cancer-associated fibroblast-like properties in human breast fibroblasts”, Cell Death Dis., 7(7):e2312 (2016).

Bartel, “MicroRNAs: Genomics, Biogenesis, Mechanism, and Function”, Cell, 116(2):281-97 (2004).

Bryniarski, et al., “Antigen-specific, antibody-coated, exosome-like nanovesicles deliver suppressor T-cell microRNA-150 to effector T cells to inhibit contact sensitivity”, Journal of Allergy and Clinical Immunology, 132(1):170- 181 (2013).

Bulboacă, et al., “Comparative Effect of Curcumin Versus Liposomal Curcumin on Systemic Pro-Inflammatory Cytokines Profile, MCP-1 and RANTES in Experimental Diabetes Mellitus”, Int. J. Nanomedicine, 14: 8961-8972 (2019).

Cahall, et al., “A Quantitative Perspective on Surface Marker Selection for the Isolation of Functional Tumor Cells”, Breast Cancer (Auckl), 9(Suppl 1):1-11 (2015).

Carvalho, et al., “Application of Light Scattering Techniques to Nanoparticle Characterization and Development”, Frontiers in Chemistry, 6:237 (2018). doi.org/10.3389/fchem.2018.00237.

Charoenviriyakul, et al., “Preservation of exosomes at room temperature using lyophilization”, International Journal of Pharmaceutics, 553(1-2):1-7 (2018).

Chen, et al., “Nanoparticles Modified With Tumor-targeting scFv Deliver siRNA and miRNA for Cancer Therapy”, Molecular Therapy, 18(9):1650-1656 (2010).

Cui, et al., “Liposomal Delivery of MicroRNA-7 Targeting EGFR to Inhibit the Growth, Invasion, and Migration of Ovarian Cancer”, ACS Omega, 6(17):11669-11678 (2021).

D’Souza, et al., “Asialoglycoprotein receptor mediated hepatocyte targeting—Strategies and applications”, Journal of Controlled Release, 203:126-139 (2015).

(Continued)

*Primary Examiner* — Lisa V Cook
(74) *Attorney, Agent, or Firm* — Pabst Patent Group LLP

(57) ABSTRACT

Functionalized lipid vesicles having a lipid membrane and a functional element, and methods of making them are provided. The methods of making the vesicles typically include mixing lipid vesicles formed of one or more lipids with one or more lipid conjugates and dialyzing the mixture for an effective amount of time and under conditions suitable for the lipid conjugate to insert into the membrane of lipid vesicles and form functionalized lipid vesicles that include the lipid conjugate as a functional element.

20 Claims, 17 Drawing Sheets

Specification includes a Sequence Listing.

(56) References Cited

OTHER PUBLICATIONS

Dai, et al., “miR-21 is involved in transforming growth factor β1-induced chemoresistance and invasion by targeting PTEN in breast cancer”, Oncol. Lett., 14(6):6929-36 (2017).
Das, et al., “Exosome as a Novel Shuttle for Delivery of Therapeutics across Biological Barriers”, Mol. Pharm., 16(1): 24-40 (2018).
Di, et al., “Exosomes as drug carriers for clinical application”, Artif. Cells Nanomed. Biotechnol., 46(Sup3): S564-S570 (2018).
Donato, et al., “Culture and Functional Characterization of Human Hepatoma HepG2 Cells”, Methods Mol. Biol., 1250: 77-93 (2015).
Doyle, et al., “Overview of Extracellular Vesicles, Their Origin, Composition, Purpose, and Methods for Exosome Isolation and Analysis”, Cells, 8(7):727 (2019).
Fragni, et al., “The miR-21/PTEN/Akt signaling pathway is involved in the anti-tumoral effects of zoledronic acid in human breast cancer cell lines”, Naunyn Schmiedebergs Arch Pharmacol., 389(5):529-38 (2016).
Ge, et al., “miRNA in Plasma Exosome is Stable under Different Storage Conditions”, Molecules, 19:1568-1575 (2014).
Gembardt, et al., “Organ-specific distribution of ACE2 mRNA and correlating peptidase activity in rodents”, Peptides, 26(7):1270-1277 (2005).
Guo, et al., “Liposomal Nanoparticles Carrying anti-IL6R Antibody to the Tumour Microenvironment Inhibit Metastasis in Two Molecular Subtypes of Breast Cancer Mouse Models”, Theranostics, 7(3):775-788 (2017).
Hamming, et al., “Tissue distribution of ACE2 protein, the functional receptor for SARS coronavirus. A first step in understanding SARS pathogenesis”, J. Pathol., 203:631-637 (2004).
Haney, et al., “Genetically modified macrophages accomplish targeted gene delivery to the inflamed brain in transgenic Parkin Q311X(A) mice: importance of administration routes”, Scientific Reports, 10(1):11818 (2020).
Harmer, et al., “Quantitative mRNA expression profiling of ACE 2, a novel homologue of angiotensin converting enzyme”, FEBS Letters, 532 (1-2):107-110 (2002).
Hua, “Orally administered liposomal formulations for colon targeted drug delivery”, Front Pharmacol., 5:138 (2014).
Huang, et al., “Characterization of antibody covalently coupled to liposomes”, Biochimica Et Biophysica ACTA, 176(2):140-140 (1982).
Huang, et al., “Monoclonal antibody covalently coupled with fatty acid. A reagent for in vitro liposome targeting”, Journal of Biological Chemistry, 255(17):8015-8018 (1980).
Iden, et al., “In vitro and in vivo comparison of immunoliposomes made by conventional coupling techniques with those made by a new post-insertion approach”, Biochimica et Biophysica Acta BBA)—Biomembranes, 1513(2): 207-216 (2001).
Iranifar, et al., “Exosomes and microRNAs: New potential therapeutic candidates in Alzheimer disease therapy”, J. Cell Physiol., 234(3):2296-305 (2019).
Jiang, et al., “Aptamer (AS1411)-Conjugated Liposome for Enhanced Therapeutic Efficacy of miRNA-29b in Ovarian Cancer”, Journal of Nanoscience and Nanotechnology, 20(4):2025-2031 (2020).
Kim, et al., “Development of exosome-encapsulated paclitaxel to overcome MDR in cancer cells”, Nanomedicine, 12(3):655-64 (2016).
Kim, et al., “Region and Cell Type Distribution of TCF4 in the Postnatal Mouse Brain”, Frontiers in Neuroanatomy, 14(42):1-19 (2020).
Kodidela, et al., “Cytokine profiling of exosomes derived from the plasma of HIV-infected alcohol drinkers and cigarette smokers”, PLoS One, 13:e0201144 (2018).
Kosuri, et al., “Large-scale de novo DNA synthesis: technologies and applications”, Nature Methods, 11:499-507 (2014).
Kuppa, et al., “Autotaxin exacerbates tumor progression by enhancing MEK1 and overriding the function of miR-489-3p”, Cancer Lett., 432:84-92 (2018).
Ledwitch, et al., “Unravelling the complex drug-drug interactions of the cardiovascular drugs, verapamil and digoxin, with P-glycoprotein”, Biosci. Rep., 36:1-14 (2016).
Liang, et al., “Engineered exosome-mediated delivery of functionally active miR-26a and its enhanced suppression effect in HepG2 cells”, Int. J. Nanomedicine, 13:585-599 (2018).
Liang, et al., “Engineered exosomes for targeted co-delivery of miR-21 inhibitor and chemotherapeutics to reverse drug resistance in colon cancer”, Journal of Nanobiotechnology, 18(1):10 (2020).
Linegar, et al., “Hydrodynamic radius of polyethylene glycol in solution obtained by dynamic light scattering”, Colloid J., 72: 279-281 (2010).
Ling, et al., “A colorimetric method for the molecular weight determination of polyethylene glycol using gold nanoparticles”, Nanoscale Research Letters, 8(1):538 (2013).
Liu, et al., “Design strategies and application progress of therapeutic exosomes”, Theranostics, 9:1015-1028 (2019).
Lobba, et al., “Differential expression of CD90 and CD14 stem cell markers in malignant breast cancer cell lines”, Cytometry A, 81(12):1084-91 (2012).
Lu, et al., “MicroRNA expression profiles classify human cancers”, Nature, 435(7043):834-8 (2005).
Makra, et al., “A method based on light scattering to estimate the concentration of virus particles without the need for virus particle standards”, MethodsX, 2:91-99 (2015).
Matias-Garcia, et al., “Imact of long-term storage and freeze-thawing on eight circulating microRNAs in plasma samples”, PLoS One, 15(1):e0227648 (2020).
Matsuzaki, et al., “Optical characterization of liposomes by right angle light scattering and turbidity measurement”, Biochim Biophys Acta., 1467(1):219-26 (2000).
Mebius, et al., “Structure and function of the spleen”, Nat Rev Immunol., 5:606-616 (2005).
Medina, et al., “Pharmacokinetics and biodistribution of [111In]-avidin and [99mTc]-biotin-liposomes injected in the pleural space for the targeting of mediastinal nodes”, Nuclear Medicine and Biology, 31:41-51 (2004).
Meyer, et al., “Pseudotyping exosomes for enhanced protein delivery in mammalian cells”, IJN, 12:3153-3170 (2017).
Mui, et al., “Extrusion technique to generate liposomes of defined size”, Methods in Enzymology, 367:3-14 (2003).
Nie, et al., “Use of lung-specific exosomes for miRNA-126 delivery in non-small cell lung cancer”, Nanoscale, 12(2):877-887 (2020).
Nobbman, et al., “Dynamic light scattering as a relative tool for assessing the molecular integrity and stability of monoclonal antibodies”, Biotechnology and Genetic Engineering Reviews, 24(1):117-128 (2007).
Pan, et al., “Hepatic cell-to-cell transmission of small silencing RNA can extend the therapeutic reach of RNA interference (RNAi)”, Gut, 61(9):1330-1339 (2012).
Panda, et al., “Isolation of human PBMCs”, Bio-Protocol, 3:e323 (2013).
Perrakis, et al., “Autotaxin: structure-function and signaling”, J. Lipid Res., 55:1010-1018 (2014).
Reth, “Matching cellular dimensions with molecular sizes”, Nat. Immunol., 14 :765-767 (2013).
Rigaud, et al., “Reconstitution of membrane proteins into liposomes”, Methods in Enzymology, 372:65-86 (2003).
Robinson, et al., “Post-transitional membrande insertion of an endogenous YidC substrate”, Biochimica Et Biophysica ACTA, 1833(12):2781-2788 (2013).
Rupaimoole, et al., “MicroRNA therapeutics: towards a new era for the management of cancer and other diseases”, Nat. Rev. Drug Discov., 16(3):203-22 (2017).
Schwarz, et al., “Podocin, a raft-associated component of the glomerular slit diaphragm, interacts with CD2AP and nephrin”, J. Clin. Invest., 108:1621-1629 (2001).
Senbanjo, et al., “CD44: A Multifunctional Cell Surface Adhesion Receptor Is a Regulator of Progression and Metastasis of Cancer Cells”, Front Cell Dev. Biol., 5(18):1-6 (2017).
Si, et al., “Targeted Exosomes for Drug Delivery: Biomanufacturing, Surface Tagging, and Validation”, Biotechnology Journal, 15:1900163 (2020).

(56) References Cited

OTHER PUBLICATIONS

Sil, et al., "Macrophage-derived IL-1β enhances monosodium urate crystal-triggered NET formation", Inflamm. Res., 66(3):227-37 (2017).
Stetefeld, et al., "Dynamic light scattering: a practical guide and applications in biomedical sciences", Biophys. Rev., 8(4):409-427 (2016).
Stevens, et al., "Formulation kit for liposomal doxorubicin composed of lyophilized liposomes", Anticancer Res., 23:439-442 (2003).
Torchilin, et al., "Multifunctional nanocarriers", Advanced Drug Delivery Reviews, 58(14):1532-55 (2006).
Van Der Ree, et al., "Miravirsen dosing in chronic hepatitis C patients results in decreased microRNA-122 levels without affecting other microRNAs in plasma", Aliment Pharmacol Ther., 43(1):102-13 (2016).
Walsh, et al., "Microfluidic-based manufacture of siRNA-lipid nanoparticles for therapeutic applications", Methods Mol Biol., 1141:109-120 (2014).
Witzigmann, et al., "Variable asialoglycoprotein receptor 1 expression in liver disease: Implications for therapeutic intervention", Hepatology Research, 46: 686-696 (2016).
Wu, et al., "MicroRNA-21 (Mir-21) Promotes Cell Growth and Invasion by Repressing Tumor Suppressor PTEN in Colorectal Cancer", Cell Physiol Biochem., 43(3):945- 58 (2018).
Wu, et al., "Therapeutic Delivery of MicroRNA-29b by Cationic Lipoplexes for Lung Cancer", Molecular Therapy—Nucleic Acids, 2:e84 (2013).
Ximbio, et al., "What is a polyclonal antibody?"—Ximbio FAQ, (n.d.), retreived online, <ximbio.com/faq/57/what-is-a-polyclonal-antibody> (accessed Jul. 30, 2021).
International Search Report received for PCT Patent Application No. PCT/US2020/025333, mailed on Jun. 15, 2020, 4 pages.

* cited by examiner

*
**
3
2
1
0
[Target] Normalized
miR-21-5p
PTEN
Abi-exosomes alone
miR-21-5p

R
Soluble protein
receptor
R
EXTRACELLULAR
STEP 1
INTRACELLULAR
STEP 2
STEP 3
R
R
R
Soluble
protein
STEP 4
Golgi
Apparatus Relative wound area 1.2

1.0

0.8

0.6

0 24 48 72

Time (Hours)

```
SEQUENCE LISTING

<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: synthetic polynucleotide

<400> SEQUENCE: 1

gugacaucac auauacggca gc                                               22


<210> SEQ ID NO 2
<211> LENGTH: 22
<212> TYPE: RNA
<213> ORGANISM: Artificial Sequence
<220> FEATURE:
<223> OTHER INFORMATION: synthetic polynucleotide

<400> SEQUENCE: 2

uagcuuauca gacugauguu ga                                               22


<210> SEQ ID NO 3
<211> LENGTH: 23
<212> TYPE: RNA
<213> ORGANISM: Artificial Sequence
<220> FEATURE:
<223> OTHER INFORMATION: synthetic polynucleotide

<400> SEQUENCE: 3

ggcagaggag ggcuguucuu ccc                                              23


<210> SEQ ID NO 4
<211> LENGTH: 24
<212> TYPE: RNA
<213> ORGANISM: Artificial Sequence
<220> FEATURE:
<223> OTHER INFORMATION: synthetic polynucleotide
```

```
<400> SEQUENCE: 4

agcagaagca gggagguucu ccca                                          24


<210> SEQ ID NO 5
<211> LENGTH: 22
<212> TYPE: RNA
<213> ORGANISM: Artificial Sequence
<220> FEATURE:
<223> OTHER INFORMATION: synthetic polynucleotide

<400> SEQUENCE: 5

caguuaucac agugcugaug cu                                            22
```

****

METHODS OF MAKING TARGETED VESICLES, AND COMPOSITIONS MADE THEREBY

CROSS-REFERENCE TO RELATED APPLICATION

This application is a continuation-in-part of PCT/US2020/025333 filed Mar. 27, 2020, which claims the benefit of and priority to U.S. Provisional Application No. 62/824,901 filed Mar. 27, 2019, each of which is hereby incorporated by reference in its entirety.

STATEMENT REGARDING FEDERALLY SPONSORED RESEARCH

This invention was made with government support under Grant No. 1R01CA204846-01A1 awarded by the National Institutes of Health. The government has certain rights in the invention.

REFERENCE TO SEQUENCE LISTING

The Sequence Listing submitted as a text file named "UGA_2019_147_PCT_ST25.txt," created on Mar. 27, 2020, and having a size of 1,349 bytes is hereby incorporated by reference pursuant to 37 C.F.R § 1.52(e)(5).

FIELD OF THE INVENTION

This application is generally in the field of drug delivery, and more specifically methods of making and using lipid-based delivery vesicles for delivery of cargo including nucleic acids such as miRNA.

BACKGROUND OF THE INVENTION

Since their discovery in 1983 by two distinct research groups (Pan & Johnstone, *Cell.* 33(3):967-78 (1983), Harding & Heuser, *J Cell Biol.* 97(2):329-39 (1983)), exosomes have been well characterized in diverse areas of research. Several recent studies have outlined their significance as key regulators of cell-to-cell communication, biomarker vehicles in conditions such as Alzheimer's disease and cancer (Iranifar et al., *J Cell Physiol.* 234(3):2296-305 (2019) doi: 10.1002/jcp.27214, Mitchell et al., *Proc Natl Acad Sci USA.* 105(30):10513-8 (2008)), or as carriers for therapeutics (Di et al., *Artif Cells Nanomed Biotechnol.* 46(Sup3): S564-S570 (2018) doi: 10.1073/pnas.0804549105). While exosomes require purification before being utilized as carriers, they can hold diverse cargo such as microRNA (miRNA), protein and mRNA, and widely access all cell types through circulation, including crossing the blood-brain barrier (Das et al., *Mol Pharm.* 16(1): 24-40 (2018) doi: 10.1021/acs.molpharmaceut.8b00901). Exosomes are increasingly being utilized as efficient drug carriers, for example paclitaxel loaded into exosomes showed increased accumulation in both drug-sensitive and -resistant lung cancer cells (Kim et al., *Nanomedicine.* 12(3):655-64 (2016) doi:10.2217/nnm-2016-0237), and exosomally delivered miR-9 in breast cancer fibroblasts and miR-122 served as a chemo-sensitizer in hepatocellular carcinoma (Baroni et al., *Cell Death Dis.* 7(7):e2312 (2016) doi: 10.1038/cddis.2016.224, Lou et al., *J Hematol Oncol.* 8:122 (2015) doi: 10.1186/s13045-015-0220-7).

miRNAs, small 20-22 nucleotide RNAs, have also been at the forefront of therapeutics research, especially in cancer, due to their ability to effectively inhibit gene expression in cancer cells by binding mRNA and inhibiting protein translation (Bartel, *Cell.* 116(2):281-97 (2004) doi: 10.1016/50092-8674(04)00045-5). For example, miR-26a-containing exosomes delivered to hepatocellular carcinoma cells were shown to significantly slow cell migration and proliferation due to increased miRNA levels (Liang et al., *Int J Nanomedicine.* 13:585-99 (2018) doi: 10.2147/IJN.S154458). miRNAs have also been considered as key candidates for circulating biomarkers indicative of disease state and, in some cases, tumor staging and progression (Lu et al., *Nature* 435(7043):834-8 (2005) doi: 10.1038/nature03702, Calin & Croce, *Nat Rev Cancer* 6(11):857-66 (2006) doi:10.1038/nrc1997). For example, a recent study revealed the significance of miR-489-3p in ovarian cancer development and its ability to target and repress MEKI, a prominent oncogene relevant in several malignancies (Kuppa et al., *Cancer Lett.* 432:84-92 (2018) doi: 10.1016/j.canlet.2018.05.037). miR-34 has also been well classified as a tumor suppressor in several cancers in the past, and reached phase 1 clinical trials in 2017 (Rupaimoole & Slack, *Nat Rev Drug Discov.* 16(3):203-22 (2017) doi: 10.1038/nrd.2016.246, Agostini & Knight, *Oncotarget.* 5(4):872-81 (2014) DOI: 10.18632/oncotarget.1825). Miraversin, which is an anti-sense miRNA inhibitor that targets overexpression of miR-122, reached phase 2 clinical trials for Hepatitis C virus infections (van der Ree et al., *Aliment Pharmacol Ther.* 43(1):102-13 (2016) doi: 10.1111/apt.13432).

Methods for engineering the surfaces of extracellular vesicles are discussed in Antes, et al., *Journal of Nanobiotechnology,* 16:61 (2018), doi.org/10.1186/s12951-018-0388-4. However, there remains a need for improved lipid-based delivery vesicles and methods for making them, particularly for use in the delivery of nucleic acid cargo such as miRNAs. For example, a significant barrier for implementing exosomes as a therapeutic vehicle of microRNAs in the clinic is their propensity to cause off-target effects due to their versatile target range and the difficulties of bioengineering them without disrupting them, which ultimately affects their endocytotic efficiency.

Thus, it is an object of the invention to provide methods of making versatile and customizable lipid-based delivery vehicles that are effective at specifically targeting cells and delivering cargo, including nucleic acids, with improved efficiency, and the lipid vehicles formed therefrom.

SUMMARY OF THE INVENTION

Functionalized lipid vesicles having a lipid membrane and a functional element, and methods of making them are provided. The methods of making the vesicles typically include mixing lipid vesicles formed of one or more lipids with one or more lipid conjugates and dialyzing the mixture for an effective amount (i.e., sufficient amount) of time and under conditions suitable for the lipid conjugate to insert into the membrane of lipid vesicles and form functionalized lipid vesicles that include the lipid conjugate as a functional element. The lipid conjugates typically include a lipid component conjugated or otherwise linked to a functional element.

For example, a method of making functionalized lipid vesicles can include mixing, in the presence of detergent, lipid vesicles including one or more lipids with one or more types of lipid conjugates and dialyzing the mixture for an effective amount (i.e., sufficient amount) of time for the lipid conjugate(s) to insert into the lipid vesicles and form functionalized lipid vesicles. Typically the dialysis removes the remaining detergent.

Some of the methods further include preparing the lipid conjugate. The methods can include one or more, preferably all, of the following steps:

(i) mixing or otherwise suspending the lipid component, or a precursor thereof, in a solution including a concentration of detergent near the critical micelle concentration to form a suspension, (ii) dialyzing the suspension to remove excess detergent, and encourage formation of stable micelles in the suspension, (iii) adding, mixing, or otherwise contacting the suspension with the functional element under conditions suitable for the functional element to conjugate, or otherwise link, to the lipid component to form the lipid conjugate. Step (ii) can be before or after step (iii). In some embodiments, a method of making a lipid conjugate proceeds in the order of step (i), (ii), and (iii).

The first dialysis may remove excess detergent, but leave an effective amount suitable for stabilizing the hydrophobic regions of the lipid component, or precursor thereof, in a semi-aqueous solution. The detergent, which can be selected by the practitioner, should be one suitable for doing so. An exemplary detergent is n-dodecyl-β-D-maltoside (DDM), optionally at a concentration of about 0.1%.

When the lipid conjugate and vehicle are mixed to form functionalized lipid vehicles, dialysis of the mixture (which can also be a second dialysis following the first dialysis during preparation of the lipid conjugant) removes the remaining detergent, and facilitates formation of functionalized lipid vesicle product.

The initial lipid vesicle can be naturally occurring, for example, isolated or otherwise collected from cultured or uncultured tissue, cells, or fluid. In some embodiments, the fluid is one derived from or conditioned by cultured cells, or is blood, plasma, lymph liquid, malignant pleural effusion, amniotic liquid, breast milk, semen, saliva or urine. In some embodiments, the cells are peripheral blood mononuclear cells. The lipid vesicles can be, for example, apoptotic bodies and/or blebs (AB), microvesicles (MV), exosomes, or tunneling nanotubes (TNT).

In some embodiments, the lipid vesicles are synthetic. Synthetic vesicles include, for example, niosomes and liposomes.

In some embodiments, the lipid vesicles are exosomes or exosome mimics, preferably between about 30-150 nm.

The lipid conjugate typically includes a functional element conjugated to or otherwise linked, directly or indirectly, to a lipid (also referred to as the lipid component of the conjugate). The functional element can be a small molecule, protein or polypeptide, carbohydrate, nucleic acid or a combination thereof. In preferred embodiments, at least one of the functional elements is a targeting moiety that increases attachment, binding, or association of the functionalized lipid vesicle to a target cell(s), tissues(s), and/or microenvironment(s) relative to the lipid vesicle. Additionally or alternatively the targeting moiety can increase attachment, binding, or association of the functionalized lipid vesicle to a target cell(s), tissues(s), and/or microenvironment(s) relative non-targeted cell(s), tissue(s), and/or microenvironment(s).

In some embodiments, the targeting moiety targets cancer cells. In more specific embodiments, the targeting moiety targets CD44 or CD29/Integrin beta-1.

In some embodiments, the targeting moiety targets hepatocytes. In more specific embodiments, the targeting moiety targets asialoglycoprotein receptor 1/HL-1 (ASGR1).

In some embodiments, the functional element is an antibody. Thus, in some embodiments, the targeting moiety is an antibody that binds to CD44 or CD29/Integrin beta-1 or I-CAM. In other embodiments, the targeting moiety is antibody that binds to asialoglycoprotein receptor 1/HL-1 (e.g., Anti-ASGR1 antibody).

In other embodiments, the functional element is a detectable label such as a fluorophore, radiolabel, magnetic label, or a contrast agent.

The methods of making the functionalized lipid vesicles can include loading the lipid vesicles or functionalized lipid vesicles with an active agent. The loading of the vesicles typically includes mixing vesicles and active agent alone or in combination with incubation, freeze-thaw cycling, sonication, extrusion, chemical transfection, electroporation, or a combination thereof.

The active agent can be, for example, a therapeutic, nutritional, diagnostic, prophylactic compound, or a combination thereof. The active agent can also include or be a protein, peptide, carbohydrate, polysaccharide, nucleic acid molecule, and/or organic small molecule.

In some embodiments, the active agent is one or more nucleic acid molecules selected from antisense, siRNA, miRNA, anti-miRNA, primary transcript miRNA (pri-miRNA), aptamers, ribozymes, external guide sequences for ribonuclease P, triplex forming agents, and CRIPSR/Cas component(s), or a polynucleotide encoding any of the foregoing. The miRNA can be a pri-miRNA, precursor miRNA (pre-miRNA), mature miRNA, miRNA mimic, or a fragment or variant thereof that retains the biological activity of the miRNA. In some embodiments, the nucleic acid such as miRNA, targets an oncogene.

In a particular embodiment, the active agent is a nucleic acid such as an miRNA loaded by a method that includes electroporation.

Functionalized lipid vesicles made according to the disclosed methods, and pharmaceutical compositions formed therefrom, are also provided, as are methods of using the functionalized lipid vesicles and pharmaceutical compositions. For example, the functionalized lipid vesicles can be used to deliver active agent(s) to cells in vitro and in vivo. In preferred in vivo methods, the active agent-loaded functionalized lipid vesicles are administered to a subject in need thereof in an effective amount to treat a disease or disorder. Diseases and disorders include, but are not limited to, cancer, infectious diseases, autoimmune diseases, genetic diseases, etc.

BRIEF DESCRIPTION OF THE DRAWINGS

FIG. 2A illustrates that attachment of the antibody-label to exosomes causes a size peak shift to the right, indicating a larger particle size compared to exosomes without the antibody-label, confirming the attachment. FIG. 2B provides additional details, comparing the average particle sizes of exosomes (-Δ-), Abi-exosomes (exosomes labeled with antibodies) (-□-), a mixture of 100 μM 1,2-distearoyl-sn-glycero-3-phosphoethanolamine-N-[maleimide (polyethylene glycol)-2000](DSPE-PEG 2000) (fatty acid with DDM and 100 μM (NBD-DSPE) solubilized in 0.1% w/v of the detergent N-dodecyl-β-D-maltoside (DDM) at the critical micelle concentration (CMC) (Fatty Acids, -○-), and 0.1% w/v DDM (-◆-). The Malvern Zetasizer Nano ZS DLS instrument (Malvern Pananalytical Ltd., United Kingdom) with a 105.251-QS ultra-micro fluorescence quartz cuvette (Hellma USA, Plainview, NY) was used to perform the DLS experiments to determine sizes and distributions of the particles. The DLS chromatograms were analyzed with Zetasizer 7.03 software using standard refractive indices for a protein in aqueous solution.

FIG. 7A shows the formation of functionalized lipids (Step 1) by adding more detergent in a mix of lipids and detergent micelles followed by addition of more lipids to form modified liposomal nano particles by dialyzing over a period of 45 hours (Step 2). Downstream purification to remove unincorporated lipids and detergent by column chromatography (Step 3). FIG. 7B shows lysis of natural vesicles/extracellular vesicles (Step 1) followed by addition of functionalized lipids to lysed fragments (Step 2) and dialysis for more than 45 hours (Step 3). Modified extracellular vesicles are then purified using column chromatography (Step 4). FIG. 7C shows reactive lipids and detergent micelles are dialyzed for two hours in Step 1 followed by incubation of reactive lipids with antibodies for 1 hour in Step 2 to form functionalized lipids. The functionalized lipids are then incubated (Step 3) with pre-formed liposomal nano particles for 1 hour followed by dialysis (Step 4) for 2 hours to obtain modified lipid nanoparticles. FIG. 7D shows formation of reactive lipids (Step 1) followed by antibody incubation (Step 2), which are then incubated (Step 3) with pre-formed extracellular vesicles for 1 hour followed by 2-hour dialysis (Step 4) to bioengineer modified extracellular vesicles.

FIG. 10A is a bar graph showing the percent wound closure exhibited by the cells treated with empty EVs (light grey column, $2^{nd}$), EVs containing miRNA (light grey column, $3^{rd}$), empty mEVs (dark grey column, $4^{th}$), mEVs containing miRNA (dark grey column, $5^{th}$) and mLNPs containing miRNA (clear column, $6^{th}$) when normalized to that by untreated cells (black column, $1^{st}$). FIG. 10B is a line graph showing cell migration of untreated cells (bottom line, circles) and cells treated with, EVs (miRNA) (hexagons), mEVs (miRNA) (diamonds), and mLNPs (miRNA) (triangles) quantitatively measured over 72 hours. The error bars represent the mean of three independent experiments ±SD (****p<0.0001 for the last points). Dose of miRNA: 0.35 μg.

FIG. 15A-15B are bar graphs showing the relative ratio of mmu-miR-298 uptake in various organs of mice after being treated with (15A) modified-extracellular vesicles and (15B) modified lipid nano particles versus serum free media(control) (n=6) in a log scale. The data was normalized to U6 and expressed as mean±SEM (**p<0.0001, *p<0.001, **p<0.01, *p<0.05). FIG. 15C is a dot plot showing the levels of 8-major cytokine factors as obtained after conducting cytokine assay on the blood samples withdrawn from mice treated with modified-exosomes and modified-liposomes versus serum free media(control) (n=6) 72 hours after the treatment. Dose: 110 ug; Injection volume: 250-300 ul.

DETAILED DESCRIPTION OF THE INVENTION

I. Definitions

Figure 1A:
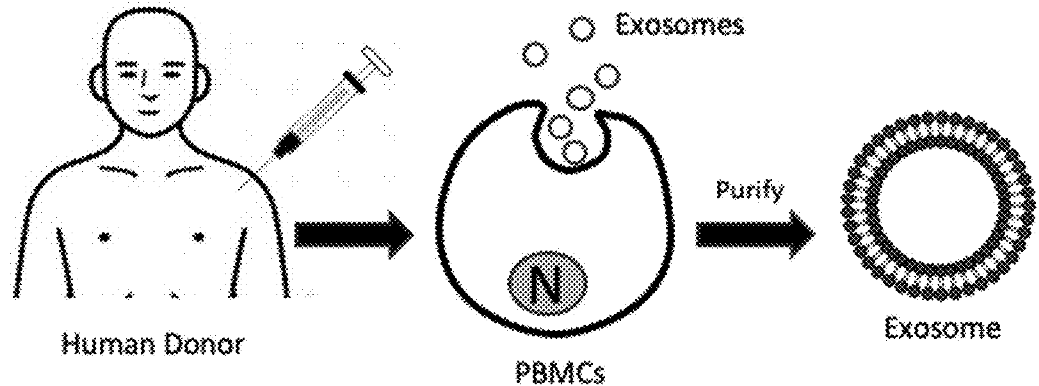
FIG. 1A is a flow diagram illustrating an exemplary method of isolating naturally-occurring exosomes. First, peripheral blood mononuclear cells (PBMCs) are obtained from a human blood donor and cultured (e.g., for 24-48 hours) to allow exosomes to accumulate in the culture medium. Exosomes are then isolated and purified using, e.g., an isolation kit such as the Exiqon Exosome Isolation Kit.

"Active agent" as used herein refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

"Hydrophobic" as used herein refers to a non-polar molecule or part of a molecule that cannot form energetically favorable interactions with water molecules and therefore does not dissolve in water.

"Hydrophilic" as used herein describes a polar molecule or part of a molecule that forms enough energetically favorable interactions with water molecules to dissolve readily in water.

"Amphiphilic" as used herein describes a molecule having both hydrophobic and hydrophilic regions, such as in a phospholipid or a detergent molecule.

"Effective amount" and "suitable amount" as used herein with respect to a therapeutic agent is at least the minimum concentration required to effect a measurable improvement or prevention of any symptom or a particular condition or disorder, to effect a measurable enhancement of life expectancy, or to generally improve patient quality of life. The effective amount may vary depending on such factors as the disease or condition being treated, the active agent(s) (e.g., particular targeted constructs, etc.) being administered, the size of the subject, or the severity of the disease or condition. With regard to cancer, an effective amount can refer to an amount of the active agent that reduces or inhibits tumor growth or tumor burden. The effective amount can be in the context of the delivery systems disclosed herein. For example, in some embodiments, "therapeutically effective amount" refers to an amount of the therapeutic agent that, when incorporated into and/or onto particles described herein, produces some desired effect at a reasonable benefit/risk ratio applicable to any medical treatment. One of ordinary skill in the art may empirically determine the effective amount of a particular compound without necessitating undue experimentation.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Antibody" as used herein refers to natural or synthetic antibodies that bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that bind the target antigen.

"Single chain Fv" and "scFv" as used herein means a single chain variable fragment that includes a light chain variable region (VL) and a heavy chain variable region (VH) in a single polypeptide chain joined by a linker which enables the scFv to form the desired structure for antigen binding (i.e., for the VH and VL of the single polypeptide chain to associate with one another to form a Fv). The VL and VH regions may be derived from the parent antibody or may be chemically or recombinantly synthesized.

"Individual," "host," "subject," and "patient" as used herein are used interchangeably to refer to any individual who is the target of administration or treatment. The subject can be a vertebrate, for example, a mammal. The subject can be a human or veterinary patient.

"Treatment" as used herein refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

II. Lipid-Based Delivery Vehicles

To make the targeting of exosomes and other lipid vesicles more specific, customizable functionalized lipid-based vesicles including, but not limited to, antibody-labeled exosomes, that can be used as vehicles to deliver cargo such as nucleic acids to cells are provided. Exosome vesicles functionalized with an antibody (i.e., antibody-labeled exosomes) can also be referred to as "Abi-exosomes."

Preferred methods of making the functionalized vesicles are also provided.

The experiments below illustrate an exemplary method where the vesicles (e.g., exosomes) are bioengineered as a tool for delivery of cargo such as miRNA using a targetable molecular cell surface marker to increase cargo uptake. The exosomes can be purified from a variety of cell types including, but not limited to, mesenchymal stem cells (MSCs), or peripheral blood mononuclear cells (PBMCs) from a group of blood donors, or made synthetically. For example, in the experiments below, exosomes were functionalized without disrupting their structural integrity or interfering with their endocytic machinery. A functional element, exemplified with an antibody, was attached to a long polyethylene glycol (PEG) chain and a fatty acid (FA) and the antibody-PEG-FA complex was passively inserted into exosomes by dialysis.

Upon removal of the stabilizing n-dodecyl-β-D-maltoside (DDM) detergent, the tail of the pegylated fatty acid conjugate formed a covalent linkage to the antibody, which was inserted into the exosomal membrane to maintain its hydrophobicity. The addition of an antibody attachment drove the functionalized exosomes, initially purified from peripheral blood mononuclear cells obtained from a human blood donor and loaded with miRNA cargo (e.g., MiR-21-5p, which inhibits expression of the phosphatase and tensin homolog (PTEN) gene and has been implicated in many cancers), to target specific cell surface proteins corresponding to the antibody, thereby increasing exosomal uptake.

To monitor the insertion process, a fluorescently-labeled FA can be added with the antibody-PEG-FA complex, which quenches upon insertion into the exosome.

Through electroporation, the miR-21-5p cargo was internalized into the Abi-exosome without disrupting its structure. Subsequently, cells treated with Abi-exosomes containing miR-21-5p and antibodies targeting triple-negative breast cancer (TNBC) cells showed 700,000-fold higher specificity for TNBC cells than unlabeled exosomes with miR-21-5p or transfected with miR-21-5p alone. Cellular internalization of the miR-21-5p leads to significant reduction of PTEN expression, thus demonstrating feasibility of genetic modulation by exosome delivered miR.

Functionalized vesicles can be customized with a wide range of functional elements and cargo to target specific cells and induce specific biological, chemical, physiological, pharmacological, etc., results. As discussed in more detail below, functional elements, lipids, lipid vehicles, cargos, detergents, dialysis membranes and other features can be combined, exchanged, or substituted, to generate customized functional vesicles for use in a variety of applications, including the treatment of diseases such as cancer.

A. Lipid-Based Vesicles

1. Vesicle Structure

The disclosed lipid-based vesicles (also referred to herein as vehicles) are modified to include a targeting moiety, typically conjugated to a lipid that inserts into, or otherwise forms part of, the lipid-based vesicle. Such targeting conjugates can be added to the vesicle during synthesis of the vesicle using, for example synthetic techniques that are known in the art. However, preferably, the conjugates are added to the vesicle after initial vesicle synthesis. Thus, lipid vesicle prior to the addition of the targeting conjugate can be referred to as initial lipid vesicle, starting lipid vesicle materials, or in any other way suitable to distinguish the lipid vesicle before and after the insertion or other addition of the targeting conjugate. For example, as discussed in more detail below, a particularly preferred technique includes dialysis of a mixture including initial lipid vesicles and lipid conjugates to form functionalized lipid vesicles that include the targeting conjugate.

The lipid vesicles can be any form of naturally-occurring or artificial or synthetic lipid-based vesicles. Such vesicles include, but are not limited to, apoptotic bodies and/or blebs (AB), microvesicles (MV), exosomes, tunneling nanotubes (TNT), niosomes, and liposomes.

In preferred embodiments, the vesicles are exosomes. Exosomes are small cell-derived vesicles that serve as conveyors of cellular information and have caused considerable excitement for their potential to deliver therapeutics. As a drug delivery vehicle, they are advantageous because they possess the surface proteins that promote endocytosis and they have the potential to deliver macromolecules. Also, if the exosomes are obtained from the same individual as they are delivered to, the exosomes will be immunotolerant.

Exosomes are vesicles with the size of 30-150 nm, often 40-100 nm, and are observed in most cell types. Exosomes are often similar to MVs with an important difference: instead of originating directly from the plasma membrane, they are generated by inward budding into multivesicular bodies (MVBs). The formation of exosomes includes three different stages: (1) the formation of endocytic vesicles from plasma membrane, (2) the inward budding of the endosomal vesicle membrane resulting in MVBs that consist of intraluminal vesicles (ILVs), and (3) the fusion of these MVBs with the plasma membrane, which releases the vesicular contents, known as exosomes.

Exosomes have a lipid bilayer with an average thickness of −5 nm (see e.g., Li, *Theranostics,* 7(3):789-804 (2017) doi: 10.7150/thno.18133). The lipid components of exosomes include ceramide (sometimes used to differentiate exosomes from lysosomes), cholesterol, sphingolipids, and phosphoglycerides with long and saturated fatty-acyl chains. The outer surface of exosomes is typically rich in saccharide chains, such as mannose, polylactosamine, alpha-2,6 sialic acid, and N-linked glycans.

Many exosomes contain proteins such as platelet derived growth factor receptor, lactadherin, transmembrane proteins and lysosome associated membrane protein-2B, membrane transport and fusion proteins like annexins, flotillins, GTPases, heat shock proteins, tetraspanins, proteins involved in multivesicular body biogenesis, as well as lipid-related proteins and phospholipases. These characteristic proteins therefore serve as good biomarkers for the isolation and quantification of exosomes. Another key cargo that exosomes carry is nucleic acids including deoxynucleic acids (DNA), coding and non-coding ribonucleic acid (RNA) like messenger RNA (mRNA) and microRNA (miRNA).

Although exosomes are preferred, other extracellular vesicles can also be used.

ABs are heterogenous in size and originate from the plasma membrane. They can be released from all cell types and are about 1-5 μm in size.

MVs with the size of 20 $nm^{-1}$ μm are formed due to blebbing with incorporation of cytosolic proteins. In contrast to ABs, the shape of MVs is homogenous. They originate from the plasma membrane and are observed in most cell types.

TNT are thin (e.g., 50-700 nm) and up to 100 μm long actin containing tubes formed from the plasma membrane.

As used herein, the terms AB, MV, exosomes, and TNT refer to naturally occurring lipid vesicles. They can be isolated from tissue, cells, and fluid directly from a subject, including cultured and uncultured tissue, cells, or fluids, and fluid derived or conditioned by cultured cells (e.g., conditioned media). For example, exosomes are present in physiological fluids such as plasma, lymph liquid, malignant pleural effusion, amniotic liquid, breast milk, semen, saliva and urine, and are secreted into the media of cultured cells.

As used herein, liposomes and niosomes refer to synthetic lipid vesicles.

Liposomes are a spherical vesicle composed of at least one bilayer of amphipathic molecules which forms a membrane separating an intravesicular medium from an external medium. The intravesicular medium constitutes the internal aqueous core of the liposome. Hydrophilic molecules or components, can be encapsulated inside the internal aqueous core of the liposome via active methods of encapsulation known in the art and described below. Hydrophobic molecules or components can be entrapped inside the membrane. The liposomes can be, for example, multilamellar vesicles (MLV), small unilamellar vesicles (SUV), large unilamellar vesicles (LUV), or cochleate vesicles. In some embodiments, the delivery composition is a micelle, or another lipid-based delivery vehicle. See, for example, Torchilin, et al., *Advanced Drug Delivery Reviews,* 58(14): 1532-55 (2006) doi: 10.1016/j.addr.2012.09.031, which is specifically incorporated by reference herein in its entirety.

Niosomes are non-ionic surfactant-based vesicles. Niosomes are formed most typically by non-ionic surfactant and cholesterol incorporation as an excipient, however, other excipients can also be used. Niosomes have more penetrating capability than the previous preparations of emulsions. They are structurally similar to liposomes in having a bilayer, but the fatty acids within the noisome have a single hydrophobic tail rather than two.

Synthetic vesicles can be designed to have some or all characteristics (e.g., size, shape, lipid content, etc.) that are similar or the same as naturally occurring counterparts including AB, MV, exosomes, and TNT. Thus, in some embodiments, liposomes that are more specifically designed to mimic a naturally occurring counterpart and can then be referred to as synesthetic or artificial exosomes, AB, MV, or TNT, etc.

2. Lipids

The disclosed lipid-based vesicles and the lipid conjugates disclosed herein typically include one or a combination of two or more lipids that can be neutral, anionic, or cationic at physiologic pH. The vesicles include, or otherwise can be formed from, any suitable lipid or combination of lipids. Likewise, the conjugates can include or otherwise be formed of any suitable lipid. In some embodiments, a combination of two, three, four, five, or more different lipid conjugates (e.g., different lipids and the same target moiety, different lipids and different targeting moieties, or the same lipid and different targeting moiety) can be inserted or otherwise added to the same lipid vesicle.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3- phosphocholines, 1-acyl-2-acyl-sn-glycero-3-phosphocholines, 1,2-diheptanoyl-SN-glycero-3-phosphocholine) derivatives of the lipids. The compositions can be generated from a single type of lipid, or a combination of two or more lipids.

The vesicles and conjugates may include a sphingomyelin metabolite. Sphingomyelin metabolites include, without limitation, ceramide, sphingosine, or sphingosine 1-phosphate (SlP). The concentration of the sphingomyelin metabolites included in the lipids of the vesicles can range from, for example, about 0.1 mol % to about 10 mol %, or from about 2.0 mol % to about 5.0 mol %, or can be in a concentration of about 1.0 mol %.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Other cationic lipids also include, but are not limited to, dimethyldioctadecyl ammonium bromide (DDAB), 1 ,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N-(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), diC$_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxylethyl)-2,3-dioleoyloxy-1,4-butanediammonium iodide. In some embodiments, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl) imidazolinium chloride (DPTIM). In some embodiments, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The compositions can be formed from a combination of more than one lipid, for example, a charged lipid may be combined with a lipid that is non-ionic or uncharged at physiological pH. Non-ionic lipids include, but are not limited to, cholesterol and DOPE.

In some embodiments, the vesicles and/or conjugates include or are formed of one or more of 1, 2-distearoyl-sn-glycero-3-phosphatidylcholine (DSPC), 1, 2-distearoyl-sn-glycero-3-phosphatidylethanolamine (DSPE), and 1, 2-distearoyl-sn-glycero-3-phosphoethanolamine-N-[poly (ethyleneglycol) 2000 (DSPE-PEG) and can include a sterol.

The vesicles and conjugates can include a sterol component. For example, a sterol component may be included to confer the vesicle suitable physicochemical and biological behavior. Such a sterol component may be selected from cholesterol or its derivative e.g., ergosterol or cholesterol-hemisuccinate, but it is preferably cholesterol. Cholesterol is often used in lipidic formulation of liposomes because it is generally recognized that the presence of cholesterol decreases their permeability and protects them from the destabilizing effect of plasma or serum proteins.

In some embodiments, particularly where the lipid is used in synthetic liposomes or niosomes, or as the lipid domain for the disclosed conjugates, the lipid can include a synthetic polymer poly-(ethylene glycol) (PEG) in liposome composition (see, e.g., Paphajopoulos, et al., PNAS, 88(24):11460-11464 (1991) doi: 10.1073/pnas.88.24.11460). The presence of PEG on the surface of the liposomal carrier has been shown to extend blood-circulation time while reducing mononuclear phagocyte system uptake. Further, by synthetic modification of the terminal PEG molecule, stealth liposomes can be actively targeted with monoclonal antibodies or ligands. Liposomes, including long circulating liposomes and stealth liposomes are reviewed in Immordino, et al, *Int J Nanomedicine,* 1(3):297-315 (2006) doi: 10.2217/17435889.1.3.297), which is specifically incorporated by reference herein in its entirety.

In preferred embodiments, the lipid includes a phospholipid-PEG conjugate. In liposomes composed of phospholipids and cholesterol, the ability of PEG to increase the circulation lifetime of the vesicles has been found to depend on both the amount of grafted PEG and the length or molecular weight of the polymer (Allen, et al., *Biochim Biophys Acta.,* 1066(1):29-36 (1991) doi: 10.1016/0005-2736(91)90246-5). In most cases, the longer-chain PEGs have produced the greatest improvements in blood residence time. For example, Allen et al reported that blood levels were higher for SM/PC/CHOL/DSPE-PEG liposomes with longer molecular weight PEG (i.e., PEG 1900 and PEG 5000) than for liposomes containing PEG-lipid with a shorter chain PEG (i.e., PEG 750 and PEG 120). The presence of PEG 2000 doubled the amount of lipid remaining in the plasma compared to formulations containing PEG 350 to 750. In some embodiments, the PEG is about PGE 350 to about PEG 5000, or between about PEG 750 and about PEG 5000, or between about PEG 1000 and PEG 3000. In a particular embodiment, the PEG is PEG 2000.

In addition to modulating the lipid composition, size, and charge of the vesicle to increase in vivo circulation, liposomal surfaces can be modified, for example, with glycolipids or sialic acid or PEG. In some embodiments, the lipid vehicle can be a "long circulating" or "sterically stabilized" or "stealth" lipid vehicle.

Long-circulating sterically-stabilized liposomes (SSL) have the ability to stably encapsulate drugs and facilitate drug delivery (Muggia, et al., *Current Oncol.* 2001; 3(2): 156-62 doi:10.1007/s11912-001-0016-5; Zhu, et al., *J Pharm Sci.* 2011; 100(8): 3146-59 doi: 10.1002/jps.22580; Marra, et al., *Biotechnology advances.* 2012; 30(1): 302-9. doi: 10.1016/j.biotechadv.2011.06.018). They can alter the pharmacokinetics of the drug, especially compared to free drug and sometimes enhance their pharmacological activity (Muggia, et al., *Current Oncol.* 2001; 3(2): 156-62. doi: 10.1007/s11912-001-0016-5). Tumor specific drug delivery using lipid-based nanoparticulate drug carriers, such as SSL, have been used to encapsulate and release drugs, often with higher efficiency compared to free drug (Gabizon, et al., *Horiz Biochem Biophys.* 1989; 9: 185-211 PMID: 2656476). Differences in the half-life and/or tissue and tumor distribution are believed to be primary drivers for these actions. Additionally, SSL are also believed to decrease off-targeted toxicity (Lasic, et al., *Biochimica et biophysica acta.* 1991; 1070(1): 187-92 doi: 10.1016/0005-2736(91)90162-2, Sharma, et al., *Pharm Res.* 1997; 14(8): 992-8; doi:10.1023/A:1012136925030). DOXIL® is an example of a clinically approved nanoparticle-encapsulating the anti-cancer drug doxorubicin. In addition to their ability to stabilize drugs and enhance their bio-distribution, SSL accumulate passively in solid tumors due to the enhanced permeability and retention effect mediated by defects in the vasculature and lack of functional lymphatics (Maeda, et al., *J Control Release.* 2000; 65: 271-84 doi: 10.1016/S0168-3659(99)00248-5, Yuan, et al., *Cancer research.* 1994; 54: 3352-6 PMID: 8012948).

In some of the experiments below Avanti Total polar extract is utilized for making liposomes.

B. Conjugates

The disclosed vesicles include a functional element conjugated or otherwise linked to a lipid (also referred to herein as lipid component).

Suitable lipids include, but are not limited to, those discussed above with respect to the lipid vesicles. In some embodiments, the lipid component of the conjugate is different from the other lipid(s) that form the lipid vesicle. In particular embodiments, the lipid component of the conjugate is a fatty acid or a pegylated fatty acid. As discussed above, the lipid can include a PEG molecule. In some embodiments the lipid is the same as at least one of the lipids that forms the lipid vesicle. In particular embodiments the lipid is 1,2-disteroyl-sn-glycero-3-phosphoethanolamine (DSPE) with or without a PEG molecule. The lipid component can also be formed from a precursor that includes a chemical moiety that facilitates conjugation, attachment, or another suitable linkage with a functional element.

The functional element can be, for example, a small molecule, protein or polypeptide, carbohydrate, nucleic acid or a combination thereof. The functional moieties can serve a variety of different functions; such as enhancing targeting of the vehicle, inducing intracellular uptake of the target cell, endosome disruption in the target cell, tracking or otherwise monitoring or identifying the vehicle, or a combination thereof. The lipid vesicles can include a combination of two or more of the same or different types of moieties.

1. Targeting Moieties

In particularly preferred embodiments, the conjugate is a targeting moiety. The targeting moiety typically increases attachment, binding, or association of the lipid vesicle to a target cell(s), tissues(s), and/or microenvironment(s) relative other (e.g., non-targeted) cell(s), tissue(s), and/or microenvironment(s). Additionally, or alternatively, the conjugate can enhance cell penetration.

Typically, targeting moieties include a targeting domain and a lipid. Targeting moieties can also include additional domains. For example, the targeting moiety can include one or more linker domains. The targeting domain is conjugated or otherwise linked directly or indirectly to the lipid domain. In some embodiments the targeting domain is conjugated or linked to the lipid domain through a linker.

A targeting domain typically includes or consists of one or more targeting molecules. Exemplary target molecules can include proteins, peptides, nucleic acids, saccharides, or polysaccharides that bind to one or more targets associated with an organ, tissue, cell, extracellular matrix, etc. In some embodiments, the targeting molecule may preferentially bind to a specific type of tumor or infected cell.

The degree of specificity with which the disclosed lipid vesicles are targeted can be modulated through the selection of a targeting molecule with the appropriate affinity and specificity. For example, a targeting molecule can be a polypeptide, such as an antibody that specifically recognizes a tumor marker that is present exclusively or in higher amounts on a malignant cell (e.g., a tumor antigen). Suitable targeting molecules that can be used to direct lipid vesicles to cells and tissues of interest, for example cancerous tissue, that are known in the art.

For example, antibodies are very specific. These can be polyclonal, monoclonal, fragments, recombinant, or single chain, many of which are commercially available or readily obtained using standard techniques.

The antibodies can be fragment of a full-length antibody, or a fusion protein formed for segments of the antibody. Exemplary antibody fragments and fusions include, but are not limited to, single chain antibodies, single chain variable fragments (scFv), di-scFv, tri-scFv, diabody, triabody, teratbody, disulfide-linked Fvs (sdFv), Fab', $F(ab')_2$, Fv, and single domain antibody fragments (sdAb).

Examples of moieties include, for example, targeting moieties which provide for the delivery of molecules to specific cells, e.g., antibodies to hematopoietic stem cells, $CD34^+$ cells, T cells or any other preferred cell type, as well as receptors and ligands expressed on the preferred cell type. Preferably, the moieties target hematopoeitic stem cells.

Targeting molecules can also include neuropilins and endothelial targeting molecules, integrins, selectins, and adhesion molecules.

Examples of molecules targeting extracellular matrix ("ECM") include glycosaminoglycan ("GAG") and collagen.

Other useful ligands attached to lipids include pathogen-associated molecular patterns (PAMPs). PAMPs target Toll-like Receptors (TLRs) on the surface of the cells or tissue, or signal the cells or tissue internally, thereby potentially increasing uptake. PAMPs conjugated to the particle surface or co-encapsulated may include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

An immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins can render lipid vesicles target-specific to the mucin and mucosal cell layer include lectins isolated from *Abrus precatroius, Agaricus bisporus, Anguilla, Arachis hypogaea, Pandeiraea simplicifolia, Bauhinia purpurea, Caragan arobrescens, Cicer arietinum, Codiumfragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I II and III, *Sambucus nigra, Maackia*

*amurensis, Limax fluvus, Homarus americanus, Cancer antennarius*, and Lotus tetragonolobus.

The choice of targeting molecule will depend on the cells or tissues to be targeted. The targeting molecule may generally increase the binding affinity of the vesicles for cell or tissues or may target the vesicles to a particular cell type in a tissue.

In some embodiments, the targeting domain includes or is a positively charged molecule such as avidin, polyethyleneimine or polylysine, that increases the binding of the vesicles to a negatively charged surface or substrate such as extracellular matrix or mucus layers.

Epithelial cell targeting molecules include monoclonal or polyclonal antibodies or bioactive fragments thereof that recognize and bind to epitopes displayed on the surface of epithelial cells. Epithelial cell targeting molecules also include ligands that bind to a cell surface receptor on epithelial cells.

A variety of receptors on epithelial cells may be targeted by epithelial cell targeting molecules. Examples of suitable receptors to be targeted include, but are not limited to, IgE Fc receptors, EpCAM, selected carbohydrate specificites, dipeptidyl peptidase, and E-cadherin.

Additional strategies and exemplary targets for targeting domains are provide below and are particularly useful for the treatment of cancer.

a. Molecular classes of targeting domains i. Ligands and receptors

In one embodiment, tumor or tumor-associated neovasculature targeting domains are ligands that bind to cell surface antigens or receptors that are specifically expressed on tumor cells or tumor-associated neovasculature or are overexpressed on tumor cells or tumor-associated neovasculature as compared to normal tissue. Tumors also secrete a large number of ligands into the tumor microenvironment that affect tumor growth and development. Receptors that bind to ligands secreted by tumors, including, but not limited to, growth factors, cytokines and chemokines, including the chemokines discussed above, are suitable as targeting domains for the vesicles disclosed herein. Ligands secreted by tumors can be targeted using soluble fragments of receptors that bind to the secreted ligands. Soluble receptor fragments are fragments of polypeptides that may be shed, secreted or otherwise extracted from the producing cells and include the entire extracellular domain, or fragments thereof.

ii. Antibodies

In another embodiment, tumor or tumor-associated neovasculature targeting domains are antibodies, for example, single polypeptide antibodies that bind to cell surface antigens or receptors that are specifically expressed on tumor cells or tumor-associated neovasculature or are overexpressed on tumor cells or tumor-associated neovasculature as compared to normal tissue.

iii. Fc domains

In another embodiment, tumor or tumor-associated neovasculature targeting domains are Fc domains of immunoglobulin heavy chains that bind to Fc receptors expressed on tumor cells or on tumor-associated neovasculature. As defined herein, the Fc region includes polypeptides containing the constant region of an antibody excluding the first constant region immunoglobulin domain. Thus Fc refers to the last two constant region immunoglobulin domains of IgA, IgD, and IgG, and the last three constant region immunoglobulin domains of IgE and IgM. In a preferred embodiment, the Fc domain is derived from a human or murine immunoglobulin. In a more preferred embodiment, the Fc domain is derived from human IgG1 or murine IgG2a including the $C_H2$ and $C_H3$ regions.

b. Antigens, Ligands, and Receptors to Target i. Tumor-Specific and Tumor-Associated Antigens In some embodiments, the targeting domain specifically binds to an antigen that is expressed by tumor cells. The antigen expressed by the tumor may be specific to the tumor, or may be expressed at a higher level within the tumor cells than non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are known.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erbB gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al., *Int. J. Cancer,* 106:817-20 (2003) doi: 10.1002/ijc.11292; Kennedy, et al., *Int. Rev. Immunol.,* 22:141-72 (2003) doi: 10.1080/08830180305222; Scanlan, et al. *Cancer Immun.,* 4:1 (2004) PMID: 14738373).

Genes that encode cellular tumor associated antigens include cellular oncogenes and proto-oncogenes that are aberrantly expressed. In general, cellular oncogenes encode products that are directly relevant to the transformation of the cell, so these antigens are particularly preferred targets for oncotherapy and immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983) doi: 10.1056/NEJM198310133091503; Lloyd, et al., *Int. J. Canc.,* 71:842 (1997) doi: 10.1002/(SICI)1097-0215(19970529)71:5<842::AID-IJC24>3.0.CO;2-8. CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997) doi: 10.3109/02841869709001350; Sarandakou, et al., *Eur. J. Gynaecol. Oncol.,* 19(1):73-77 (1998) PMID: 9476065; Meier, et al., *Anticancer Res.,* 17(4B):2945 (1997) PMID: 9329571; Kudoh, et al., *Gynecol. Obstet. Invest.,* 47:52 (1999) doi: 10.1159/000010062). Elevated serum CA125 may also accompany neuroblastoma (e.g., Hirokawa, et al., *Surg. Today,* 28 (3):349-354 (1998) doi: 10.1007/s005950050139), while elevated CEA and SCC, among others, may accompany colorectal cancer (Gebauer, et al., *Anticancer Res.,* 17(4B):2939-2942 (1997) PMID: 9329569).

The tumor associated antigen mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52(1):181-186 (1992) PMID: 1727378; Chang, et al., *Int. J. Cancer,* 50:373 (1992) doi: 10.1002/ijc.2910500308; Chang, et al., *Int. J. Cancer,* 51:548 (1992) doi: 10.1002/ijc.2910510408; Chang, et al., *Proc. Natl. Acad. Sci. USA,* 93:136 (1996) doi: 10.1073/pnas.93.1.136; Chowdhury, et al., *Proc. Natl. Acad. Sci. USA,* 95:669 (1998) doi: 10.1073/pnas.95.2.669). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer,* 50:373 (1992) doi: 10.1002/ijc.2910500308). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession NO: U48722), HER2 (Yoshino, et al., *J. Immunol.,* 152 (5):2393-2400 (1994) PMID: 8133050; Disis, et al., Canc. Res., 54 (1):16-20 (1994) PMID: 7505195; GenBank Acc. Nos. X03363 and M17730), HER3 (GenBank Acc. Nos. U29339 and M34309), HER4 (Plowman, et al., *Nature,* 366:473 (1993) doi: 10.1038/366473a0; GenBank Acc. Nos. L07868 and T64105), epidermal growth factor receptor (EGFR) (GenBank Acc. Nos. U48722, and K03193), vascular endothelial cell growth factor (GenBank NO: M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA,* 78:3039 (1981) doi: 10.1073/pnas.78.5.3039; GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA,* 86:7159 (1989) doi: 10.1073/pnas.86.18.7159; GenBank Acc. Nos. M65132 and M64928) NY-ESO-1 (GenBank Acc. Nos. AJO03149 and U87459), NA 17-A (PCT Publication NO: WO 96/40039), Melan-A/MART-1 (Kawakami, et al., *Proc. Nat. Acad. Sci. USA,* 91:3515 (1994) doi: 10.1073/pnas.91.9.3515; GenBank Acc. Nos. U06654 and U06452), tyrosinase (Topalian, et al., *Proc. Nat. Acad. Sci. USA,* 91:9461 (1994) doi: 10.1073/pnas.91.20.9461; GenBank Acc. NO: M26729; Weber, et al., J. Clin. Invest, 102:1258 (1998) doi:10.1172/JCI4004.), Gp-100 (Kawakami, et al., *Proc. Nat. Acad. Sci. USA,* 91:3515 (1994) doi: 10.1073/pnas.91.9.3515; GenBank Acc. NO: 573003, Adema, et al., *J. Biol. Chem.,* 269 (31):20126-20133 (1994) PMID: 7519602), MAGE (van den Bruggen, et al., *Science,* 254:1643 (1991) doi: 10.1126/science.1840703); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. NO: U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, *J. Exp. Med.,* 121:439 (1965) doi: 10.1084/jem.121.3.439; GenBank Acc. Nos. M59710, M59255 and M29540), and PyLT (GenBank Acc. Nos. J02289 and J02038); p$^{97}$ (melanotransferrin) (Brown, et al., *J. Immunol.,* 127 (2):539-546 (1981) PMID: 6166674; Rose et al., *Proc. Natl. Acad. Sci. USA,* 83:1261-61 (1986) doi: 10.1073/pnas.83.5.1261). Additional tumor associated antigens include prostate surface antigen (PSA) (U.S. Pat. Nos. 6,677,157; 6,673,545); β-human chorionic gonadotropin β-HCG) (McManus, et al., *Cancer Res.,* 36 (9 PT 2):3476-3481 (1976) PMID: 975106; Yoshimura, et al., *Cancer,* 73:2745-52 (1994) doi:/10.1002/1097-0142(19940601)73:11<2745::AID-CNCR2820731116>3.0.CO;2-V; Yamaguchi, et al., *Br. J. Cancer,* 60:382-84 (1989) doi: 10.1038/bjc.1989.289: Alfthan, et al., *Cancer Res.,* 52:4628-33 (1992) PMID: 1324787); glycosyltransferase β-1,4-N-acetylgalactosaminyltransferases (GalNAc) (Hoon, et al., Int. J. Cancer, 43:857-62 (1989) doi: 10.1002/ijc.2910430520; Ando, et al., *Int. J. Cancer,* 40:12-17 (1987) doi: 10.1002/ijc.2910400104; Tsuchida, et al., *J. Natl. Cancer,* 78:45-54 (1987) doi: 10.1002/1097-0142(19890315)63:6<1166::AID-CNCR2820630621>3.0.CO;2-5; Tsuchida, et al., *J. Natl. Cancer,* 78:55-60 (1987) doi: 10.1093/jnci/78.1.55); NUC18 (Lehmann, et al., *Proc. Natl. Acad. Sci. USA,* 86:9891-95 (1989) doi: 10.1073/pnas.86.24.9891; Lehmann, et al., *Cancer Res.,* 47:841-45 (1987) PMID: 3542195); melanoma antigen gp75 (Vijayasardahi, et al., *J. Exp. Med.* 171:1375-80 (1990) doi: 10.1084/jem.171.4.1375; GenBank Accession NO: X51455); human cytokeratin 8; high molecular weight melanoma antigen (Natali, et al., *Cancer,* 59:55-63 (1987) doi:10.1002/1097-0142(19870101)59:1<55::AID-CNCR2820590115>3.0.CO;2-R; keratin 19 (Datta, et al., *J. Clin. Oncol.* 12:475-82 (1994) doi:10.1200/JCO.1994.12.3.475).

Tumor antigens of interest include antigens regarded in the art as cancer/testis (CT) antigens that are immunogenic in subjects having a malignant condition (Scanlan, et al., *Cancer Immun.,* 4:1 (2004) PMID: 14738373). CT antigens include at least 19 different families of antigens that contain one or more members and that are capable of inducing an immune response, including, but not limited to, MAGEA (CT1); BAGE (CT2); MAGEB (CT3); GAGE (CT4); SSX (CT5); NY-ESO-1 (CT6); MAGEC (CT7); SYCP1 (C8);

SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but are not limited to, α-actinin-4, Bcr-Abl fusion protein, Casp-8, β-catenin, cdc27, cdk4, cdkn2a, coa-1, dek-can fusion protein, EF2, ETV6-AMLI fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, $-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29BCAA), CA 195, CA 242, CA-50, CAM43, CD68KP1, CO-029, FGF-5, G250, Ga733 (EpCAM), HTgp-175, M344, MA-50, MG7-Ag, MOV18, NB70K, NY-CO-1, RCAS1, SDCCAG16, TA-90 (Mac-2 binding proteincyclophilin C-associated protein), TAAL6, TAG72, TLP, and TPS. Other tumor-associated and tumor-specific antigens are known to those of skill in the art and are suitable for targeting by the disclosed fusion viruses.

ii. Antigens associated with tumor neovasculature

Cancer therapeutics can be more effective in treating tumors by targeting to blood vessels of the tumor. Tumor-associated neovasculature provides a readily accessible route through which viral therapeutics can access the tumor. In some embodiments the targeting domain specifically binds to an antigen that is expressed by neovasculature associated with a tumor.

The antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed vesicles.

iii. Chemokines/chemokine receptors

In another embodiment, the targeting domain is engineered to specifically bind to a chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are vital for tumor progression.

Based on the positioning of the conserved two N-terminal cysteine residues of the chemokines, they are classified into four groups: CXC, CC, CX3C and C chemokines. The CXC chemokines can be further classified into ELR+ and ELR− chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

iv. Targets from Experiments

In some embodiments, the targeting moiety specifically targets a target exemplified in the experiments below, including, for example, ENPP2/autotaxin, CD44, CD29/Integrin beta-1, I-CAM, or Asialoglycoprotein Receptor 1/HL-1 antibody.

c. Exemplary Targeting Moieties

Suitable antibodies, fragments thereof, and other targeting moieties are known in the art and can be used in the disclosed compositions and methods. See, for example, Firer and Gellerman, *J Hematol Oncol.,* 5: 70 (2012), doi: 10.1186/1756-8722-5-70, Lambert and Berkenblit, *Annu Rev Med.,* 69:191-207 (2018), doi: 10.1146/annurev-med-061516-121357, Diamantis and Banerji, *Br J Cancer,* 114 (4):362-7 (2016). doi: 10.1038/bjc.2015.435. Epub 2016 Jan. 7, and Chiavenna, et al., *J Biomed Sci.* 2017; 24: 15, Published online 2017 Feb. 20. doi: 10.1186/s12929-016-0311-y, each of which is specifically incorporated by reference herein in its entirety.

Specific, non-limiting examples, of antibodies and fragment and fusion proteins thereof that can be used in the disclosed compositions and methods for the targeting and treatment of cancer, include, but are not limited to, those utilized in the experiments provided herein including:

Anti-ENPP2/autotaxin (Invitrogen Product No. PA5-12478

Anti-CD44 (Cell Signaling Technologies Product No. #37259S)

Anti-CD29/Integrin beta-1 (Cell Signaling Technologies Product No. #4706S)

Anti-I-CAM (Cell Signaling Technologies Product #4915S)

Anti-Asialoglycoprotein Receptor 1/HL-1 (abCAM, Product Number: ab49355).

Specific, non-limiting examples, of antibodies and fragment and fusion proteins thereof that can be used in the disclosed compositions and methods for the targeting and treatment of cancer, include, but are not limited to, those described in Tables 1-4.

TABLE 1

Target antigens in solid tumors (Antibody-Drug Conjugates (ADC)) (adapted from Diamantis and Banerji, *Br J Cancer*, 114(4): 362-7 (2016))

| Name | ADC | Lead indication |
|---|---|---|
| Target antigens overexpressed in cancer cells | | |
| GPNMB | Glembatumumab vedotin | Breast cancer and melanoma |
| CD56 | Lorvotuzumab mertansine (IMGN-901) | SCLC |
| TACSTD2 (TROP2) | sacituzumab govitecan (IMMU-132) | TNBC and pancreatic cancer |
| CEACAM5 | Labetuzumab SN-38 | Colorectal cancer |
| Folate receptor-α | Mirvetuximab soravtansine (IMGN-853), Vintafolide | Ovarian and endometrial cancer |
| Mucin 1 (Sialoglycotope CA6) | SAR-566658 | Breast, ovarian, cervical, lung and pancreatic cancer |
| STEAP1 | Vandortuzumab vedotin RG-7450 | Prostate cancer |
| Mesothelin | DMOT4039A, Anetumab ravtensine (BAY-94-9343) | Ovarian, pancreatic cancer and mesothelioma |
| Nectin 4 | Enfortumab vedotin (ASG-22M6E), ASC-22CE | Bladder, breast, lung and pancreatic cancer |
| ENPP3 | AGS-16M8F | Renal cell carcinoma, liver carcinoma and prostate cancer |
| Guanylyl cyclase C (GCC) | Indusatumab vedotin (MLN-0264) | Pancreatic and colorectal cancer |
| SLC44A4 | ASG-5ME | Pancreatic, gastric and prostate cancer |
| NaPi2b | anti-NaPi2b ADC, Lifastuzumab vedotin | Non-small cell lung cancer and platinum-resistant ovarian cancer |
| CD70 (TNFSF7) | DNIB0600A, AMG-172, MDX-1203, Vorsetuzumab mafodotin SGN-75 | Renal cell carcinoma |
| CA9, Carbonic anhydrase | BAY79-4620 | Solid tumours |
| 5T4 (TPBG) | PF 06263507 | Solid tumours |
| SLTRK6 | ASG-15ME | Bladder cancer |
| SC-16 (anti-Fyn3) | SC16LD6.5 | SCLC NSCLC and ovarian cancer |
| Tissue factor | HuMax-TF-ADC (TF-011-MMAE) | Solid tumours |
| LIV-1 (ZIP6) | SGN-LIV1A | Breast cancer |
| P-Cadherin | PCA062 | Solid tumours |
| PSMA | MLN2704, PSMA-ADC | Prostate cancer |
| Target antigens in the tumour vasculature and stroma | | |
| Fibronectin Extra-domain B (ED-B) | Human mAb L19 and F8 | Solid tumours |
| Endothelin receptor ETB | RG-7636 | Melanoma |
| VEGFR2 (CD309) | Anti-VEGFR-2ScFv-As2O3-stealth Nanoparticles | Solid tumours |
| Tenascin c | Anti-TnC-A1 antibody SIP(F16) | Solid tumours |
| Collagen IV | Cytotoxic immunoconjugates | Solid tumours |
| Periostin | Anti-periostin antibody | Solid tumours |

TABLE 1-continued

Target antigens in solid tumors (Antibody-Drug Conjugates (ADC)) (adapted from Diamantis and Banerji, *Br J Cancer*, 114(4): 362-7 (2016))

| Name | ADC | Lead indication |
|---|---|---|
| Target antigens regulated from driver oncogenes | | |
| HER 2 | T-DM1, ARX788, SYD985 | Breast cancer |
| EGFR | ABT-414, IMGN289, AMG-595 | Glioblastoma, NSCLC, head and neck, breast, oesophageal |
| Target antigens in haematological malignancies | | |
| CD30 | Brentuximab vedotin, Iratumumab MDX-060 | HL and ALCL |
| CD22 | Inotuzumab ozogamicin (CMC-544), Pinatuzumab vedotin, Epratuzumab SN38 | NHL and ALL |
| CD79b | Polatuzumab vedotin | DLBCL and follicular NHL |
| CD19 | Coltuximab ravtansine, SAR-3419 | DLBCL and ALL |
| CD138 | Indatuximab ravtansine | Multiple myeloma |
| CD74 | Milatuzumab doxorubicin | CLL, NHL and multiple myeloma |
| CD37 | IMGN-529 | NHL and CLL |
| CD33 | IMGN779, SGN CD33 A | AML |
| CD19 | SGN-CD19A | ALL and NHL, |
| CD98 | IGN523 | AML |

Abbreviations: ADC = antibody-drug conjugate; ALL = acute lymphocytic leukemia; AML = acute myelogenous leukemia; CLL = chronic lymphocytic leukemia; DLBCL = diffuse large B-cell lymphoma; HL = Hodgkin lymphoma; NHL = non-Hodgkin lymphoma; NSCLC = non-small cell lung cancer; SCLC = small cell lung cancer; TNBC = triple-negative breast cancer.

TABLE 2

Antibody-drug conjugates (ADCs) marketed, in clinical trials, or in phase II development for treating hematologic malignancies (adapted from Lambert and Berkenblit, *Annu Rev Med.*, 69: 191-207 (2018), doi: 10.1146/annurev-med-061516-121357)

| ADC | Target antigen | Linker cytotoxic compound | Antibody[a] | Indication[c] |
|---|---|---|---|---|
| Gemtuzumab ozogamicin | CD33 | Cleavable hydrazone N-acetyl-γ calicheamicin | Engineered huIgG4 | AML |
| Brentuximab vedotin | CD30 | Cleavable dipeptide (vc) MMAE (auristatin) | chIgG1 | HL and systemic ALCL |
| Inotuzumab ozogamicin | CD22 | Cleavable hydrazone N-acetyl-γ calicheamicin | Engineered huIgG4 | B-ALL, other B cell malignancies |
| Vadastuximab talirine | CD33 | Cleavable dipeptide (va) PBD dimer | huIgG1 engineered for site-specific linking | AML |
| Polatuzumab vedotin | CD79b | Cleavable dipeptide (vc) MMAE (auristatin) | huIgG1 | DLBCL and FL |
| Denintuzumab mafodotin | CD19 | Noncleavable (mc) MMAF (auristatin) | huIgG1 | DLBCL and FL |
| Naratuximab emtansine | CD37 | Noncleavable (SMCC) DM1 (maytansinoid) | huIgG1[b] (selected to induce apoptosis) | DLBCL and FL |

TABLE 2-continued

Antibody-drug conjugates (ADCs) marketed, in clinical trials, or in phase II development for treating hematologic malignancies (adapted from Lambert and Berkenblit, *Annu Rev Med.*, 69: 191-207 (2018), doi: 10.1146/annurev-med-061516-121357)

| ADC | Target antigen | Linker cytotoxic compound | Antibody[a] | Indication[c] |
|---|---|---|---|---|
| Coltuximab ravtansine | CD19 | Cleavable disulfide (SPDB) DM4 (maytansinoid) | huIgG1[b] | DLBCL |
| Indatuximab ravtansine | CD138 | Cleavable disulfide (SPDB) DM4 (maytansinoid) | chIgG4 | Multiple myeloma |

[a]Antibody abbreviations: huIgG, humanized IgG; chIgG, chimeric IgG.
[b]Although these antibodies were humanized, changes in naming methodology at International Nonproprietary Names resulted in the "ximab" suffix of chimeric antibodies.
[c]Abbreviations: ALCL, anaplastic large cell lymphoma; AML, acute myeloid leukemia; B-ALL, B cell acute lymphoblastic leukemia; DLBCL, diffuse large cell lymphoma; FDA, United States Food and Drug Administration;

TABLE 3

Antibody-drug conjugates (ADCs) marketed, in pivotal clinical trials, or in phase II development for treating solid tumors (adapted from Lambert and Berkenblit, *Annu Rev Med.*, 69: 191-207 (2018), doi: 10.1146/annurev-med-061516-121357)

| ADC | Target antigen[d] | Linker cytotoxic compound | Antibody[a] | Tumor type(s)[d] |
|---|---|---|---|---|
| Ado-trastuzumab emtansine (T-DM1) | HER2 (ErbB2) | Non-cleavable (SMCC) DM1 (maytansinoid) | huIgG1 (trastuzumab) | HER2-positive mBC |
| Anetumab ravtansine | Mesothelin | Cleavable disulfide (SPDB) DM4 (maytansinoid) | human IgG1 (phage-derived) | Mesothelioma and other solid tumors |
| Mirvetuximab soravtansine | FOLR1 (FRα) | Cleavable disulfide (sSPDB) DM4 (maytansinoid) | huIG1[b] | Ovarian cancer, endometrial, NSCLC |
| Rovalpituzumab tesirine (Rova-T) | DLL3 | Cleavable dipeptide (va) PBD dimer | huIgG1 | SCLC |
| Sacituzumab govitecan | Trop-2 | Acid-labile ester linker SN-38 | huIgG1 | TNBC, urothelial and other cancers |
| Glembatumumab vedotin | gpNMB | Cleavable dipeptide (vc) MMAE (auristatin) | human IgG2 (tg mouse) | mBC and melanoma |
| Depatuxizumab mafodotin | EGFR | Non-cleavable (mc) MMAF (auristatin) | huIgG1 (ABT-806) | Glioblastoma and other EGFR+ tumors |
| AGS-16C3F | ENPP3 (CD203c) | Non-cleavable (mc) MMAF (auristatin) | human IgG2 (tg mouse) | Renal cell carcinoma |

TABLE 3-continued

Antibody-drug conjugates (ADCs) marketed, in pivotal clinical trials, or in phase II development for treating solid tumors (adapted from Lambert and Berkenblit, *Annu Rev Med.*, 69: 191-207 (2018), doi: 10.1146/annurev-med-061516-121357)

| ADC | Target antigen[d] | Linker cytotoxic compound | Antibody[a] | Tumor type(s)[d] |
|---|---|---|---|---|
| SAR566658 | CA6 | Cleavable disulfide (SPDB) DM4 (maytansinoid) | huIgG1[b] | TNBC and other CA6-positive tumors |
| PSMA-ADC | PSMA | Cleavable dipeptide (vc) MMAE (auristatin) | human IgG1 (tg mouse) | Prostate cancer |

[a]Antibody abbreviations: huIgG, humanized IgG; chIgG, chimeric IgG; tg mouse, transgenic mouse with human Ig repertoire.
[b]Although these antibodies were humanized, changes in naming methodology at International Nonproprietary Names resulted in the "ximab" suffix of chimeric antibodies.
[c]Abbreviations: DLL3, delta-like protein 3; EGFR, epidermal growth factor receptor; ENPP3, ectonucleotide pyrophosphatase/phosphodiesterase 3; FOLR1 or FRα, folate receptor alpha; gpNMB, glycoprotein non-metastatic B; FL, follicular lymphoma; mBC, metastatic breast cancer; NSCLC, non-small cell lung cancer; TNBC, triple-negative breast cancer; PSMA, prostate-specific membrane antigen; MMAE/F, mono methyl auristatin E/mono methyl auristatin F; PBD, pyrrolobenzodiazepine; DM1, N2'-deacetyl-N2'-(3-mercapto-1-oxopropyl)-maytansine; DM4, N2'-deacetyl-N2'-(4-mercapto-4-methyl-1-oxopentyl)-maytansine; SMCC, succinimidyl-4-(N-maleimidomethyl)cyclohexane-1-carboxylate; SPDB, N-succinimidyl-4-(2-pyridyldithio)butyrate; sSPDB, N-succinimidyl 4-(2-pyridyldithio)-2-sulfobutanoate; vc, valine-citrulline; va, valine-alanine.

TABLE 4

Summary of FDA approved monoclonal antibodies for treatment of solid tumors (adapted from Chiavenna, et al., *J Biomed Sci.* 2017; 24: 15, Published online 2017 Feb. 20. doi: 10.1186/s12929-016-0311-y)

| mAB | Name | Type | Target | FDA approved |
|---|---|---|---|---|
| Trastuzumab | Herceptin ® | Humanized | HER2 | HER2-positive metastatic/non-metastatic breast cancer<br>HER2-positive metastatic gastric or gastroesophageal junction adenocarcinoma |
| Pertuzumab | Perjeta ® | Humanized | HER2 | HER2-positive metastatic breast cancer<br>HER2-positive, locally advanced, inflammatory, or early stage breast cancer |
| Cetuximab | Erbitux ® | Chimeric | EGFR | Metastatic CRC<br>HNSCC |
| Panitumumab | Vectibix ® | Human | EGFR | Metastatic CRC |
| Necitumumab | Portrazza ™ | Human | EGFR | Metastatic squamous NSCLC |
| Dinutuximab | Unituxin ™ | Chimeric | GD2 | Pediatric high risk neuroblastoma |
| Bevacizumab | Avastin ® | Humanized | VEGF-A | Metastatic CRC<br>Recurrent or metastatic non-squamous NSCLC<br>HER2-negative metastatic breast cancer (revoked in 2011)<br>Metastatic renal cell carcinoma<br>Persistent, recurrent or metastatic cervical cancer<br>Glioblastoma<br>Recurrent epithelial ovarian, fallopian tube, or primary peritoneal cancer |
| Ramucirumab | Ciramza ® | Human | VEGFR-2 | Advanced or metastatic gastric or gastroesophageal junction adenocarcinoma<br>Metastatic NSCLC<br>Metastatic CRC |
| Olaratumab | Lartruvo ® | Human | PDGFR-α | Soft tissue sarcoma |
| Ipilimumab | Yervoy ® | Human | CTLA-4 | Unresectable or metastatic melanoma<br>Cutaneous melanoma |

TABLE 4-continued

Summary of FDA approved monoclonal antibodies for treatment of solid tumors (adapted from Chiavenna, et al., *J Biomed Sci.* 2017; 24: 15, Published online 2017 Feb. 20. doi: 10.1186/s12929-016-0311-y)

| mAB | Name | Type | Target | FDA approved |
|---|---|---|---|---|
| Nivolumab | Opdivo ® | Human | PD-1 | Unresectable or metastatic melanoma<br>Metastatic squamous NSCLC<br>Metastatic NSCLC<br>Advanced RCC<br>Recurrent or metastatic HNSCC |
| Pembrolizumab | Keytruda ® | Humanized | PD-1 | Unresectable or metastatic melanoma<br>Metastatic NSCLC<br>Recurrent or metastatic HNSCC |
| Atezolizumab | Tecentriq ™ | Humanized | PD-L1 | Locally advanced or metastatic urothelial carcinoma<br>Metastatic NSCLC |
| Ado-trastuzumab emtansine (Trastuzumab covalently linked to emtansine (DM1)) | Kadcyla ® | Humanized | HER2 | HER2-positive metastatic breast cancer |
| Denosumab | Xgeva ® | Human | RANKL | Bone metastases from solid tumors |

2. Tracking, Imaging, and Diagnostic Moieties

In some embodiments, the functional element include or is a tracking, imaging, or diagnostic moiety.

Exemplary agents include paramagnetic molecules, fluorescent compounds, magnetic molecules, and radionuclides, x-ray imaging agents, and contrast agents.

For imaging, radioactive materials such as Technetium99 ($^{99m}$Tc) or magnetic materials such as $Fe_2O3$ could be used. Examples of other materials include gases or gas emitting compounds, which are radioopaque. The most common imaging agents for brain tumors include iron oxide and gadolinium. Diagnostic agents can be radioactive, magnetic, or x-ray or ultrasound-detectable. Other detectable labels include, for example, radioisotopes, fluorophores (e.g., fluorescein isothiocyanate (FITC), phycoerythrin), enzymes (e.g., alkaline phosphatase, horseradish peroxidase), element particles (e.g., gold particles) or contrast agents.

For example, a fluorescent label can be chemically conjugated to a lipid to yield a fluorescently labeled lipid as exemplified below. In other embodiments the label is a contrast agent. A contrast agent refers to a substance that enhances the contrast of structures or fluids within the body in medical imaging. Contrast agents are known in the art and include, but are not limited to agents that work based on X-ray attenuation and magnetic resonance signal enhancement. Suitable contrast agents include iodine and barium.

C. Active Agents

Agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered.

Exemplary materials to be incorporated are drugs and imaging agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5-FU, methotrexate, adriamycin, camptothecin, epothilones A-F, and taxol), antibodies and bioactive fragments thereof (including humanized, single chain, and chimeric antibodies), antigen and vaccine formulations, peptide drugs, anti-inflammatories, nutraceuticals such as vitamins, and nucleic acid drugs (including DNA, RNAs including mRNAs, antisense, siRNA, miRNA, anti-miRNA, piwi-interacting RNA (piRNA), aptamers, ribozymes, external guide sequences for ribonuclease P, and triplex forming agents such as "tail-clamp" peptide nucleic acids (tcPNAs)). In some embodiments, the active agent is a vector, plasmid, or other polynucleotide encoding a nucleic acid such as those discussed above.

Exemplary drugs to be delivered include anti-angiogenic agents, antiproliferative and chemotherapeutic agents such as rampamycin.

Representative classes of diagnostic materials include paramagnetic molecules, fluorescent compounds, magnetic molecules, and radionuclides. Exemplary materials include, but are not limited to, metal oxides, such as iron oxide, metallic particles, such as gold particles, etc. Biomarkers can also be conjugated to the surface for diagnostic applications.

One or more active agents may be formulated alone or with excipients or encapsulated on, in or incorporated into the nanocarriers. Active agents include therapeutic, prophylactic, neutraceutical and diagnostic agents. Any suitable agent may be used. These include organic compounds, inorganic compounds, proteins, polysaccharides, nucleic acids or other materials that can be incorporated using standard techniques.

Alternatively, vesicles may encapsulate cellular materials, such as for example, cellular materials to be delivered to antigen presenting cells as described below to induce immunological responses.

Prophylactics can include compounds alleviating swelling, reducing radiation damage, and anti-inflammatories.

Exemplary agents for imaging including radioactive materials, fluorescent label, and contrast agents are discussed above.

Active agents can be selected based on the type of treatment being employed. Exemplary active agents for treating cancer, ischemia, and injury.

Active agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and nucleic acids), and biologically active portions thereof. Suitable active agents have a size greater than about 1,000 Da for small peptides and polypeptides, more typically at least about 5,000 Da and often 10,000 Da or more for proteins. Nucleic acids are more typically listed in terms of base pairs or bases (collectively "bp"). Nucleic acids with lengths above about 10 bp are typically used in the present method. More typically, useful lengths of nucleic acids for probing or therapeutic use will be in the range from about 20 bp (probes; inhibitory RNAs, etc.) to tens of thousands of bp for genes and vectors. The active agents may also be hydrophilic molecules, and optionally have a low molecular weight.

Thus, in some embodiments, the active agent can be a functional nucleic acid. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

a. Functional Nucleic Acids i. miRNA

A particularly interesting therapeutic macromolecule to deliver with the disclosed vesicles are microRNAs. They represent a class of non-coding RNAs that can modulate cellular activities on a genetic level. Thus, the functional nucleic acid can be a microRNA (miRNA or miRs) molecule. miRNAs represent a class of small, 18- to 28-nucleotide-long, noncoding RNA molecules (Tanase, et al., Molecular Pathology of Pituitary Adenomas, Chapter 8, MicroRNAs, pg. 91-96 (2012)). More than 900 members of the family have been identified in humans. Their major role is in the posttranscriptional regulation of protein expression, and their involvement has been confirmed in normal and in pathological cellular processes including, but not limited to, cell differentiation, cell cycle progression, and apoptosis. miRNAs are "multivalent," with one miRNA able to target multiple genes, thus regulating the expression of several proteins.

miRNAs are generated from large RNA precursors (termed pri-miRNAs) that are processed in the nucleus into approximately 70 nucleotide pre-miRNAs, which fold into imperfect stem-loop structures (Lee, Y., et al., Nature (2003) 425(6956):415-9) doi: 10.1038/nature01957. The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 doi: 10.1126/science.1062961 and Grishok, A., et al., Cell (2001) 106(1):23-34 doi: 10.1016/S0092-8674(01)00431-7). miRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the ribonucleoprotein complex known as the RNA-induced silencing complex (RISC) complex. This mechanism of miRNA-mediated gene silencing has been observed mainly in plants (Hamilton, A. J. and D. C. Baulcombe, Science (1999) 286(5441):950-2 doi: 10.1126/science.286.5441.950 and Reinhart, B. J., et al., miRNAs in plants. Genes and Dev. (2002) 16:1616-1626 doi: 10.1101/gad.1004402), but an example is known from animals (Yekta, S., I. H. Shih, and D. P. Bartel, Science (2004) 304(5670):594-6 doi: 10.1 126/science.1097434). In the second mechanism, miRNAs that bind to imperfect complementary sites on messenger RNA transcripts direct gene regulation at the posttranscriptional level but do not cleave their mRNA targets. MiRNAs identified in both plants and animals use this mechanism to exert translational control of their gene targets (Bartel, D. P., Cell (2004) 116(2):281-97 doi: 10.1016/50092-8674(04)00045-5).

Functional studies have confirmed that miRNA dysregulation is causal in many cases of cancer, with miRNAs acting as tumor suppressors or oncogenes (oncomiRs), and miRNA mimics and molecules targeted at miRNAs (antimiRs) have shown promise in preclinical development. The two approaches can be referred to as miRNA replacement or restoration therapy and miRNA reduction or inhibition therapy. See, e.g., Chakraborty, et al., *Oncotarget,* 9:10164-10174 (2018), doi.org/10.18632/oncotarget.24309, which, along with references cited therein, are specifically incorporated by reference herein their entireties.

miRNA replacement or restoration therapy employs the reuse of miRNAs that are deleted or downregulated in cancers. For example, miR-15a and miR-16-1 have been shown induce apoptosis, block proliferation and control prostate cancer by targeting numerous oncogenic activities. Systemic delivery of tumor suppressor miRNAs using miR-34a and let-7 decreased the tumor load in a KRAS (K-ras; a proto-oncogene)-activated non-small cell lung cancer mouse model. Systemic delivery of tumor suppressor miR-34a and miR-16 repressed the development of prostate and colon cancer and let-7a in a KRAS mutant mouse model controlled the growth of lung cancer in a xenograft mouse model or murine lung tumor model. MRX34 is a liposome-based miR-34 mimic that can be intravenously injected, and is under investigation for treatment of advanced hepatocellular carcinoma patients.

miRNA reduction or inhibition therapy can inactivate those miRNAs that are overexpressed or upregulated in cancers, especially in tumors. Several miRNA inhibitory agents have been studied over time. Some are locked nucleic acid or LNA, antisense anti-miR oligonucleotides, small molecule inhibitors of miRNAs, and miRNA sponges.

Locked nucleic acids (LNA)-anti-miR intravenous injections were shown to block miR-122 and miR92a-3p. LNA inhibition of miR92a-3p encouraged apoptosis and stoped cell propagation in human acute leukemia. Commercial LNA-anti-miR-122 is being tested in clinical trials to manage hepatitis C virus (HCV). Several small molecules have also been reported to inhibit miRNAs including miR-21, which over expressed in different types of human cancers and HeLa cells. miRNA sponges antagonize miRNA, which has RNA transcripts with multiple tandem repeats. It has been noted that sponge RNAs enclose binding sites opposite to a miRNA. A long non-coding RNA (lncRNA), lncRNA H19, was also shown to act as miRNA sponges in colorectal cancer Naro, et al., Bioorg Med Chem Lett., 25:4793-96 (2015), doi.org/10.1016/j.bmcl.2015.07.016 PMID: 26220158, and a miRNA sponge was shown to hinder miR-9 in extremely malignant cells. This sponge is used in the pulmonary micro-metastasis in murine models, which slows metastasis development. miR-9 intensity is linked to MYCN amplification, metastatic status and tumor ranking (Ma, et al., Nat Cell Biol., 12:247-56 (2010)).

Other targets include miR-205, miR-129, and miR-145.

Combination therapy with miRNA along with a chemotherapeutic agent for the treatment of cancer have also been reported:

miR-205+gemcitabine used to treat the pancreatic cancer. It inhibited tumor growth in gemcitabine resistant pancreatic cancer cells (MIA PaCa-2(R) and CAPAN-1(R) cells).

miR-34a+paclitaxel used to treat cancers where miR-34a was integrated jointly with paclitaxel into solid lipid nanoparticles (miSLNs-34a/PTX).

miR-34a+doxorubicin inhibited prostate cancer metastasis and progenitor cells. It hindered prostate cancer metastasis through repressing CD44.

miR-129+fluorouracil (5-FU) was used to treat colorectal tumor mouse model.

miR-145+fluorouracil (5-FU) was used to treat both breast cancer cells as well as the breast cancer mouse model.

miR-34a+Docetaxel was used to treat metastatic breast cancer.

See, also e.g., Rupaimoole and Slack, *Nature Reviews Drug Discovery,* 16:203-222 (2017) doi: 10.1038/nrd.2016.246., Zeng, et al., *Methods of Enzymology,* 392: 371-380 (2005) doi: 10.1016/S0076-6879(04)92022-8, and Chakraborty, et al., *Molecular Therapy: Nucleic Acids,* 8:132-143 (2017) doi: 10.1016/j.omtn.2017.06.005, each of which is specifically incorporated by reference herein in its entirety.

Suitable miRNA molecules and other cargo for miRNA regulation for use in the compositions and methods described herein include, but are not limited to, pri-miRNA, pre-miRNA, mature miRNA, miRNA mimics, or fragments or variants thereof that retain the biological activity of the miRNA and DNA encoding a pri-miRNA, pre-miRNA, mature miRNA, miRNA mimic or fragment or variant thereof, or DNA encoding regulatory elements of the miRNA, miRNA sponges, long non-coding RNAs, and small molecules, alone or in combination with other therapeutic agents such as chemotherapeutic drugs.

In some embodiments the nucleic acid encoding the miRNA molecule is on a vector. These vectors include a sequence encoding a mature microRNA and in vivo expression elements. In a preferred embodiment, these vectors include a sequence encoding a pre-miRNA and in vivo expression elements such that the pre-miRNA is expressed and processed in vivo into a mature miRNA. In another embodiment, these vectors include a sequence encoding the pri-miRNA gene and in vivo expression elements. In this embodiment, the primary transcript is first processed to produce the stem-loop precursor miRNA molecule. The stem-loop precursor is then processed to produce the mature microRNA. Vectors include, but are not limited to, plasmids, cosmids, phagemids, viruses, other vesicles derived from viral or bacterial sources that have been manipulated by the insertion or incorporation of the nucleic acid sequences for producing the microRNA, and free nucleic acid fragments which can be attached to these nucleic acid sequences.

miRNA sequences are known in the art available at miRBase, some accession numbers for which are provided herein and expressly incorporated by reference in their entireties.

Exemplary miRNA sequences that can be used as cargo, or to create miRNA expression constructs, include those used in the experiments below and others including, but not limited to:

```
miR-489-3p:
                                        (SEQ ID NO: 1)
GUGACAUCACAUAUACGGCAGC.

miR-21-5p:
                                        (SEQ ID NO: 2)
UAGCUUAUCAGACUGAUGUUGA

miR-298-5p:
                                        (SEQ ID NO: 3)
GGCAGAGGAGGGCUGUUCUUCCC

miR-298:
                                        (SEQ ID NO: 4)
AGCAGAAGCAGGGAGGUUCUCCCA

miR-101:
                                        (SEQ ID NO: 5)
CAGUUAUCACAGUGCUGAUGCU.
```

Another miRNA cargo is miRNA Hsa-miR-26a-5p. miRNA Hsa-miR-26a-5p has a strong effect on cancer metastasis and growth by reducing cancer cell proliferation and cell death.

ii. Antisense

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

iii. Aptamers

The functional nucleic acids can be aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$ M, $10^{-8}$, $10^{-10}$, or $10^{-12}$ M. Aptamers can bind the target molecule with a very high degree of specificity and affinity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower (or higher affinity) than the $K_d$ with a background binding molecule. It is preferred when doing the comparison for a molecule such as a polypeptide, that the background molecule be a different polypeptide.

iv. Ribozymes

The functional nucleic acids can be ribozymes. Ribozymes are functional nucleic acid molecules that are capable of catalyzing a chemical reaction, either intramolecularly or intermolecularly. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for targeting specific sites on nucleic acids for cleavage because recognition of the target substrate is based on the target substrates sequence.

v. Triplex Forming Oligonucleotides

The functional nucleic acids can be triplex forming molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$ M.

vi. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

vii. RNA Interference

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11 doi: 10.1038/35888; Napoli, et al. (1990) Plant Cell 2:279-89 doi: 10.1105/tpc.2.4.279; Hannon, (2002) Nature, 418:244-51 doi:10.1038/418244a). Once dsRNA enters a cell, it is cleaved by an RNase III-like enzyme, Dicer, into double stranded short interfering RNAs (siRNA) 21-23 nucleotides in length that contains 2 nucleotide overhangs on the 3' ends (Elbashir, et al. (2001) Genes Dev., 15:188-200 doi: 10.1101/gad.862301; Bernstein, et al. (2001) Nature, 409: 363-6 doi: 10.1038/35053110; Hammond, et al. (2000) Nature, 404:293-6 doi: 10.1038/35005107). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21 doi: 10.1016/50092-8674(01)00547-5). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74 doi: 10.1016/50092-8674(02)00908-X). However, the effect of miRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498 doi:10.1016/S0248-4900(03)00079-0) (Ui-Tei, et al. (2000) FEBS Lett 479:79-82 doi: 10.1016/S0014-5793(00)01883-4). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER@siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

In some embodiment, the functional nucleic acid is siRNA, shRNA, miRNA. In some embodiments, the composition includes a vector expressing the functional nucleic acid. Methods of making and using vectors for in vivo expression of functional nucleic acids such as antisense oligonucleotides, siRNA, shRNA, miRNA, EGSs, ribozymes, and aptamers are known in the art.

viii. Other Gene Editing Compositions

In some embodiments the functional nucleic acids are gene editing compositions. Gene editing compositions can include nucleic acids that encode an element or elements that induce a single or a double strand break in the target cell's genome, and optionally a polynucleotide.

1. Strand Break Inducing Elements

CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) doi: 10.1126/science.1231143. and Jinek, et al., *Science,* 337 (6096):816-21 (2012)) doi: 10.1 126/science.1225829. By transfecting a cell with the required elements including a Cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) doi: 10.1126/science.1231143. and Jinek, et al., *Science,* 337(6096):816-21 (2012)) doi: 10.1126/science.1225829. A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, CRISPRs web server (crispr.i2bc.paris-saclay.fr/), a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate CRISPR-associated (Cas) enzyme from the same or separate plasmids in transfected cells results in a single or double strand break (depending of the activity of the Cas enzyme) at the desired target site.

Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fokl. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279 doi: 10.1073/pnas.89.13.5847; Li et al. *Proc. Natl. Acad. Sci. USA,* 90:2764-2768 (1993) doi: 10.1073/pnas.90.7.2764; Kim et al. *Proc. Natl. Acad. Sci. USA.* 91:883-887 (1994) doi: 10.1073/pnas.91.3.883; Kim et al. *J. Biol. Chem.* 269 (50): 31978-31982 (1994) PMID: 7989374. One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The Cys2His2 domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering transcription activator-like (TAL) to bind to specific nucleic acids are described in Cermak, et al, *Nucl. Acids Res.* 1-11 (2011) doi: 10.1093/nar/gkr218. US Published Application No. 2011/0145940, which discloses TAL effectors and methods of using them to modify DNA. Miller et al. *Nature Biotechnol* 29: 143 (2011) doi: 10.1038/nbt.1755 reported making TALENs for site-specific nuclease architecture by linking TAL truncation variants to the catalytic domain of Fokl nuclease. The resulting TALENs were shown to induce gene modification in immortalized human cells. General design principles for TALEN binding domains can be found in the patent titled, "Tal Effector-mediated DNA Modification (WO 2011/072246)" for example.

2. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair (HDR) can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

b. Nucleic Acid Composition

The functional nucleic acids can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the nucleic acids are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA nucleic acids of the same nucleobase sequence. For example, the nucleic acid can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the nucleic acid analog molecule and bases in a standard polynucleotide (e.g., single-stranded RNA or single-stranded DNA). In some embodiments, the analogs have a substantially uncharged, phosphorus containing backbone.

i. Heterocyclic Bases

The principal naturally-occurring nucleotides include uracil (U), thymine (T), cytosine (C), adenine (A) and guanine (G) as the heterocyclic bases. The nucleic acids can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives.

ii. Sugar Modifications

Nucleic acids can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-0,4'-C-methylene, 2'-O-(methoxyethyl) (2'-OME) and 2'-O-(N-(methyl)acetamido) (2'-OMA). 2'-O-aminoethyl sugar moiety substitutions are especially preferred because they are protonated at neutral pH and thus suppress the charge repulsion between the triplex forming oligonucleotide (TFO) and the target duplex. This modification stabilizes the C3'-endo conformation of the ribose or dexyribose and also forms a bridge with the i-1 phosphate in the purine strand of the duplex.

In some embodiments, the functional nucleic acid is a morpholino nucleic acid. Morpholino nucleic acids are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, nucleic acids employ morpholino-based subunits bearing base-pairing moieties, joined by uncharged linkages, as described above.

iii. Internucleotide Linkages

Nucleic acids connected by an internucleotide bond that refers to a chemical linkage between two nucleoside moieties. Modifications to the phosphate backbone of DNA or RNA nucleic acids may increase the binding affinity or stability nucleic acids, or reduce the susceptibility of nucleic acids nuclease digestion. Cationic modifications, including, but not limited to, diethyl-ethylenediamide (DEED) or dimethyl-aminopropylamine (DMAP) may be especially useful due to decrease electrostatic repulsion between the nucleic acid and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Nucleic acids containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g. Verma et al., *Annual Review of Biochemistry,* 67(1): 99-134 doi: 10.1 146/annurev.biochem.67.1.99), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the nucleic acids are composed of locked nucleic acids. Locked nucleic acids (LNA) are modified RNA nucleotides (see, for example, Braasch, et al., *Chem. Biol.,* 8(1):1-7 (2001) doi: 10.1016/S1074-5521(00) 00058-2). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the nucleic acids are composed of peptide nucleic acids. Peptide nucleic acids (PNAs) are synthetic DNA mimics in which the phosphate backbone of the nucleic acid is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA nucleic acids, but are achiral and neutrally charged molecules. Peptide nucleic acids are comprised of peptide nucleic acid monomers.

Other backbone modifications include peptide and amino acid variations and modifications. Thus, the backbone constituents of nucleic acids such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Nucleic acids optionally include one or more terminal residues or modifications at either or both termini to increase stability, and/or affinity of the nucleic acid for its target. Commonly used positively charged moieties include the amino acids lysine and arginine, although other positively charged moieties may also be useful. Nucleic acids may be end capped to prevent degradation using a propylamine group. Procedures for 3' or 5' capping nucleic acids are well known in the art.

In some embodiments, the functional nucleic acid can be single stranded or double stranded.

III. Methods of Making Functionalized Vesicles

Nano-based delivery systems have been developed to deliver a wide range of molecules, including drugs, nucleotides, and proteins [1]. Several nano-based delivery systems are available, including liposomes, dendrimers, and carbon nanotubes [2]. To be effective in vivo carriers, they are designed to be biodegradable, biocompatible, and non-immunogenic [3-5]. Ideal nano-based delivery systems must overcome many challenges, including rapid clearance, instability, toxicity, and inefficient targeting [5-7].

One of the major nano-based delivery systems that has been recently designed from naturally occurring vesicles called extravascular vesicles (EVs) or artificially-produced liposomal nanoparticles (LNPs) [e.g., 8,9]. EVs average in size around 100 nm and are excreted from various body fluids such as blood and urine. LNPs can be made in a range of sizes through a variety of techniques [e.g., 9,10]. EVs are formed by inward budding of the plasma membrane with other surface membrane invaginations from the Golgi apparatus [10]. These play an important role in cell-to-cell communication and naturally carry RNA and proteins as their internal cargo [10]. EVs are advantageous because these vesicles have a lot of potential for macromolecular delivery because of their inherent biocompatibility, long-circulating half-life, low toxicity, and tendency to be endocytosed into target tissues [11]. LNPs have a lot of therapeutic potential as well because they can be designed with improved biocompatibility, they can be stored lyophilized for long periods of time and produced on an industrial scale [12,13].

Artificial and natural functionalized vesicles have been accomplished using relatively simple methods [14,15]. EVs have been covered with antibodies against the surface CD9 protein and had improved delivery of miRNA to effector T-cells [14] but seems limited to transfer between T-cells. A traditional approach, which can be called the "Detergent-Dialysis Method," uses detergent and dialysis to produce functionalized vesicles [16-23]. One of the key differences of this approach to that of the preferred approaches described herein is that all the components are completely detergent solubilized and extensive dialysis is required for detergent removal [16-23]. This approach disrupts the original structure of the vesicle by detergent solubilization [16-23]. The approach is also very time consuming because of the extensive dialysis and often column chromatography that are required to remove contaminants [16-23]. Recently, a two-stage process for producing mEVs was developed where the EVs are PEGylated and attached with antibodies [15]. The three-day process has potential for industrial scale-up but requires the mEVs to undergo large temperature fluctuations between 4° C. and 40° C. that may destabilize constitutive proteins and antibodies (Abs) [15,24,25].

A potential therapeutic cargo for functionalized vesicles is microRNA (miRNA) [26]. These macromolecules are small non-coding polynucleotides that range in length between 17 and 25 nucleotides [27]. They play an important role in physiology by modulating gene expression through binding to mRNA [27]. MiRNAs have been associated with many diseases, including several cardiovascular diseases, several types of cancer, and allergic responses [28]. They can also elicit anticancer drug resistance in cancerous tumors [29]. Their presence has been exploited as biomarkers of various diseases [28]. Their ability to modulate genetic expression has a lot of therapeutic potential [26]. These miRNA therapeutics can be divided into either synthetic mimics or inhibitors that are called anti-miRs [26]. They have also been chemically modified to reduce degradation and improve their therapeutic efficacy [26]. To reduce degradation and improve delivery, these macromolecules have been delivered by liposomes, dendrimers, and polymers [26]. Currently, several miRNA therapeutics are going through clinical trials to treat cancer and liver disease [26]. Therefore, targeted delivery of miRNA represents an excellent platform to apply the disclosed approach.

Described herein is, a simpler, less time-consuming and a gentler approach for producing functionalized vesicles (a.k.a. derivatized vesicles) also referred to as "Functionalized Lipid Insert Method" to differentiate it from the "Dialysis-Detergent Method." The functionalized vesicles can be produced in half the time of [15] and at a constant temperature (4° C.) where vesicles, proteins, and Abs are stable [24,25,30]. The disclosed approach has relatively high surface Ab concentration that is 700-fold higher than other methods [15]. Functionalized vesicles with the disclosed approach can be made with any targeting ligand or protein, including antibodies and affibodies. Therefore, they have the potential to target any cell, tissue, or organ.

The "Detergent-Dialysis Method" versus the "Functionalized Lipid Insertion Method"

The disclosed method of producing functionalized vesicles involving detergent and dialysis also referred to herein as "Functionalized Lipid Insertion Method" is distinct from the "Detergent-Dialysis Method" that has been described elsewhere [16-23].

To differentiate the two approaches, they are shown schematically in FIGS. 7A-7D. A key feature of the "Detergent-Dialysis Method" (FIGS. 7A-7B) is that all the components of the functionalized vesicle (i.e., lipids, proteins, functionalized lipids (a.k.a. derivatized lipids), etc.) are all detergent solubilized at several times above the critical micelle concentration (CMC) (Step 1) [e.g., 16,23]. Because of the relatively high detergent concentration, the mixture must be extensively dialyzed over many hours or days (Step 2). The dialysis eventually removes most of the detergent, and vesicles begin stochastically forming from the lipids and the functionalized lipids that are present. The size of the functionalized vesicles likely depends on the composition of the original components. Due to the stochastic nature of vesicle formation, the functionalized lipids will be randomly oriented toward the inside and the outside of the vesicle (denoted by arrows near Step 3). However, even the long dialysis period is often not enough to remove all the detergent, and the detergent-solubilized functionalized lipid. Therefore, column chromatography is often used in addition to dialysis to remove the remaining contaminants (Step 3) [e.g., 16].

Figures 7A, 7B, 7C, 7D:
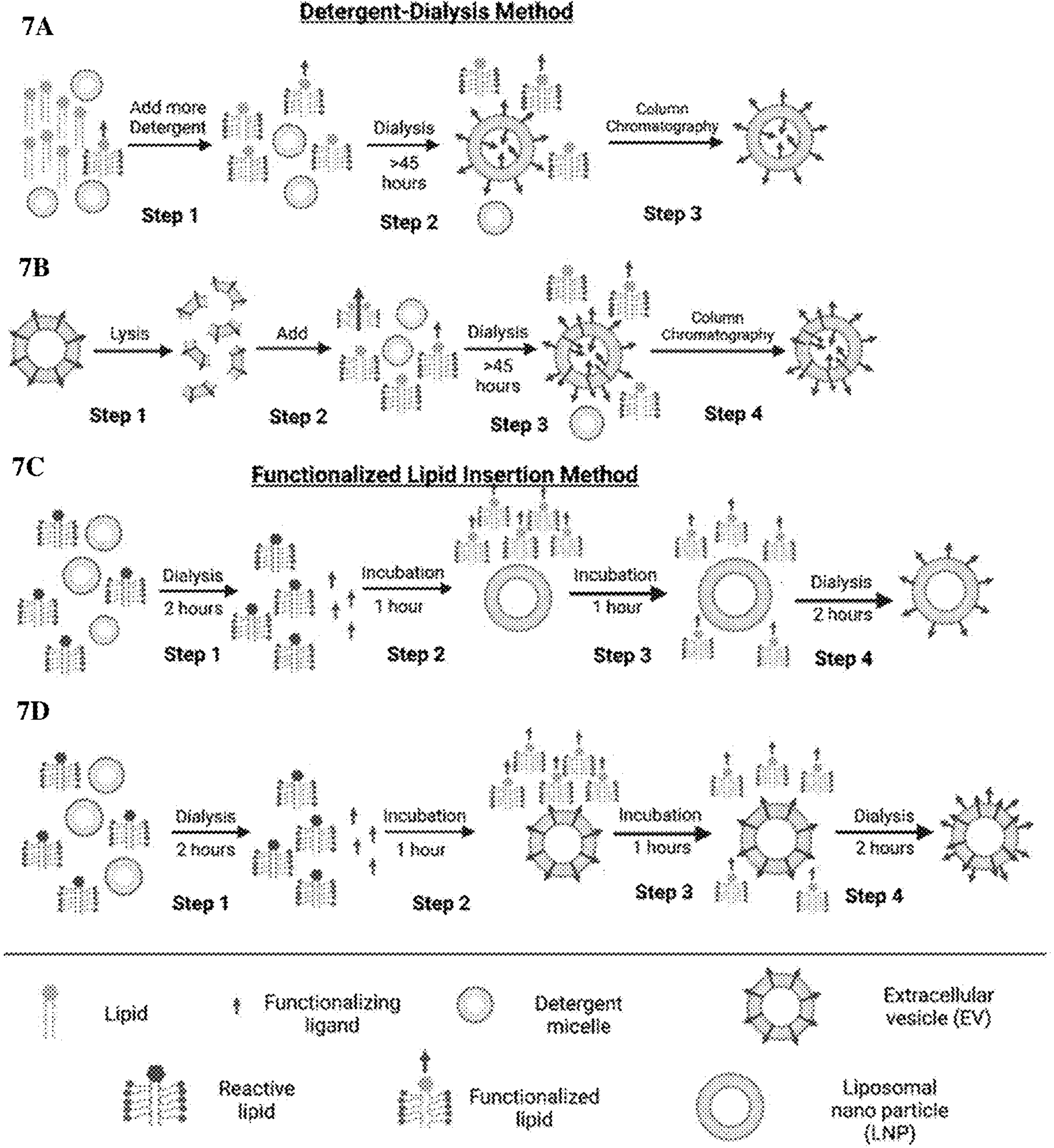
FIGS. 7A-7D are flow diagrams illustrating the bioengineering of mEVs and mLNPs by the "Detergent-Dialysis Method" and the "Functionalized-Lipid Method" as utilized in the comparative experiments of the working Examples.

FIG. 7B shows the production of an mEV by the "Detergent-Dialysis Method." A natural vesicle like an EV is lysed into its individual components like described [18](Step 1)

disrupting its natural structure. The natural vesicle components (e.g., lipid and proteins) and the functionalized lipid are solubilized with detergents at several times the CMC concentration (Step 2). This is followed by a long period of dialysis (Step 3) and often involves column chromatography to remove contaminants (Step 4). Because of the stochastic nature of functional mEV formation, both proteins (arrows) and functionalized lipids (arrows) assume random orientations within the vesicle. Randomly orienting proteins in these functionalized vesicles will likely disrupt their natural function. For example, an outward-facing protein is now an inward-facing protein.

An exemplary "Functionalized Lipid Insertion Method" protocol of the disclosure is shown in FIGS. 7C-7D. For both mLNPs and mEVs, a reactive lipid (e.g., DPSE-PEG2000-Maliemide) is solubilized by detergent and dialyzed for a shorter period, e.g., about two hours, to remove excess detergent (Step 1). The purpose of eliminating the excess detergent by the first dialysis is to prevent the excess detergent from solubilizing components of the natural or artificial vesicle. A detergent-solubilized reactive lipid is incubated for, e.g., about 1 hour with an excess of a functional component like an antibody (Ab) (Step 2). Afterward, the functionalized lipid is incubated for e.g., another about one hour with a preformed artificial vesicle-like an LNP or a natural vesicle-like an EV (Step 3). This incubation period will allow the components to mix, but without external perturbation (like sonication) that might disrupt the vesicles. Finally, the detergent bound to the functionalized lipid is removed by e.g., 2 hours of dialysis (Step 4). Because there is a lot less detergent to remove, the dialysis period is significantly shortened, and column chromatography is not needed afterward. Also, the relatively low detergent concentration ensures that there is very little excess detergent to disrupt the original vesicle. Detergent removal from the functionalized lipid exposes hydrophobic parts of the molecule and entropically drives the lipid into the preformed vesicle forming the functionalized vesicle with the functionalized part of the lipid (arrows) facing outward (Step 4). Membrane proteins can be oriented using a similar approach [52,53].

A. Sources of Vesicles

1. Methods of Isolating Naturally-Occurring Vesicles

Methods of isolating extracellular vesicles from tissue, cells, and fluid directly from a subject, including cultured and uncultured tissue, cells, or fluids, and fluid derived or conditioned by cultured cells (e.g., conditioned media) are known in the art.

See, for example, Li, *Thernaostics,* 7(3):789-804 (2017) doi: 10.7150/thno.18133, Ha, et al., *Acta Pharmaceutica Sinica B,* 6(4):287-296 (2016) doi: 10.1016/j.apsb.2016.02.001, Skotland, et al., *Progress in Lipid Research,* 66:30-41 (2017) doi: 10.1016/j.plipres.2017.03.001, Phinney and Pittenger, *Stem Cells,* 35:851-858 (2017) doi: 10.1002/stem.2575, each of which is specifically incorporated by reference, and describes of isolating extracellular vesicles, particularly exosomes.

For example, extracellular vesicles, particularly exosomes, can be isolated using differential centrifugation, flotation density gradient centrifugation, filtration, high performance liquid chromatography, and immunoaffinity-capture.

One of the most common isolation technique for isolating exosomes from cell culture is differential centrifugation, whereby large particles and cell debris in the culture medium are separated using centrifugal force between 200-100,000×g and the exosomes are separated from supernatant by the sedimenting exosomes at 100,000×g. Purity can be improved, however, by centrifuging the samples using flotation density gradient centrifugation with sucrose or Optiprep. Tangential flow filtration combined with deuterium/sucrose-based density gradient ultracentrifugation was employed to isolate therapeutic exosomes for clinical trials.

Ultrafiltration and high performance liquid chromatography (HPLC) are additional methods of isolating exosomes based on their size differences. Exosomes prepared by HPLC are highly purified.

Hydrostatic filtration dialysis has been used for isolating extracellular vesicles from urine.

Another common technique for exosome isolation is a monoclonal antibody-based method. Antibodies against exosome-associated antigens-such as cluster of differentiation (CD) molecules CD63, CD81, CD82, CD9, epithelial cell adhesion molecule (EpCAM), and Ras-related protein (Rab5)—are used for affinity-based separation. The antibodies can be immobilized in different media conditions and combined with magnetic beads, chromatographic matrix, plates, and microfluidic devices for separation. Non-exosomes vesicles that carry the antigens also bind to the antibody, and may also be isolated in this way.

Microfluidics-based devices have also been used to rapidly and efficiently isolate exosomes, tapping on both the physical and biochemical properties of exosomes at microscales. In addition to size, density, and immunoaffinity, sorting mechanisms such as acoustic, electrophoretic and electromagnetic manipulations can be implemented.

Methods of characterizing exosomes are also known in the art. Exosomes can be characterized based on their size, protein content, and lipid content. Exosomes are sphere-shaped structures with sizes between 40-100 nm and are much smaller compared to other systems, such as a microvesicle, which has a size range from 100-500 nm. Several methods can be used to characterize exosomes, including flow cytometry, nanoparticle tracking analysis, dynamic light scattering, western blot, mass spectrometry, and microscopy techniques. Exosomes can also be characterized and marked based on their protein compositions, with integrins and tetraspanins being the two most abundant proteins found in exosomes. Other protein markers include TSG101, ALG-2 interacting protein X (ALIX), flotillin 1, and cell adhesion molecules. Similar to proteins, lipids are major components of exosomes and can be utilized to characterize them.

An advantage of utilizing vesicles such as exosome that are isolated from natural sources includes avoidance of immunogenicity that can be associated with artificially produced lipid vesicles.

In some embodiments, the vesicles are isolated from cells, tissue, or fluid of the subject to be treated. Vesicles obtained in this manner, for example from human blood, and can thus be used for personalized medicine with a patient's own lipid-based vesicles after they are functionalized. Other promising sources include, for example, immune cells and stromal cells.

2. Methods of Making Synthetic and Artificial Vesicles

Methods of making liposomes and niosomes are also known in the art. Liposomes typically have an aqueous core. The aqueous core can contain water or a mixture of water and alcohol. Suitable alcohols include, but are not limited to, methanol, ethanol, propanol, (such as isopropanol), butanol (such as n-butanol, isobutene, sec-butanol, tart-butanol, pentane (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The liposomes have either one or several aqueous compartments delineated by either one (unilamellar) or several (multilamellar) phospholipid bilayers (Sapra, et al., *Curr. Drug Deliv.,* 2, 369-81 (2005) doi: 10.2174/156720105774370159). Multilamellar liposomes have more lipid bilayers for hydrophobic therapeutic agents to associate with. Thus, potentially greater amounts of therapeutic agent are available within the liposome to reach the target cell.

Depending on the mode of preparation, the size and the degree of lamellarity of the vesicles can be tuned. Several methods for preparing unilamellar lipidic vesicles have been described in the literature: reverse phase evaporation (Szoka et al., PNAS, 1978; 75(9):4191-4198 doi: 0.1073/pnas.75.9.4194), ethanol injection (Pons et al. *International Journal of Pharmaceutics,* 1993; 95(1-3):51-56 doi: 10.1016/0378-5173(93)90389-W), heating method (Mozafari et al., *Journal of Biotechnology,* 2007; 129:604-613 doi: 10.1016/j.jbiotec.2007.02.005), but the most simple is the lipid film hydration method (Bangham et al., J. Mol. Bio., 1965; 13:238-252 doi: 10.1016/S0022-2836(65)80093-6).

Briefly, in the lipid film hydration method, lipids are solubilized in an organic solvent such as chloroform. After homogenization of the solution, the organic solvent is evaporated under a nitrogen stream. The as-obtained dried lipid film is then hydrated by an aqueous medium at a temperature above the main phase transition temperature $T_m$, leading to the formation of multilamellar vesicles with sizes ranging from 100 to 800 nm (Mills J. K. et al. Methods in Enzymology 2004; 387:82-113 doi: 10.1016/S0076-6879(04)87006-X). Cycles of dehydration and rehydration, by respectively freezing (in liquid nitrogen) and thawing the solution (at a temperature above $T_m$), allow increasing the aqueous internal volume by forming unilamellar vesicles. A process allowing vesicles size calibration can be applied to obtain a homogeneous size distribution. Sonication produces Small Unilamellar Vesicles (SUV) with size ranging from 20 to 50 nm, whereas extrusion process through a filter membrane produces LUVs with size ranging from 50 to 500 nm depending on the size of the filter pores. Both processes, sonication and extrusion, are performed at a temperature above $T_m$.

Niosomes can be prepared by various methods, many of which are similar to preparing their liposomal counterparts, including, but not limited to ether injection method (EIM), hand shaking method (HSM), reverse phase evaporation method (REV), trans membrane pH gradient, the "Bubble" method, microfluidization method, formation of niosomes from proniosomes, thin-film hydration method (TFH), heating method (HM), freeze and thaw method (FAT), and dehydration rehydration method (DRM) (Moghassemi and Hadjizadeh, *J. Contr. Release,* 185:22-36 (2014)).

See also Akbarzadeh, et al., "Liposome: classification, preparation, and applications," *Nanoscale Research Letters* 8:102 (2013), 9 pages, which is specifically incorporated by reference herein in it entirety.

Results show, and are exemplified below, that an additional valve to the liposome extruder setup can be utilized to produce liposomes of a consistent size with an average 250 nm diameter.

B. Methods of Making Lipid Conjugates

The disclosed conjugates can be made using any suitable means, including through cross-linking reactions. Conjugation of proteins, peptides, nucleic acids, and small molecules are known in the art (see, e.g., "Conjugation of Proteins, Peptides, & Drugs to Liposomes," by Anvanti Polar Lipids, Inc.).

Common examples include, but are not limited to, amide conjugation, disulfide/theioether conjugation, and coupling systems such as biotin/streptavidin binding.

Amide Conjugation: phospholipids with either amine or carboxyl functional groups, for example, carboxyacyl derivatives of phosphatidylethanolamine (PE) can be used for conjugation with proteins/peptides, or drugs containing amine, carboxyl, or hydroxy groups.

Various acyl chain lengths, including, but not limited to those ranging from 4 to 22 carbons, and can be utilized.

Disulfide/Thioether Conjugation: Lipids including, but not limited to, 1,2-dioleoyl-sn-glycero-3-phosphoethanolamine-N-[3-(2-pyridyldithio)propionate](PDP-PE) and 1,2-dioleoyl-sn-glycero-3-phosphoethanolamine-N-[4-(p-maleimidophenyl)butyramide](MPB-PE) or 1,2-dioleoyl-sn-glycero-3-phosphoethanolamine-N-[4-(p-maleimidomethyl)cyclohexane-carboxamide](MCC-PE) can be used for disulfide or thioether based conjugation of thio-containing proteins or peptides.

Maleimide-containing lipids, including, but not limited to, MPB-PE, can also be used. For example, the experiments below utilized a lipid including a maleimide. Maleimide is a reactive group that irreversibly reacts with sulfhydryl groups on proteins linking whatever the maleimide group is attached. This is a well-known crosslinking reaction. Lipids having a terminal maleimide are commercially available and can be used with any polypeptide having at least one sulfhydryl (e.g., a cysteine), such as an antibody, to form a lipid-polypeptide conjugated through thioether bond. 1,2-disteroyl-sn-glycero-3-phosphoethanolamine-N-[maleimide (polyethylene glycol)-2000], DSPE-2000 was used as a substrate for antibody conjugation.

A comparison of pyridyldithiopropionate (PDP) and maleimidophenylbutyramide (MPB) conjugates showed the MPB formed more stable complexes that survive in serum longer. The maleimidomethylcyclohexane-carboxamide (MCC) contains a more stable maleimide function group toward hydrolysis in aqueous reaction environments, due to the proximity of an aliphatic cyclohexane ring rather than the aromatic phenyl group of MPB.

Any peptide or protein initially lacking the necessary amino acid to facilitate conjugations (e.g., lysine, cysteine, etc.) can be recombinantly modified to add one or more additional amino acids, for example to the N- or C-terminus.

Coupling Systems: The lipid domain and targeting domain can also be linked through a coupling systems. For example, biotinylated lipids can be used and linked to the targeting domain via, for example, streptavidin or neutravidin. The lipids can be linked directly to the biotin, or have a spacer, e.g., a 6-carbon spacer between the biotin and the lipid. Biotin PE has been used for bilayer stabilization, temperature/pH sensitive liposomal drug delivery, tumor imaging, two-dimensional crystallization on lipid bilayers, immobilization of liposomes on gel beads for chromatographic analysis of drug-membrane partitioning, and vivo targeting applications. Other coupling systems include, glutathione-S-transferase/glutathione, maltose binding protein/amylase and maltose binding protein/maltose.

In some embodiments, the lipid conjugate is formed without a coupling system, using, for example, one of the methods described above.

In particular embodiments, synthesis is performed where fatty acids are either conjugated to the N-terminus, or to the side-chain of a lysine or a cysteine. Commonly used fatty acids are: Caprylic acid (C8), Capric acid (C10), Lauric acid (C12), Myristic acid (C14), Palmitic acid (C16) or Stearic acid (C18).

In some embodiments, cholesterol is conjugated to a peptide via an N- or C-terminal inserted cysteine. For this, a cholesterol derivative that has been modified with a cysteine-reactive 2-bromoacetyl moiety can be used. See, for example, Pepscan.

In some embodiments, the lipid is conjugated to a fluorophore. For example, a range of fluorescent and biotinylated analogs of the five naturally occurring lipid classes: phospholipids, sphingolipids (including ceramides), fatty acids, triglycerides and steroids are commercially available. See, e.g., Molecular Probes™ Handbook, A Guide to Fluorescent Probes and Labeling Technologies, 11$^{th}$ Edition (2010), Chapter 13, Probes for Lipids and Membranes.

C. Methods of Introducing Lipid Conjugates into Delivery Vesicles

The function element can be introduced into a lipid delivery vehicle that includes a lipid amenable to its conjugation. In other words, a vesicle such as a liposome includes a lipid having an element (such as those described above), available for a conjugation reaction with a functional element after formation of the vesicle. Alternatively, the functional element can be reacted with the lipid and later used alone or in combination with non-functionalized lipid to form the vesicle. However, these methods have drawbacks and limitations.

First, intermicellar crosslinking can occur. Furthermore, both of these methods present difficulty for vesicles such as exosomes that are naturally-occurring and thus pre-formed in the absence of conjugate.

Lipid conjugates can be introduced into synthetic liposomes and niosomes at the time these vesicles are formed.

Performing crosslinking and introduction of the lipid conjugate in a separate step provides advantages. In this process, the lipid vesicle are made artificially using standard procedures (i.e., liposomes) or purified from natural sources (i.e., exosomes). To functionalize the lipid vesicle, a functionalized lipid (e.g., fatty acid-antibody) is passively inserted into a lipid vesicle through dialysis. This passive insertion approach of labeling the lipid vesicle avoids disrupting the membrane of the lipid vesicle unlike other methods for integrating antibodies such as sonication.

In an exemplary method, lipid that will form the foundation of the lipid-conjugate (e.g., the lipid component of the lipid-conjugate, or a precursor thereof) is suspended in a concentration of detergent near the critical micelle concentration (0.1% DDM), and then dialyzed to remove excess detergent, and encourage formation of stable micelles in solution. The detergent should be one that is suitable for stabilizing the hydrophobic regions of the lipid in a semi-aqueous solution. It will be removed upon formation of the final product.

Next, the lipid that forms the foundation of the lipid-conjugate (e.g., the lipid component, or a precursor thereof) is mixed with a functional element, for example a targeting moiety such as an antibody, under concentrations and conditions suitable for conjugation (e.g., covalent attachment) of the functional element to the lipid component, to form a lipid-conjugate. When the functional element is an antibody, the lipid-conjugate can also be referred to as an antibody-label.

This lipid-conjugate is mixed with pre-formed lipid vesicle, for example exosomes such as those obtained from cultured human peripheral blood mononuclear cells and dialyzed using a suitable dialysis system. The dialyzed product, containing the functionalized lipid-conjugate inserted into the lipid vesicle membrane, is now a functionalized lipid vesicle.

In a more specific embodiment, pegylated lipid (which are commercially available) is resuspended in 0.1% DDM, which is close to the critical micelle concentration, and then dialyzed to remove excess DDM, and encourage formation of stable micelles in solution. The DDM detergent is responsible for stabilizing the hydrophobic regions of the pegylated fatty acid in a semi-aqueous solution, and will be removed upon formation of the final product. Then, the pegylated fatty acid is mixed with antibody at a 2:1 fatty acid: antibody concentration ratio and incubated for 1 h at room temperature, resulting in covalent attachment of antibody to lipid, named the antibody-label or lipid conjugate. This lipid conjugate is mixed with 100-150 uL of pre-formed lipid vesicle obtained from cultured human peripheral blood mononuclear cells and dialyzed using a suitable dialysis system.

For example, in the experiments below, lipid conjugate solution was dialyzed using a Slide-A-Lyzer MINI Dialysis units with a 10,000 Da molecular weight cut-off (Thermo Fisher) against 2 L of 1x PBS for 2 h in a 4° C. cold room to integrate the lipid conjugate into the exosomal membrane and remove any detergent remaining from lipid conjugate preparation from solution. This molecular weight cut-off ensures that the components required to build these functionalized lipid vesicles remain in solution, but excess detergent (e.g., DDM) and buffer can be removed by dialysis to form a functionalized lipid vesicle product.

The described methods can be scaled-up by using a larger dialysis membrane that holds more volume, and using larger quantities of each component to produce large amounts of the final functionalized lipid vesicles. Functional elements, lipids, lipid vehicles, detergents, dialysis membranes and other features can be mixed or substituted, for example, as described herein.

The functionalized lipid vesicles can be precipitated using any suitable means. For example, in some of the experiments below, the antibody-labeled exosomes (referred to as Abi-exosomes) were incubated overnight with Exosome Precipitation Buffer from the Exosome Isolation Kit per manufacturer instructions (Exiqon). The solution was then centrifuged at 50,000 rpm (>250,000 g's) for 1 h at 20° C. to pellet the Abi-exosomes, the supernatant was removed and the final product was resuspended in 1x PBS before the introduction of cargo (e.g., electroporated with miRNA).

In other experiments, the mEV solution was incubated with precipitation buffer B from the Qiagen miRCURY Exosome Isolation Kit for e.g., −12 hours (overnight) at 4° C. mLNPs solution was centrifuged at e.g., 14,000 rpm for 30 minutes to obtain a pellet. To pellet the mEVs, the solution was centrifuged at 104,000 g (30,472 rpm) in a Beckman TLA 110 rotor for one hour at 20° C. in a Beckman TLX ultracentrifuge. The supernatant was carefully removed, and the mLNP/mEV pellet was suspended in isotonic PBS.

In particular embodiments centrifugal force (i.e., rpm, g) can be lowered, e.g., 5-fold, for liposome/Abi-liposome compared to exosome/Abi-exosome preparations. For example, in some of the experiments below, liposome/Abi-liposome preparations were spun in a Thermo Scientific Sorvall Legend 21 (14K RPM, 20K g) from exosome/Abi-exosome isolation (i.e., 104,000 g (30,472 rpm) in a Beckman TLA 110 rotor for 1 h at 20° C. in a Beckman TLX ultracentrifuge.)

In some embodiments, the precipitation incubation is less than 12 hours, e.g., 11, 10, 9, 8, 7, 6, 5, 4, 3, 2, or 1 hour, or less than 1 hours, e.g., 45 min, 30 min, 15 min, 10 min, 5 min, etc.

In some embodiments, the precipitation incubation is completely eliminated, particularly for liposomal preparations, which are can be larger, and thus precipitate more than exosomes. This can be advantageous for in vivo applications, and was utilized in some of the experiments presented below.

Precipitates can also be removed by centrifugation.

In some embodiments, preparations include a slow speed centrifugation and/or filtering prior to administration.

D. Loading with Active Agent

Active agents can be loaded into the lipid vesicles using any suitable means.

The disclosed lipid vesicles most typically have an aqueous solution core surrounded by a hydrophobic membrane, often in the form of a lipid bilayer. Hydrophilic solutes dissolved in the core cannot readily pass through the bilayer. Hydrophobic chemicals associate with the bilayer. The vesicles can thus be loaded with hydrophobic and/or hydrophilic molecules. To deliver the molecules to a site of action, the lipid bilayer can fuse with other bilayers such as the cell membrane or be internalized by endocytosis.

Synthetic vesicles can be loaded with active agent by preparing (i.e., forming) the vesicles in a solution containing the active agent.

Naturally occurring and other pre-formed vesicles can also be loaded with drug. For example, methods of loading drug into pre-formed vesicles including exosomes are known in the art and reviewed in Ha, et al., *Acta Pharmaceutica Sinica B,* 6(4):287-296 (2016) doi: 10.1016/j.apsb.2016.02.001, and discussed in Yang, et al., *J Control Release,* 243:160-171 (2016). doi: 10.1016/j.jconrel.2016.10.008. Briefly, small molecules have been loaded by mixing and incubation and through complexation with, for example, surface elements. Proteins and peptides have been loaded by incubation, with or without a permeabilizer such as saponin, through freeze-thaw cycling, sonication, and extrusion procedures. Nucleic acids have been load by chemical transfection and electroporation. See also Table 2 of Ha, et al., *Acta Pharmaceutica Sinica B,* 6(4):287-296 (2016) doi: 10.1016/j.apsb.2016.02.001, and the references cited therein.

Figure 3A:
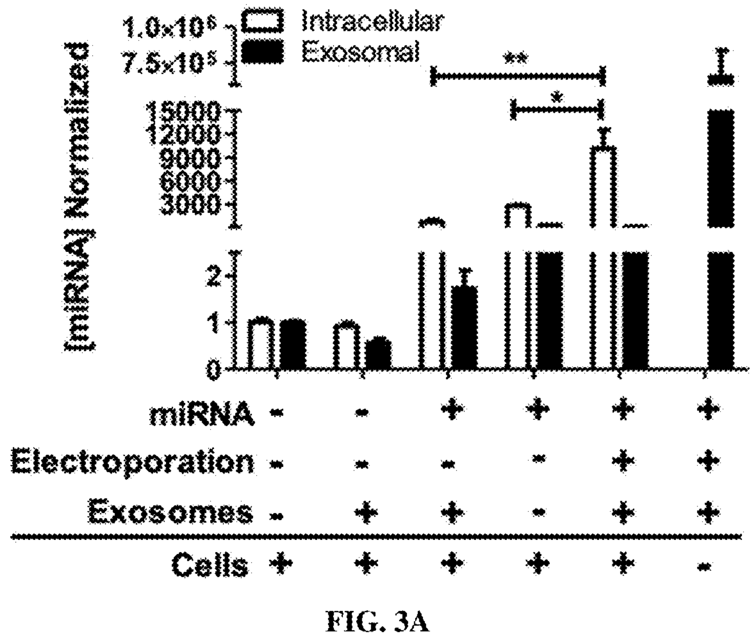
FIG. 3A is a bar graph showing the effect of electroporation on miRNA levels in exosomes as well as delivery into cells compared to standard protocol of transfection, or incubation of miRNA with exosomes without electroporation. Electroporation of miRNA into exosomes can result in 700,000-fold higher miRNA levels in the exosomes compared to purified exosomes. This in turn results in higher miRNA uptake efficiency into cells as well compared to transfection (miRNA alone) (*p<0.05) or miRNA incubated with exosomes without electroporation (**p<0.01).

In a particular preferred embodiment, nucleic acid active agents, such as miRNA, are loaded by electroporation. In electroporation experiments, Bio-Rad Gene Pulser X-Cell CE was used to electroporate miRNA in an exponential decay model into the exosomes at 150 Volts, 125 μF of capacitance for 10-15 microseconds in a 4 mm cuvette, which were subsequently incubated at room temperature for 30 min prior to treating cells. With these parameters, there is a 700,000-fold higher internalization of the macromolecule microRNA (miRNA) into exosomes (FIG. 3A, last column).

In some embodiments, the incubation is for 60 min prior to treating. In more specific examples, the incubation is for about 30 minutes at room temperature and about 30 minutes at 4 degrees Celsius. Experiments indicate that increased internalization of miRNA occurs in both exosome and liposome vehicles when incubated for 1 hour (first 30 minutes at ambient temperature (10-25° C., and the second 30 minutes at 4° C.) versus only 30 minutes (e.g., at ambient temperature) after electroporation.

Results also show that an additional mixing step after electroporation can be used to reduce or eliminate precipitation, particularly for liposome/Abi-liposome preparations. The mixing can be carried out with, for example, a pipette.

IV. Pharmaceutical Compositions

Pharmaceutical compositions including for lipid based vesicles are also provided. Pharmaceutical compositions can be for administration by parenteral (intramuscular (IM), intraperitoneal (IP), intravenous (IV) or subcutaneous injection (SubQ)), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal and oral.

In certain embodiments, the compositions are administered locally, for example, by injection directly into a site to be treated. For example, in some embodiments such as for the treatment of cancer, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., *Drug Delivery Systems: Fundamentals and Techniques* (Chichester, England: Ellis Horwood Ltd., 1988 ISBN-10: 0895735806), which can effect a sustained release of the drug to the immediate area of the implant.

The liposome compositions can be provided to the cell either directly, such as by contacting it with the cell, or indirectly, such as through the action of any biological process. For example, the vesicles can be formulated in a physiologically acceptable carrier, and injected into a tissue or fluid surrounding the cell.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, dosage levels of 0.001 to 10 mg/kg of body weight daily are administered to mammals. Generally, for intravenous injection or infusion, dosage may be lower. Generally, the total amount of the active agent administered to an individual using the disclosed vesicles can be less than the amount of unassociated active agent that must be administered for the same desired or intended effect and/or may exhibit reduced toxicity.

A. Formulations for Parenteral Administration

In a preferred embodiment the compositions are administered in an aqueous solution, by parenteral injection such as IM, IP, IV or SubQ.

The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents, sterile water, buffered saline of various buffer content (e.g., Tris-HCl, acetate, phosphate) at various pHs and ionic strengths; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacterium retaining filter, by incorporating sterilizing agents into the compositions, by irradiating the compositions, or by heating the compositions.

B. Other Formulations

The compositions can be applied topically. Topical administration can include application to the lungs, nasal, oral (sublingual, buccal), vaginal, or rectal mucosa. These methods of administration can be made effective by formulating the vesicle with transdermal or mucosal transport elements. For transdermal delivery, such elements may include chemical enhancers or physical enhancers such as electroporation or microneedle delivery. For mucosal delivery PEGylation of the vesicle or addition of chitosan or other mucosal permeants or pH protective elements for oral delivery is preferred.

Vesicles such as liposomes can be delivered to the lungs (Taylor and Newton, *Thorax.* 1992 April; 47(4): 257-259 PMID: 1585287). A wide range of mechanical devices designed for pulmonary delivery of therapeutic products can be used, including but not limited to, nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Lipid vesicles such as liposomes have also been formulated for oral delivery (Woodley, Crit Rev Ther Drug Carrier Syst. 1985; 2(1):1-18 PMID: 3913528; Hua, *Front Pharmacol.* 2014; 5: 138 doi: 10.3389/fphar.2014.00138, etc.). Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al., *Biomaterials,* 29(6):703-8 (2008) doi: 10.1016/j.biomaterials.2007.10.026.

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

V. Methods of Use

The lipid vesicles can be used to deliver active agents in vitro and in vivo.

A general theory for the delivery of macromolecules by modified vehicles is that the PEG-linked Ab of functionalized vesicles will attach to a surface receptor or excreted protein of a target cell. The vehicle uptake can occur by fusion or by several endocytosis mechanisms [51]. The specific mechanism of exosomal uptake has not been completely worked out but is likely to be cell-dependent [51].

Figures 8A, 8B:
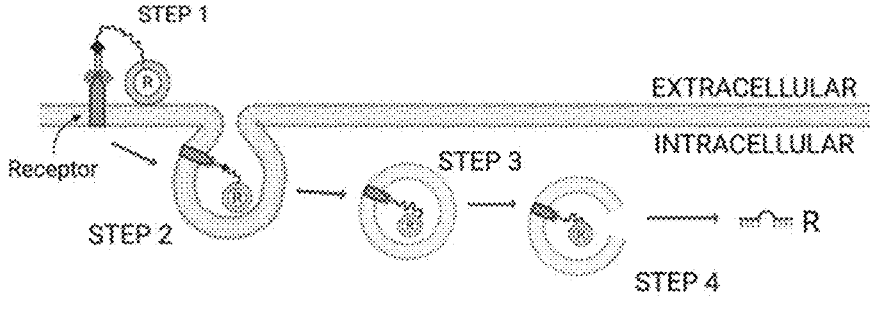
FIGS. 8A-8B are models illustrating the potential mechanisms for cellular endocytosis of functionalized vesicles. A modified vesicle binds to a receptor in Step 1 and then is endocytosed in Step 2. The receptor-bound mEV/mLNP forms a vesicle in Step 3 and disintegrates in Step 4 to release the miRNA (8A). A soluble protein is transferred from the Golgi apparatus to the surface, where it binds to the mEV/mLNP in Step 1 (8B). In order for the soluble protein bound mEV/mLNP to be internalized by a cell, it binds to a surface receptor forming a ternary complex in step 2. In Step 3, the mEV/mLNP is encapsulated into a vesicle. The vesicle disintegrates releasing the miRNA in Step 4. Abbreviations: R, mirNA.

FIGS. 8A-8B shows the potential mechanisms that a modified vesicle can be endocytosed by a target cell. Without providing a specific mechanism, the figure shows the binding of the PEG-linked Ab on the modified vesicle to a receptor on the cell surface (Step 1). The functionalized vesicle binds to the receptor and induces endocytosis. Alternatively, the proximity of the functionalized vesicle to the plasma surface as a result of the PEG linker induces endocytosis (Step 2). Endocytosis of the receptor-bound vesicles leads to an invagination of the cell surface and eventually to the formation of an endosome (Step 3). The endosome disintegrates intracellularly to releases the miRNA inside of the cell (Step 4).

The FIG. 8B shows the targeting of secretory receptor ligands from cells by functionalized vesicles containing microRNA. In Step 1, soluble proteins are trafficked to the Golgi apparatus from the endoplasmic reticulum (ER) [52]. The Golgi apparatus produces secretory vesicles containing the receptor ligands that migrate to the plasma membrane [52]. At the plasma membrane, they are secreted into the extracellular space, where they are bound by a functionalized vesicle (Step 1) [52]. The secreted receptor ligands bind to cell surface receptors forming a ternary complex with the receptor, which can potentially lead to endocytosis (Step 2) [e.g., 53]. Alternatively, if the functionalized vesicle can access the cell surface by the PEG linker, it can also be potentially endocytosed by coming in contact with the plasma membrane. In either case, the functionalized vesicle will form an endosome (Step 3) [51]. The endosome containing the vesicle migrates within the cell (Step 3). Eventually, the endosome and the vesicle disintegrate, releasing the miRNA intracellularly (Step 4).

For example, the disclosed methods of delivery and/or treatment typically include using the disclosed vesicles loaded with one or more active agents, to deliver the one or more active agents into cells, or to a cell's microenvironment. The methods typically include contacting the active agent-loaded vesicle with one more cells. The contacting can occur in vivo or in vitro.

In some embodiments, the vesicles include two or more active agents. For example, using two or more different miRNAs may result in additive target inhibition and subsequent cytotoxic effects of the miRNA in different cell types.

In some embodiments, the vesicles include multiple antibody attachments on vesicles. Having multiple antibodies may assist the functionalized vesicles in navigating the tumor microenvironment to specifically target a cell type overexpressing multiple surface proteins.

A. In vivo Methods

A typical in vivo method of treatment includes administering to a subject in need thereof an effective amount of an active agent-loaded lipid vesicle composition to reduce one or more symptoms of a disease or disorder.

1. Drug delivery

The vesicles can be used to deliver an effective amount of one or more therapeutic, diagnostic, and/or prophylactic agents to an individual in need of such treatment. The amount of agent to be administered can be readily determined by the prescribing physician and is dependent on the age and weight of the patient and the disease or disorder to be treated.

The vesicles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The vesicles may be administered as a dry powder, as an aqueous suspension (in water, saline, buffered saline, etc.), in a hydrogel, organogel, in capsules, tablets, troches, or other standard pharmaceutical excipient As discussed herein, compositions can be used as delivery vehicles for a number of active agents including small molecules, nucleic acids, proteins, and other bioactive agents. The active agent or agents can be encapsulated within, dispersed within, and/or associated with the surface of the vehicles. In some embodiments, the vehicles packages two, three, four, or more different active agents for simultaneous delivery to a cell.

2. Transfection

The disclosed compositions can be for cell transfection of polynucleotides. As discussed in more detail below, the transfection can occur in vitro or in vivo, and can be applied in applications including gene therapy and disease treatment. The compositions can be more efficient, less toxic, or a combination thereof when compared to a control.

The particular polynucleotide delivered by the vesicles can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the vesicles are used to deliver mRNA, siRNA, miRNA, etc., or non-integrating expression vectors that are expressed transiently in the host cell.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Gene targeting via target recombination, such as homologous recombination (HR), is another strategy for gene correction.

In some embodiments, the polynucleotide encodes a protein.

B. Diseases to be Treated

The disclosed compositions can be used to treat a broad range of diseases and disorders including, but not limited to, cancer, infections, genetic disorders, etc. The targeting domain and active agent can be selected based on the disease or disorder to be treated.

For example, in some embodiments, the disclosed compositions and methods of treatment thereof are used for treating cancer, including tumor therapy. The methods typically include administering a subject in need there of an effective amount to the composition to reduce one or more symptoms of cancer. For example, therapeutically effective amounts of the disclosed compositions used in the treatment of cancer will generally kill tumor cells or inhibit proliferation or metastasis of the tumor cells or a combination thereof. Symptoms of cancer may be physical, such as tumor burden, or biological such as apoptosis of cancer cells. For example, the composition can be administered in an amount effective to kill cancer cells, improve survival of a subject with cancer, or a combination thereof. The actual effective amounts of composition can vary according to factors including the specific, the particular composition formulated, the mode of administration, and the age, weight, condition of the subject being treated, as well as the route of administration and the disease or disorder.

An effective amount of the composition can be compared to a control. Suitable controls are known in the art. A typical control is a comparison of a condition or symptom of a subject prior to and after administration of the composition. The condition or symptom can be a biochemical, molecular, physiological, or pathological readout. In another embodiment, the control is a matched subject that is administered a different therapeutic agent. Accordingly, the compositions disclosed here can be compared to other art recognized treatments for the disease or condition to be treated. In a preferred embodiment, the results achieved with a composition including a delivery vehicle and drug is compared to the results achieved by free drug (e.g., drug without delivery vehicle), or with delivery vehicles having or not having a targeting moiety.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way, a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Tumors, for example malignant tumors, which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. Leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterus. In the most preferred embodiments, the cancer is prostate cancer or breast cancer.

In some embodiments, the disclosed compositions are used to treat multiple cancer types concurrently. The compositions can also be used to treat metastases or tumors at multiple locations. For example, breast cancer metastasizes to the brain, bone, liver and lungs, where it would be beneficial to utilize this method.

Exemplary targeting moieties and active agents that can be used in the treatment of cancer are discussed above, and exemplified below.

C. Dosage Regimens

The frequency of administration of a method of treatment can be, for example, one, two, three, four or more times daily, weekly, every two weeks, or monthly. In some embodiments, the composition is administered to a subject once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the frequency of administration is once, twice or three times weekly, or is once, twice or three times every two weeks, or is once, twice or three times every four weeks. In some embodiments, the composition is administered to a subject 1-3 times, preferably 2 times, a week.

D. Combination Therapies

Combination therapies are also disclosed. The disclosed compositions can include, or can be administered to a subject in need thereof alone or in combination with one or more additional therapeutic agents. The additional therapeutic agents are selected based on the condition, disorder or disease to be treated. For example, the lipid vesicles composition can be co-administered with one or more additional agents that treat cancer. In a preferred embodiment the additional therapeutic agent targets a different pathway so that the combined effect of the therapies is greater than each alone.

The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device or graft. The additional agent(s) can be part of the same vesicle, added to different lipid vesicles or other delivery vehicles such as polymeric nanoparticles, or administered as free-drug.

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other anti-tumor agents. All of these drugs affect cell division or DNA synthesis and function in some way. Additional therapeutics include monoclonal antibodies and the new tyrosine kinase inhibitors, e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, irinotecan, leucovorin, liposomal doxorubicin, liposomal daunorubicin, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2), and combinations thereof.

VI. Kits

Dosage units including the disclosed composition, for example, in a pharmaceutically acceptable carrier for shipping and storage and/or administration are also disclosed. Components of the kit may be packaged individually and can be sterile. In some embodiments, a pharmaceutically acceptable carrier containing an effective amount of the composition is shipped and stored in a sterile vial. The sterile vial may contain enough composition for one or more doses. The composition may be shipped and stored in a volume suitable for administration, or may be provided in a concentration that is diluted prior to administration. In another embodiment, a pharmaceutically acceptable carrier containing drug can be shipped and stored in a syringe.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. Any of the kits can include instructions for use.

The disclosed compositions and methods can be further understood through the following numbered paragraphs.

1. A method of making functionalized lipid vesicles comprising a lipid membrane, the method comprising mixing in the presence of detergent lipid vesicles comprising one or more lipids with one or more types of lipid conjugates, each type of lipid conjugate comprising a lipid component and a functional element and dialyzing the mixture for an effective amount of time for the lipid conjugate(s) to insert into the lipid vesicles and form functionalized lipid vesicles.

2. The method of paragraph 1, wherein the lipid conjugate is formed by one or more of the steps of (i) mixing or otherwise suspending the lipid component, or a precursor thereof, in a solution comprising a concentration of detergent near the critical micelle concentration to form a suspension, (ii) dialyzing the suspension to remove excess detergent, and encourage formation of stable micelles in the suspension, (iii) adding, mixing, or otherwise contacting the suspension with the functional element, under conditions suitable for the functional element to conjugate, or otherwise link, to the lipid component to form the lipid conjugate.

3. The method of paragraph 2, wherein the detergent is of a type and amount suitable for stabilizing the hydrophobic regions of the lipid component, or precursor thereof, in a semi-aqueous solution.

4. The method of paragraphs 2 or 3, wherein dialysis of the mixture removes the detergent.

5. The method of any one of paragraphs 1-4, wherein the detergent is n-dodecyl-β-D-maltoside (DDM), optionally at a concentration of about 0.1%.

6. The method of any one of paragraphs 1-5, wherein the lipid vesicle is naturally occurring.

7. The method of any one of paragraphs 1-6, wherein the lipid vesicles are isolated from cultured or uncultured tissue, cells, or fluid.

8. The method of paragraph 7, wherein the fluid derived from, or conditioned by, cultured cells.

9. The method of paragraph 7, wherein the fluid is blood, plasma, lymph liquid, malignant pleural effusion, amniotic liquid, breast milk, semen, saliva or urine.

10. The method of any one of paragraphs 1-9, wherein the lipid vesicles are apoptotic bodies and/or blebs (AB), microvesicles (MV), exosomes, or tunnelling nanotubes (TNT).

11. The method of any one of paragraphs 1-5 wherein the lipid vesicles are synthetic.

12. The method of paragraph 11, wherein the synthetic lipid vesicles are niosomes or liposomes.

13. The method of any one of paragraphs 1-12, wherein the lipid vesicles are between about 30-150 nm.

14. The method of any one of paragraphs 1-13, wherein the functional element is a small molecule, protein or polypeptide, carbohydrate, nucleic acid or a combination thereof.

15. The method of paragraphs 14, wherein the functional element is a targeting moiety that increases attachment, binding, or association of the functionalized lipid vesicle to a target cell(s), tissues(s), and/or microenvironment(s) relative to the lipid vesicle.

16. The method of any one of paragraphs 1-15, wherein the functional element is a targeting moiety that increases attachment, binding, or association of the functionalized lipid vesicle to a target cell(s), tissues(s), and/or microenvironment(s) relative non-targeted cell(s), tissue(s), and/or microenvironment(s).

17. The method of paragraphs 15 or 16, wherein the targeting moiety targets cancer cells.

18. The method of any one of paragraphs 15-17, wherein the targeting moiety targets CD44 or CD29/Integrin beta-1.

19. The method of any one of paragraphs 15-18, wherein the functional element is an antibody.

20. The method of any one of paragraphs 1-19 wherein the functional element comprise or is a detectable label.

21. The method of paragraph 20, wherein the detectable label is a fluorophore, radiolabel, magnetic label, or a contrast agent.

22. The method of any one of paragraphs 1-21 further comprising loading the lipid vesicles or functionalized lipid vesicles with an active agent.

23. The method of paragraph 22, wherein the active agent is selected from therapeutic, nutritional, diagnostic, prophylactic compounds, and combinations thereof.

24. The method of paragraphs 22 or 23, wherein the active agent is a protein, peptide, carbohydrate, polysaccharide, nucleic acid molecule, and or organic small molecule.

25. The method of paragraph 24, wherein the nucleic acid molecule is selected from antisense, siRNA, miRNA, anti-miRNA, piRNA, aptamers, ribozymes, external guide sequences for ribonuclease P, triplex forming agents, and CRIPSR/Cas component(s), or a polynucleotide encoding any of the foregoing.

26. The method of paragraph 25, wherein the nucleic acid molecule is an miRNA, anti-miRNA, or a polynucleotide encoding the foregoing.

27. The method of paragraph 26, wherein the miRNA is a pri-miRNA, pre-miRNA, mature miRNA, miRNA mimics, or fragments or variants thereof that retains the biological activity of the miRNA.

28. The method of paragraph 27, wherein the miRNA targets an oncogene.

29. The method of any one of paragraphs 22-28, wherein the loading of the lipid vesicles comprises mixing vesicles and active agent alone or in combination with one or more of incubation, freeze-thaw cycling, sonication, extrusion, chemical transfection, and electroporation.

30. The method of paragraph 29 wherein the active agent is an miRNA and the loading of the active agent comprises electroporation.

31. A functionalized lipid vesicle formed according to the method of any one of paragraphs 1-30.

32. A pharmaceutical composition comprising the functionalized lipid vesicles of paragraph 31.

33. A method of treating a subject in need thereof comprising administering to the subject an effective amount of the functionalized lipid of paragraph 31 or the pharmaceutical composition of paragraph 32.

34. The method of paragraph 33, wherein the subject has cancer and the active agent treats the cancer.

35. A method of making functionalized lipid vesicles comprising a lipid membrane, the method comprising mixing in the presence of detergent, lipid vesicles comprising one or more lipids with one or more types of lipid conjugates, each type of lipid conjugate comprising a lipid component and a functional element, and dialyzing the mixture for an effective amount of time for the lipid conjugate(s) to insert into the lipid vesicles and form functionalized lipid vesicles, wherein the lipid vesicles are naturally occurring exosomes isolated from cultured or uncultured tissue, cells, or fluid.

36. The method of paragraph 35, wherein the functional element is an antibody.

37. The method of paragraph 36, wherein the antibody specifically targets a cancer antigen.

38. The method of paragraph 37, further comprising loading the lipid vesicles or functionalized lipid vesicles with an active agent.

39. The method of paragraph 38, wherein the active agent is a tumor suppressor miRNA or mimic thereof.

40. A functionalized exosome vesicle formed according to the method of paragraph 39.

41. A method of treating a subject in need thereof comprising administering to the subject an effective amount of the functionalized lipid of paragraph 40.

42. The method of paragraph 41, wherein the subject has cancer, the functional element targets cells of the cancer, and the active agent treats the cancer.

EXAMPLES

Example 1: Construction and Confirmation of Antibody-Labeled Exosomes

Abbreviations used herein, particularly in the Examples 1-5

β-HCG: β-human chorionic gonadotropin
2;-OMA: 2'-O-(N-(methyl)acetamido)
2'-OAE: 2'-O-amonioethyl
2'-OGE: 2-guanidoethyl (2'-OGE),
2'-OME: 2'-O-(methoxyethyl)
$^{99m}$Tc: Technetium99
A: adenine
AB: apoptotic bodies and/or blebs
Abi-exosome: antibody-labeled exosome
ALIX: ALG-2 interacting protein X
ANOVA: analysis of variance
antimiR: molecules targeting miRNA
ATX: autotaxin
Bp: base pairs
C: cytosine
Cas: CRISPR-associated
CD: cluster of differentiation
cDNA: complementary DNA
CEA: carcinoembryonic antigen
CMC: critical micelle concentration
CRISPR: clustered regularly interspaced short palindromic repeats
crRNA: pre-CRISPR RNA
CT: cancer/testes
CTAB: P-alanyl cholesterol, cetyl trimethyl ammonium bromide
DC-Chol: 3-[N-(N',N'-dimethylamino-ethane)carbamoyl] cholesterol
DDM: n-dodecyl-p-D-maltoside
DEED: diethyl-ethylenediamide
DHPE: 1,2-dihexadecylphosphoethanolamine
DLS: dynamic light scattering
DMAP: dimethyl-aminopropylamine
DMPC: 1,2-dimyristoylphosphatidylcholine
DMRIE: 1,2-dimyristyloxypropyl-3-dimethyl-hydroxylethyl ammonium bromide
DMTAP: dimyristoyl-N-[1-(2,3-dioleoyloxy)propyl]-N,N,N-trimethyl ammonium salt
DNA: deoxynucleic acid
DOGS: dioctadecylamidoglycylspermine
DOPE: 1,2-dioleylphosphoethanolamine
DORI: 1,2-dioleoyl-3-dimethyl-hydroxyethyl ammonium bromide
DORIE-HB: 1,2-dioleyl-oxy-propyl-3-dimethyl-hydroxybutyl ammonium bromide
DORIE-HP: 1,2-dioleyloxypropyl-3-dimetyl-hydroxypropyl ammonium bromide
DORIE-Hpe: 1,2-dioleyloxypropyl-3-dimethyl-hydroxypentyl ammonium bromide
DORIE: 1,2-dioleyloxypropyl-3-dimethyl-hydroxyethyl ammonium bromide
DOSPA: 2,3-dioleoyloxy-N-(2-(sperminecarboxamido)-ethyl)-N,N-dimethyl-1-propanaminium trifluoro-acetate
DOSPER: ditetradecanoyl-N-(trimethylammonio-acetyl) diethanolamine chloride, 1,3-dioleoyloxy-2-(6-carboxy-spermyl)-propylamide
DOTAP: dioleoyl-N-[1-(2,3-dioleoyloxy)propyl]-N,N,N-trimethyl ammonium
DOTIM: 1-[2-(9(Z)-octadecenoyloxy)ethyl]-2-(8(Z)-heptadecenyl-3-(2-hydroxyethyl)imidazolinium chloride
DOTMA: N-[1-(2,3-dioleyloxy)propyl]-N,N,N-trimethylammonium chloride
DPPC: 1,2-dipalmitoyl phosphatidylcholine
DPRIE: 1,2-dipalmityloxypropyl-3-dimethyl-hydroxyethyl ammonium bromide
DPTAP: dipalmitoyl-N-[1-(2,3-dioleoyloxy)propyl]-N,N,N-trimethyl ammonium salt
DPTIM: 1-[2-(hexadecanoyloxy)ethyl]-2-pentadecyl-3-(2-hydroxyethyl)imidazolinium chloride
DRM: dehydration rehydration method
DSPC: 1,2-distearoylphosphatidylcholine
DSPE-PEG(2000) Maleimide: 1,2-distearoyl-sn-glycero-3-phosphoethanolamine-N-[maleimide(polyethylene glycol)-2000]
DSPE: 1,2-disteroyl-sn-glycero-3-phosphoethanolamine
DSRIE: 1,2-disteryloxypropyl-3-dimethyl-hydroxyethyl ammonium bromide
dsRNA: double-stranded RNA
DSTAP: distearoyl-N-[1-(2,3-dioleoyloxy)propyl]-N,N,N-trimethyl ammonium salt dimethyldioctadecyl ammonium bromide (DDAB), 1,2-diacyloxy-3-trimethylammonium propanes, N-[1-(2,3-dioloyloxy)propyl]-
DODAP: N,N-dimethyl amine
ECM: extracellular matrix
EGFR: epidermal growth factor receptor
EGS: external guide sequence
EIM: ether injection method
ELR: "glu-leu-arg" motif
EpCAM: epithelial cell adhesion molecule
ESG: external guide sequences
FAT: freeze and thaw method
FBS: fetal bovine serum
FITC: fluorescein isothiocyanate
FSH-R: follicle stimulating hormone receptor
G: guanine
GAG: glycosaminoglycan
GalNAc: glycosyltransferase β-1,4-N-acetylgalactosaminyltransferases
GPCRs: G-protein coupled receptors
HA: hemagglutinin
HDR: homology-directed repair
HM: heating method
HPLC: high performance liquid chromatography
HSM: hand shaking method
IM: intramuscular
IP: intraperitoneal
IRES: internal ribosome entry sequence
IV: intravenous
$K_d$: dissociation constant LNA: locked nucleic acids
LPS: lipopolysaccharide
LUV: large unilamellar vesicles
MALP-2: mycoplasmal lipoproteins
MCC: maleimidomethylcyclohexane-carboxamide
MCC-PE: 1,2-dioleoyl-sn-glycero-3-phosphoethanolamine-N-[4-(p-maleimidomethyl)cyclohexane-carboxamide]
miRNA: microRNA
MLV: multilamellar vescicles
MPB: maleimidophenylbutyramide
MPB-PE: 1,2-dioleoyl-sn-glycero-3-phosphoethanolamine-N-[4-(p-maleimidophenyl)butyramide]
MRA: mesothelin related antigen
mRNA: messenger RNA
MV: microvesicles
NBD-DSPE: 1,2-distearoyl-sn-glycero-3-phosphoethanolamine-N-(7-nitro-2-1,3-benzoxadiazol-4-yl)
NHEJ: nonhomologous end joining
oncomiR: oncogenic miRNA
PAMPs: pathogen-associated molecular patterns
PBMCs: peripheral blood mononuclear cells
PBS: phosphate buffered saline
pC: 5-(1-propynyl) cytosine
PC: phosphatidylcholine
PDGF: platelet derived growth factor receptor
PDP: pyridyldithiopropionate
PDP-PE: 1,2-dioleoyl-sn-glycero-3-phosphoethanolamine-N-[3-(2-pyridyldithio)propionate]
PE: phosphatidylethanolamine
PEG: poly-(ethylene glycol)
PG: phosphatidylglycerol
PI: phosphatidylinositol
piRNA: piwi-interacting RNA
PNA: peptide nucleic acid
Pre-miRNA: precursor miRNA
Pri-miRNA: primary miRNA
PS: phosphatidylserine
PSA: prostate surface antigen
PTEN: phosphatase and tensin homolog
pU: 5-(1-propynyl) uracil
Rab5: Ras-related protein
REV: reverse phase evaporation method
RI: refractive index
RISC: RNA-induced silencing complex
RNA: ribonucleic acid
RNAi: RNA interference
RVD: repeat variable diresidue
SIP: sphingosine-1-phosphate
scFv: single chain variable fragments
sdAb: single antibody antibody fragments
sdFv: disulfide-linked fragments
sgRNA: single-guide RNA
shRNA: short double-stranded hairpin-like RNAs
siRNA: short interfering RNA
SSL: sterically-stabilized liposomes
SubQ: subcutaneous
SUV: small unilamellar vescicles
T: thymine
TAL: transcription activator-like
TALEN: transcription activator-like effector nuclease
tcPNA: “tail-clamp” peptide nucleic acids
TFH: thin-film hydration method
TFO: triplex forming oligonucleotide
TLRs: toll-like receptors
TMAG: di$C_{14}$-amidine, N-ferf-butyl-N'-tetradecyl-3-tetradecylamino-propionamidine, N-(alpha-trimethylammonioacetyl)didodecyl-D-glutamate chloride
TNT: tunneling nanotubes
tracrRNA: trans-activating crRNA
tRNA: transfer RNA
U: uracil
ZFNs: zinc finger nucleases Materials and Methods Harvesting of human peripheral blood mononuclear cells (PBMCs)

Human donors were enrolled for blood collection in compliance with the guidelines of the World Medical Association’s Declaration of Helsinki and the Human Research Protection Program and Institutional Review Board guidelines for human subject research at University of Georgia. Enrolled healthy volunteers signed the consent forms following appropriate introduction about the study. The human blood protocol (University of Georgia protocol no. 2012-10769) and the consent form were reviewed and approved by the Institutional Review Board of the University of Georgia. PBMCs were isolated from heparinized blood samples using the Histopaque 1077 Reagent (Sigma Aldrich, St. Louis, MO, USA) as per manufacturer instructions and as previously described (Sil et al., *Inflamm Res.* 66(3):227-37 (2017) doi: 10.1007/s00011-016-1008-0). PBMCs were resuspended in RPMI without glutamine and phenol red (Coming, Coming, NY, USA) supplemented with 1M HEPES buffer solution (Sigma Aldrich). Cells were counted and plated at a density of 1 million cells per 25 $cm^2$ in a 75 $cm^2$ flask in RPMI (Coming, Corning, NY, USA) supplemented with 10% fetal bovine serum (FBS) (Atlanta Biologicals, Flowery Branch, GA, USA) and penicillin/streptomycin (Thermo Fisher, Waltham, MA, USA) in a humidified atmosphere of 5% CO2 at 37° C. for 24-48 h.

Preparation of Fatty Acids, Antibody and Exosomes

Two fatty acids, namely 1,2-distearoyl-sn-glycero-3-phosphoethanolamine-N-[maleimide(polyethylene glycol)-2000], or DSPE-PEG(2000) maleimide, and fluorescent 1,2-distearoyl-sn-glycero-3-phosphoethanolamine-N-(7-nitro-2-1,3-benzoxadiazol-4-yl), or NBD-DSPE (Avanti Polar Lipids, Alabaster, AL, USA), were obtained and dissolved in DMSO to yield a 1 mg/mL solution of fatty acids. DDM detergent (Sigma Aldrich) was resuspended in 1x PBS to yield a 100 mg/mL solution. Subsequently a 0.1% w/v solution of DDM was also prepared using 1x PBS. DSPE-PEG 2000 Maleimide and fluorescent NBD-DSPE fatty acids were dissolved in 1 mL of 0.1% DDM at a concentration of 100 μM each. This solution was used to verify appropriate excitation and emission of the fluorescent NBD-DSPE using the SpectraMax M2 Plate Reader (Molecular Devices, Sunnyvale, CA, USA), with excitation at 445-460 nm with an expected emission at 540 nm (data not shown). This 1:1 mixture of the two fatty acids was used for Abi-exosomes construction.

PBMCs were plated in RPMI (Corning) supplemented with 10% fetal bovine serum (FBS) (Atlanta Biologicals) and penicillin/streptomycin (Thermo Fisher) as described above. Exosomes were isolated from PBMCs using the Exiqon Exosome Isolation Kit (Exiqon, Woburn, MA, USA) and stored at −80° C. if required prior to use.

Invitrogen ENPP2/autotaxin antibody (Product No. PA5-12478) (Thermo Fisher) as well as Cell Signaling Technologies CD44 (Product No. #37259S) and CD29/Integrin beta-1

(Product No. #4706S) antibodies were purchased and stored at −20° C. prior to use (Cell Signaling Technologies, Danvers, MA, USA).

Construction of Fatty Acid-Antibody Anchored Exosomes

The fatty acid solution containing 1:1 DSPE-PEG(2000) Maleimide:NBD-DSPE in 0.1% DDM was dialyzed using Slide-A-Lyzer MINI Dialysis units with a 10,000-molecular weight cut-off (Thermo Fisher) against 2 L of 1x PBS for 2 h in a 4° C. cold room. Following dialysis, presence of the fatty acid was deduced by exciting a 1:10 dilution of the sample between 445-460 nm and confirming an emission at 540 nm using SpectraMax M2 Plate Reader. The remaining sample was combined with antibody at a 2:1 ratio to generate the antibody-label and the sample was centrifuged and incubated at room temperature for 1 h prior to addition of 100 μL of purified exosomes from PBMCs. This solution was mixed by pipetting, briefly centrifuged, and incubated at room temperature for an additional 1 h. Then, the sample once again underwent dialysis using the 10,000 Dalton molecular weight cut-off dialysis units against 2 L of 1x PBS for 2 h in a 4° C. cold room to integrate the fatty acid-attached antibody into the exosomal membrane and remove all DDM from solution.

The dialyzed product, containing the antibody-label integrated into the exosomal membrane, creating Abi-exosomes, was incubated overnight with Exosome Precipitation Buffer from the Exosome Isolation Kit per manufacturer instructions (Exiqon) to precipitate the Abi-exosomes. The solution was then centrifuged at 50,000 rpm for 1 h at 20° C. to pellet the Abi-exosomes, the supernatant was removed and the final product was resuspended in 1x PBS and electroporated with miRNA before addition to cells. Electroporation was performed using the BioRad Gene Pulser X-Cell CE was used to electroporate miRNA into the Abi-exosomes using an exponential decay exposure at 150 Volts and 125 μF of capacitance for 10-15 microseconds in a 4 mm cuvette.

Dynamic Light Scattering

The DLS technique is a powerful tool for estimating the sizes and distributions of particles (typically in submicron range) in a solution using their light scattering properties (Berne and Pecora, Dynamic Light Scattering: With Applications to Chemistry, Biology, and Physics, Unabridged edition, Dover Publications, Mineola, N.Y, 2000, Schmitz, Introduction to Dynamic Light Scattering by Macromolecules, Academic Press, Boston, 1990.). To determine whether antibodies were successfully anchored into the exosomal membrane to form Abi-exosomes, dynamic light scattering was used to determine particle size in solution compared to each individual component required for the final product. Undiluted antibody, purified exosomes and fatty acid at or below critical micelle concentration (CMC, $H_2O$=0.0087% DDM) were prepared for this method. It was initially believed there could be an increase in particle size in the 10-20 nm range due to the small size of the fatty acid and ~10-15 nm size of antibody attached to the exosome. Since the refractive index (RI) of water (RI: 1.337; viscosity: 0.887 cP; temperature: 25° C.) differs from that of lipid vesicles (RI: 1.447; absorption: 0.001), the presence of the particle in solution was detectable (Matsuzaki et al. *Biochim Biophys Acta.,* 1461(1):219-26 (2000)). The Zetasizer Nano ZS was used to perform dynamic light scattering and configured with a customized protocol to determine size of exosomes and Abi-exosomes (Malvern Panalytical, Malvern, United Kingdom). The Zetasizer software, provided by Malvern Panalytical, was used to obtain and analyze data.

Statistics

One-way analysis of variance (ANOVA) test was used to determine statistical significance between groups comparing miRNA uptake into cells. A confidence interval of 95% with all p-values less than 0.05 was considered significant (*). Student's T-Test was also used to compare two groups to one another, also with a 95% confidence interval. Microsoft Excel and GraphPad Prism 7 were utilized for numerical data analysis and statistical significance.

Results

Figure 1B:
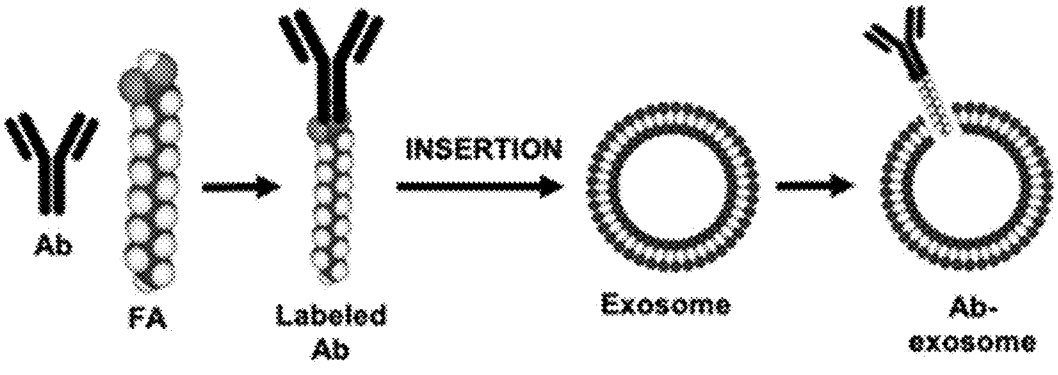
FIG. 1B is flow diagram illustrating an exemplary method of making functionalized exosomes. For example, an antibody can be covalently linked through amine functional groups to a fatty acid optionally with a polyethylene glycol (PEG) tail, e.g., a Polyethylene glycol 2000 (PEG(2000)). This conjugate is inserted into exosomal membrane by removing hydrophobicity-stabilizing detergent through dialysis and forms antibody-labeled exosomes ("Abi-exosomes").
Figure 1C:
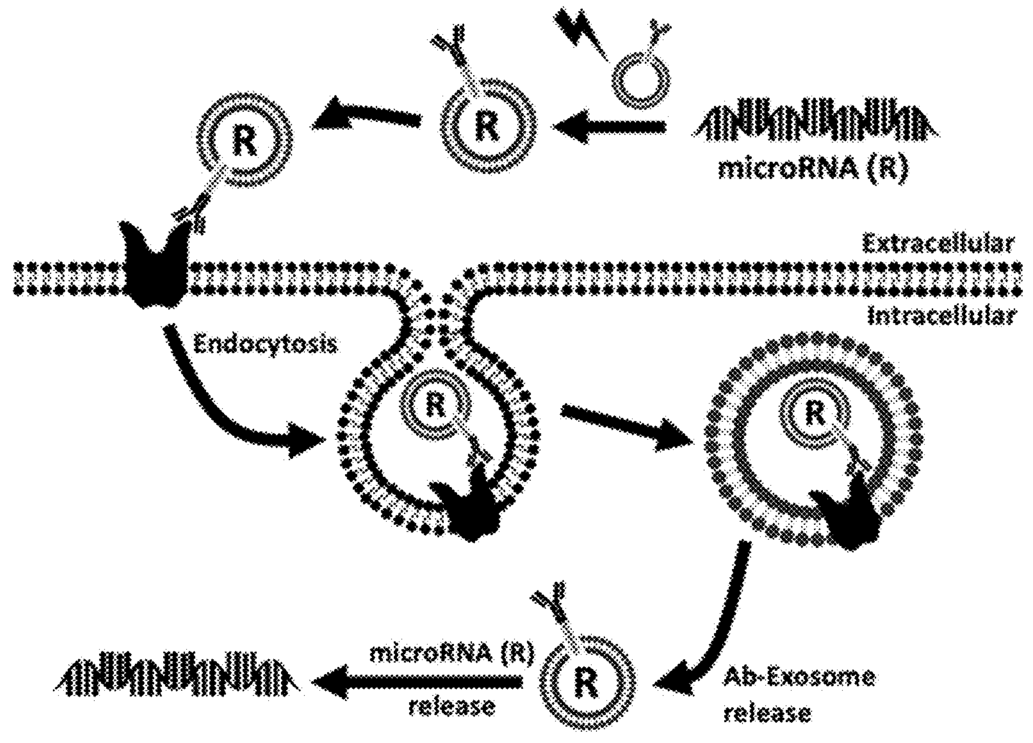
FIG. 1C is an illustration of a model of exosome delivery of cargo to cells. Following loading (e.g., electroporation) of cargo (e.g., miRNA (R)) into bioengineered exosome (e.g., Abi-exosomes), a targeting moiety (e.g., antibodies) on the exosomes binds to the targets, which are on or near the cell surface. This is followed by exosome internalization. Once internalized, the exosomes are degraded and the cargo is released from the particle. In the illustration, the cargo is miRNA that upon release finds and inhibits its target mRNA.

In order to bioengineer customizable Abi-exosomes to target a specific protein on cell surfaces, a fatty acid, autotaxin antibody, and purified exosomes from human peripheral blood mononuclear cells were utilized. PBMCs were cultured and exosomes therein extracted after obtained blood from a human donor (FIG. 1A). Then, the antibody and fatty acid were incubated together in the presence of 0.1% DDM detergent to result in a covalent bond attaching the fatty acid to the antibody tail. Subsequently, the antibody labeled with fatty acid, now considered and referred to as the antibody-label, was incubated with exosomes and underwent dialysis to remove the DDM detergent stabilizing the hydrophobic fatty acid tail. This resulted in insertion of the fatty acid into the exosomal membrane to maintain its hydrophobicity, forming antibody-labeled exosomes (also referred to herein as Abi-exosomes). (FIG. 1B). miRNA (R) was introduced into the Abi-exosomes by electroporation (FIG. 1C).

To confirm insertion of the antibody into the exosome, the size increase was monitored by the dynamic light scattering technique. (Stetefeld et al., *Biophys Rev.* 8(4):409-27 (2016) doi: 10.1007/s12551-016-0218-6). During the process of engineering an Abi-exosome, insertion of the antibody with pegylated fatty acid into the exosome will significantly increase the size of the particle. The polyethylene glycol-2000 (PEG(2000)) and the antibody will contribute to the change in particle size. From previous dynamic light scattering experiments, PEG(2000) was found to have a hydrodynamic radius and diameter of 1.6 and 3.2 nm, respectively (Ling et al., Nanoscale Research Letters 8(1):538 doi: 10.1186/1556-276X-8-538). A generic IgG antibody was found to have an average hydrodynamic diameter of 11.3 nm by dynamic light scattering analysis (Nobbman et al., Biotechnology and Genetic Engineering Reviews 24(1):117-128 (2007) doi: 10.1080/02648725.2007.10648095). The PEG(2000) and the IgG antibody have a combined hydrodynamic diameter of 14.5 nm. Therefore, the Abi-exosome diameter could be as much as 29 nm larger than an unlabeled exosome.

Figure 2A:
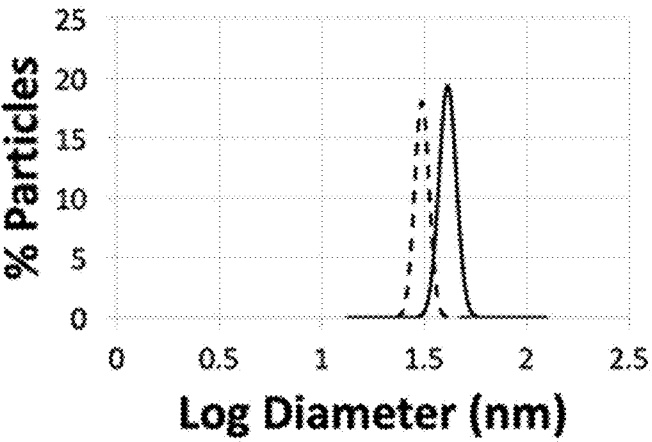
FIGS. 2A-2B are line graphs showing that dynamic light scattering confirms a particle size increase indicative of Ab-exosome formation. Dynamic light scattering provides a means to measure particle size in solution and deduce whether Ab-exosomes were successfully formed.
Figure 2B:
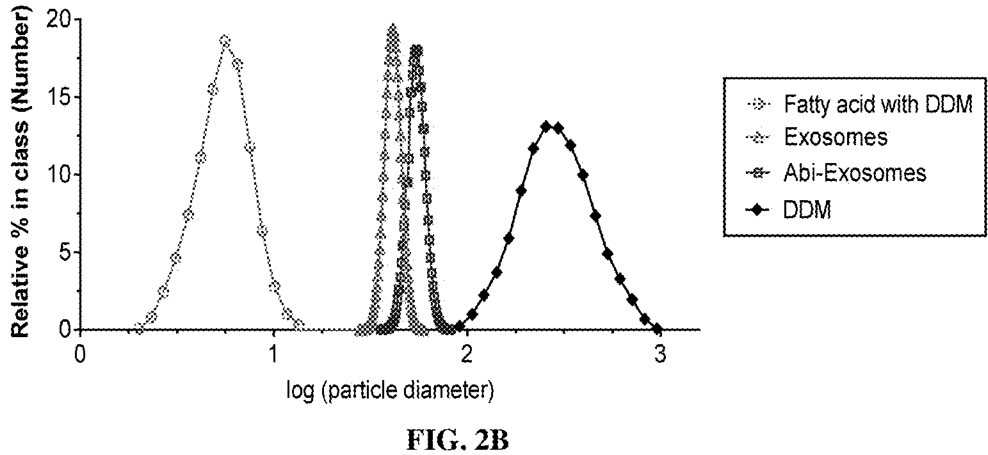

Results indicated that this was indeed the case; the Abi-exosomes had a particle size approximately 12 nm larger in size on average compared to purified exosomes without the antibody-label attachment, and was therefore deemed to be successfully constructed, possibly with multiple antibody attachments per exosome (FIGS. 2A-2B). Autotaxin antibody was consistent with the 10-15 nm size expected, however, fatty acid micelles were unable to be broken up and generated large, inaccurate particle size measurements.

A first dynamic light scattering chromatogram in FIG. 2A shows the size of the exosome before and after insertion of the antibody with pegylated fatty acid. Upon insertion of the antibody with pegylated fatty acid, the exosome diameter increases from 40 nm to 54 nm (corresponding to a rightward peak shift comparing exosomes alone and Abi-exosomes).

A second dynamic light scattering chromatogram in FIG. 2B shows the particle size distribution DLS chromatograms determined from experiments in nm. Each of the samples showed a distinct average size and distributions. The fatty acids (i.e. a mixture of 100 μM DSPE-PEG 2000 and 100 μM NBD-DSPE) solubilized in 0.1% w/v DDM had a size distribution of 6.3±2.0 nm. The size distribution of exosomes was considerably higher with a diameter of 39.8±5.0 nm. This is in the typical size distribution range observed for exosomes (Doyle, et al., 8(7), 727 (2019) doi.org/10.3390/cells8070727; Lim, et al., *J. Nanobiotechnology.* 17(1) (2019) doi.org/10.1186/s12951-018-0433-3). The average diameter of Abi-exosomes was about 10 nm higher at 50.1±8.0 nm. The size increase is consistent with antibody labelling within the Abi-exosomes (Reth, *Nat. Immunol.* 14 (2013) 765-767 doi.org/10.1038/ni.2621). In contrast, DDM detergent micelles were 5-fold larger at the critical micelle concentration (CMC) with a size distribution of 251±164 nm.

The experiments illustrated in FIGS. 2A and 2B both utilized ENPP2/autotaxin antibody.

Example 2: Cellular Delivery of miRNA with Abi-Exosomes

Materials and Methods

Electroporation of Exosomes with miRNA

The miRNA mimic used is an miR-489-3p miRNA mimic having the sequence GUGACAUCACAUAUACGGCAGC (SEQ ID NO:1).

```
                                    (SEQ ID NO: 1)
GUGACAUCACAUAUACGGCAGC.
```

Exosomes were quantified using the Pierce BCA Protein Assay Kit (Thermo Fisher) as per manufacturer's protocol. Under a sterile hood, 1 μg each of exosomes and miRNA mimic obtained from Thermo Fisher were combined in 400 μL of serum-free DMEM medium in a Gene Pulser Cuvette (Bio-Rad, Hercules, CA, USA). The Bio-Rad Gene Pulser X-Cell CE was used to electroporate miRNA into the Abi-exosomes using an exponential decay exposure at 150 Volts and 125 μF of capacitance for 10-15 microseconds in a 4 mm cuvette. The electroporated product was subsequently incubated at room temperature for 30 min prior to treating cells.

Treatment of Cell Lines

MDA-MB-231 cells were grown and maintained in DMEM (Corning) supplemented with 10% fetal bovine serum (FBS) (Atlanta Biologicals), penicillin/streptomycin (Thermo Fisher) and incubated in a humidified atmosphere of 5% CO2 at 37° C. Cell lines were plated at 200,000 cells per well in a 6-well plate and incubated overnight. Media was refreshed the following day with 2.7 mL of fresh 10% DMEM or RPMI (complete medium) and treated with 300 μL of Abi-exosomes electroporated with miRNA. The plate was incubated for 48 or 72 h before protein or intracellular RNA and extracellular exosomal RNA were extracted.

Intracellular and Exosomal RNA Extraction and Quantitative Real-Time PCR

TRIzoI Reagent (Invitrogen, Carlsbad, CA, USA) was used to isolate intracellular RNA as per the manufacturer's protocol. Exosomal RNA extraction was performed using the Exosome Isolation Kit followed by the miRCURY RNA Isolation Kit —Cell & Plant (Exiqon). All RNA was stored at −80° C.

Complementary DNA (cDNA) was prepared from intracellular and exosomal RNA using the Taqman microRNA Reverse Transcription Kit (Thermo Fisher). cDNA was run in a 384-well format in a quantitative real-time PCR (qRT-PCR) assay using Taqman Universal PCR MasterMix (Thermo Fisher) and the ABI 7900HT machine (Applied Biosystems, Foster City, CA, USA) as per manufacturer protocols. Microsoft Excel and GraphPad Prism 7 were used for data analysis and statistics.

Results

Experiments were designed to assess whether miRNA delivery into cells could be increased by encapsulating the miRNA into purified PBMC-derived exosomes compared to standard miRNA transfection. For this, 1 μg of exosomes were electroporated with 1 μg of miR-489-3p miRNA mimic, and added to cells for 72 h to allow for exosomal uptake. Then, RNA was extracted from cells and exosomes in cultured media, and miRNA levels were assessed by qPCR.

Exosomes alone or those incubated with miRNA but without electroporation had significantly lower miRNA levels in cells. In fact, electroporated exosomes contained up to 700,000-fold higher levels of miRNA compared to purified exosomes, and were successfully taken up by cells to result in higher miRNA concentrations compared to the transfection (*$p<0.05$) (FIG. 3A). Transfection is the standard method of miRNA delivery into cells involving encapsulating miRNA in a transfection reagent such as Dharmafect to ensure stable delivery into cells.

As attachment of an antibody-label to the exterior of the exosomal membrane may present some structural hindrances for exosomal uptake into cells, miRNA uptake with and without the antibody-label were measured. Strikingly, attachment of an antibody to exosomes increases miRNA uptake efficiency into the cells compared to both unlabeled exosomes and miRNA transfection. More specifically, Abi-exosome mediated miRNA delivery into cells is much more efficient than miRNA electroporation and delivery using plain exosomes (*$p<0.001$) without the antibody-label (FIG. 3**B).

Figure 3B:
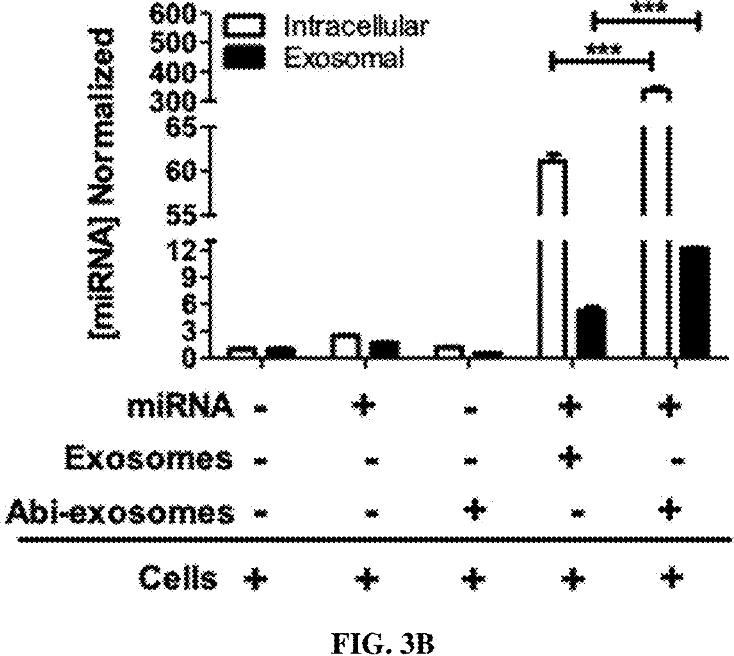
FIG. 3B is a bar graph comparing miRNA transfection (miRNA alone) to miR electroporated into either purified exosomes or Abi-exosomes.
Figure 3C:
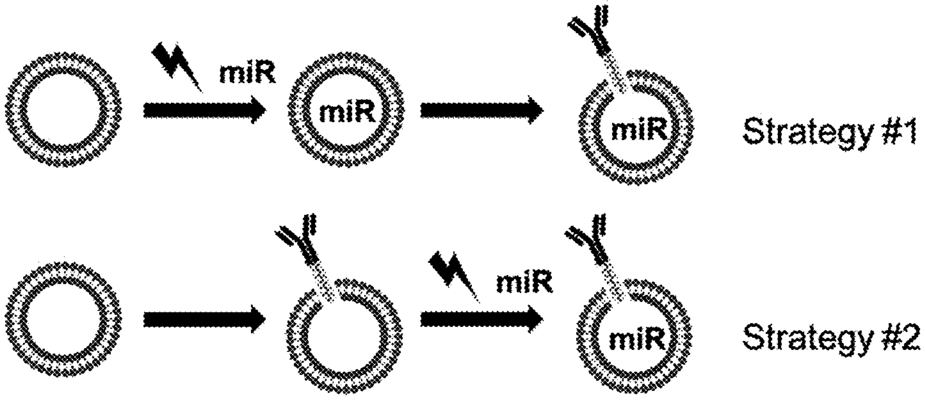
FIG. 3C is a flow diagram illustrating two different strategies for loading (e.g., electroporation) exosomes with cargo (e.g., miRNA): before ("Strategy #1") and after ("Strategy #2") functionalization.
Figure 3D:
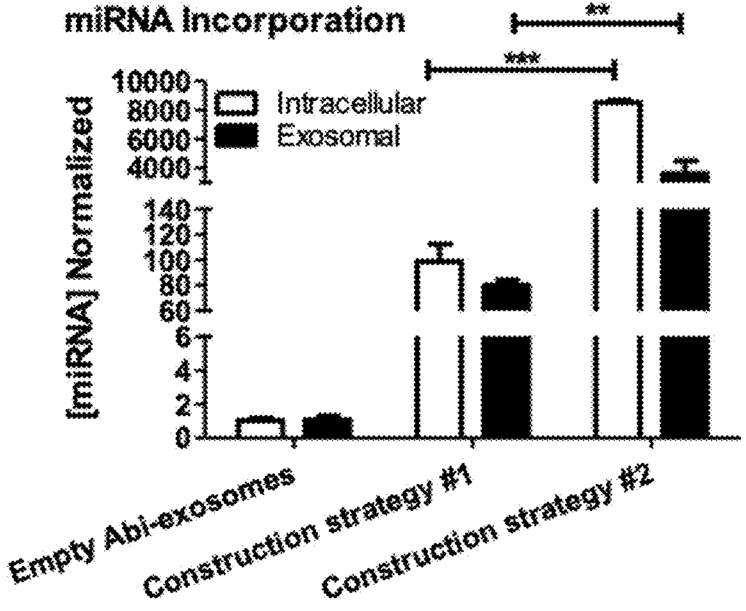
FIG. 3D is a bar graph showing the effect of electroporation of miRNA into completed Abi-exosomes (Strategy #2) compared to miRNA electroporation into naked exosomes before particle construction (Strategy #1).

Next, miRNA electroporation efficiency and subsequent stability in the Abi-exosomes were investigated to ensure successful uptake and delivery into cells. Electroporation of miRNA could occur either before ("Strategy #1") or after ("Strategy #2") construction of Abi-exosomes (FIG. 3C). Using qRT-PCR measuring miRNA expression, it was discovered that miRNA electroporation after Abi-exosome construction resulted in higher miRNA levels in the exosomes and subsequently, higher cellular concentrations. Comparatively, miRNA electroporation into naked exosomes before Abi-exosome construction resulted in much lower miRNA uptake (FIG. 3D). This result indicates that miRNA uptake efficiency into cells is increased when miRNA is electroporated into fully contrasted Abi-exosomes (***$p<0.001$). This shows that the Abi-exosome particle is able to withstand miRNA electroporation. All miRNA expression was normalized to U6 endogenous control expression.

Example 3: Investigation of Antibody-Label

Materials and Methods

Cell lines, Protein Extraction and SDS-PAGE gel electrophoresis

OVCAR-3, MeWo and BT-474 cells were grown in RPMI medium (Corning) supplemented with 10% fetal bovine serum (FBS) (Atlanta Biologicals) and penicillin/streptomycin (Thermo Fisher) and incubated in a humidified atmosphere of 5% CO2 at 37° C. Cells were washed with 1x PBS twice and centrifuged at 4000 rpm for 5 min to collect cell pellet before addition of RIPA Lysis and Extraction Buffer containing Protease/Phosphatase Inhibitor Cocktail (100x) (Thermo Fisher). They were shaken on ice with occasional vortexing for 30 min, sonicated and centrifuged at 13,000 rpm for 10 min to collect the protein supernatant. Protein was stored at −80° C. before quantification using the Pierce BCA Protein Assay Kit (Thermo Fisher) as per manufacturer's protocol.

Samples were boiled with 6x Laemelli sample buffer at 95° C. for 5-10 minutes prior to loading on an SDS-PAGE gel. The BioRad SDS-PAGE System and protocol were used to probe for CD44, CD29, and GAPDH antibodies at 1:1000 dilution overnight and HRP-conjugated anti-rabbit secondary antibodies at 1:10000 dilutions (BioRad; Cell Signaling Technologies). The Flourchem Imager System (Protein Simple, San Jose, CA, USA) was used to detect bands on the PVDF membranes and band quantification was performed using the ImageJ Software (National Institutes of Health, Rockville, MD, USA).

Antibodies were from Cell Signaling Technologies@: CD44 (Product No. 37259S); CD29/Integrin beta-1 (Product No. #4706S), GAPDH (Product No. #5174); I-CAM (Product #4915S).

The miRNA cargo was an miR-21-5p having the sequence

```
(miRBase Accession Number: MI0000077)
                                (SEQ ID NO: 2)
UAGCUUAUCAGACUGAUGUUGA.
```

Results

Figure 4A:
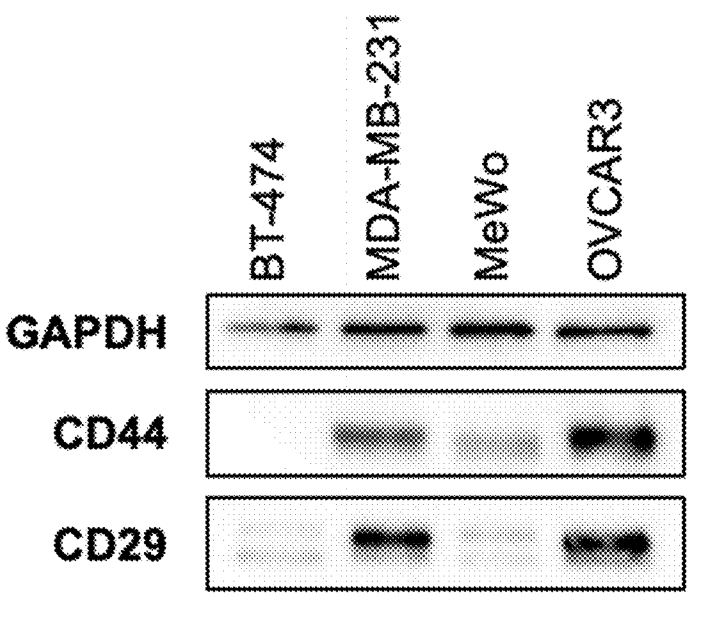
FIG. 4A is an image of an electrophoretic gel showing the detection of CD44 and CD29 on the surface of MDA-MB-231, and other cell types.

Previous studies have shown that certain proteins, such as CD44, and CD29/Integrin s-1 are overexpressed on the surface of MDA-MB-231 cells (Lobba et al., *Cytometry A*. 81(12):1084-91 (2012) doi: 10.1002/cyto.a.22220, Cahall et al., *Breast Cancer* (Auckl). 9(Suppl 1):1-11 (2015) doi: 10.4137/BCBCR.S25461). Targeting these proteins might allow for more proximity of Abi-exosomes and higher uptake efficiency into cells. The expression of these markers on TNBC MDA-MB-231 cells, as well as ER+/PR+/HER2+ (triple positive) BT474, MeWo (melanoma) and OVCAR-3 (high grade serous ovarian carcinoma) cell lines was measured (FIG. 4A). Results confirmed the overexpression of both CD44 and CD29 in MDA-MB-231 cells compared to BT474 (triple-positive breast cancer) and MeWo (melanoma) cells. ICAM-1 expression was tested, but not confirmed, possibly due to low expression in all four cell lines. OVCAR-3 also had higher CD44 and CD29 expression, possibly related to the gynecological origin of this tumor type as well.

Figures 4B, 5:
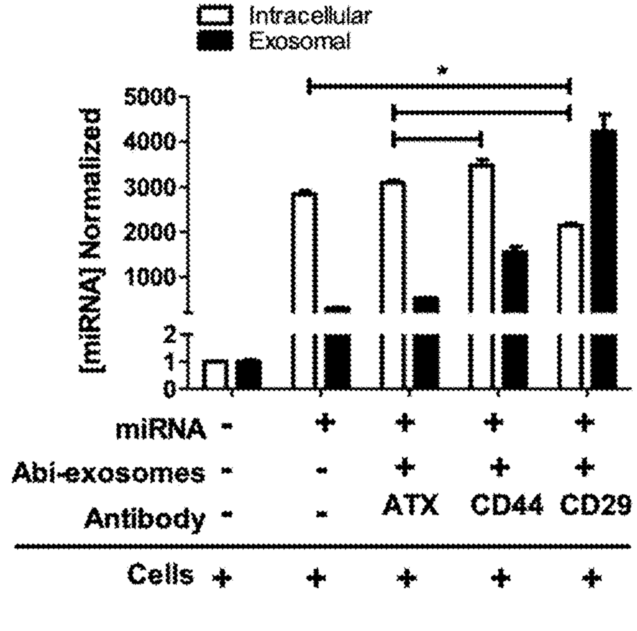
FIG. 4B is a bar graph comparing to the use of antibodies autotaxin, CD44 and CD29 in Abi-exosomes construction.
FIG. 5 is a bar graph showing miR-21-5p targets and inhibits PTEN expression in MDA-MB-231 cells. miR-21-5p has long been characterized as having the ability to target the prominent oncogene PTEN, which is responsible for controlling cell growth and survival, among other roles.

When CD44 (Cell Signaling Technologies® Product No. 37259S) and CD29/Integrin beta-1 (Cell Signaling Technologies® Product No. #4706S) antibodies were used for Abi-exosome construction, miRNA expression after treatment in MDA-MB-231 cells showed that CD44-labeled-exosomes had the highest miR-21-5p miRNA delivery efficiency into cells (FIG. 4B). CD44-labeled Abi-exosomes are more effective at miRNA delivery than autotaxin-labeled Abi-exosomes (*p<0.05) and CD29-labeled Abi-exosomes. MiRNA concentration was normalized to U6 endogenous control expression in cells and exosomes.

CD29-labeled-exosomes achieved less efficient miRNA delivery, whereas autotaxin-labeled-exosomes were comparable to the standard miRNA transfection efficiency. This may be due to autotaxin not being on the cell surface like CD44, but simply proximal to the surface. Therefore, targeting CD44 results is more closeness of the Abi-exosomes to the cell surface, increasing their probability of being internalized.

ICAM-1-labeled-exosomes were also tested and comparable to the standard miRNA transfection efficiency, however, as noted above, ICAM-1 expression was not confirm.

This data shows that while Abi-exosomes targeting an extracellular enzyme close to the cell surface can be slightly more efficient than miR transfection, directly targeting a marker on the cell surface can result in significantly higher miR uptake into cells (*p<0.05). Less efficient miR delivery (*p<0.05) by CD29-labelled exosomes was possibly due to inefficient targeting by the antibody to this surface marker.

Example 4: Functionality of miRNA delivery into TNBC cells

Materials and Methods

Generally as described above.

The antibody against CD44 was obtained from Cell Signaling Technologies®: Product No. 37259S.

The miRNA cargo was an miR-21-5p having the sequence UAGCUUAUCAGACUGAUGUUGA (SEQ ID NO:2) (miRBase Accession Number: MI0000077).

Results

To assess functionality of miRNA delivery into cells using Abi-exosomes, the expression of PTEN in MDA-MB-231 cells treated with miR-21-5p containing anti-CD44 antibody-labeled Abi-exosomes was measured. PTEN has been previously reported in various studies to be a target of miR-21-5p in MDA-MB-231 cells and is also implicated in other cancers such as gastric or colorectal cancer (Dai et al., *Oncol Lett.* 14(6):6929-36 (2017) doi: 10.3892/ol.2017.7007, Wu et al., *Cell Physiol Biochem.* 43(3):945-58 (2018) doi: 10.1159/000481648, Wang et al., *DNA Cell Biol.* 37(1):38-45 (2018) doi: 10.1089/dna.2017.3922).

For this experiment, miR-21-5p was electroporated into Abi-exosomes (targeting CD44) and treated cells for 48 hours and then measured the ability of the miRNA to successfully inhibit its intracellular target. Results show that Abi-exosomes increased miR-21-5p levels in the cells (**p<0.01) and were also able to inhibit expression of PTEN significantly in the cell (*p=0.0269). miRNA and PTEN expression were normalized to U6 and 18S endogenous control, respectively.

FIG. 1C illustrates a model of a possible mechanism of delivery of exosomes into cell. Cells treated with the Abi-exosomes are endocytosed and subsequently degraded to release miRNA. Using an antibody for Abi-exosome construction with a protein target on the cell surface is believed to increase proximity of the particles to the cells and further increase cellular uptake efficiency and miRNA levels in the cells.

The experiments above illustrate the development of customizable antibody-labeled exosomes (Abi-exosomes) that can be used as a vehicle to deliver miRNA cargo to cells utilizing exosomes derived from peripheral blood mononuclear cells. MiRNA was electroporated into the particle and incubated with cells to characterize uptake of the Abi-exosomes and miRNA release into the cells (FIG. 1C). Dynamic light scattering, a method often employed to determine particle sizes in solution (Stetefeld et al., *Biophys Rev.* 8(4):409-27 (2016) doi: 10.1007/si2551-016-0218-6), confirmed successful formation of Abi-exosomes by observing an increase in particle size with the addition of the antibody-label to exosomes (FIGS. 2A-2B). Further, experiments comparing efficiency of Abi-exosomes to the standard of miRNA delivery, transfection, and unlabeled exosomes showed that antibody-label attachment results in more efficient uptake and miRNA delivery into cells (FIG. 3A-3B). Additionally, electroporation of miRNA after Abi-exosomes construction (FIG. 3C, Strategy #2) was found to be more efficient for miRNA delivery into cells (FIG. 3D).

When the Abi-exosomes were bioengineered with antibodies targeting markers overexpressed on the MDA-MB-231 cell surface such as CD44 and CD29, CD44-labeled-exosomes were found to be most efficient at uptake and miRNA delivery into cells (FIG. 4B). CD44 is highly overexpressed in various cancer cells and named a prominent regulator of metastasis, especially in breast cancer cells (Senbanjo & Chellaiah, *Front Cell Dev Biol.* 5:18 (2017) doi: 10.3389/fcell.2017.00018). Utilizing this target for cargo delivery with CD44-labeled exosomes allowed the hijacking of a survival tactic for cancer cells to potentially target cancer cells especially with lethal miRNA cargo in the bioengineered exosomes. Compared to autotaxin, which brings the Abi-exosomes close to the cell surface, targeting CD44 brings the Abi-exosomes onto the cell surface to target CD44, increasing the likelihood of their uptake. Functionality of this method was confirmed by treated MDA-MB-231 cells with miR-21-5p, which lead to inhibition of PTEN consistent with previous studies involving the same cell line (Dai et al., *Oncol Lett.* 14(6):6929-36 (2017) doi: 10.3892/ol.2017.7007, Fragni et al., *Naunyn Schmiedebergs Arch Pharmacol.* 389(5):529-38 (2016) doi: 10.1007/s00210-016-1224-8).

Long-term storage of the completed Abi-exosome at −80° C. can reduce the ability of the constructed particle to deliver miRNA into cells. It is possible that the Abi-exosomes themselves are stable when stored at low temperatures, but that the miRNA is unable to be electroporated in or is subsequently exported out of the particle. In this case, electroporating higher concentrations of the miRNA into the Abi-exosome before treatment to cells may increase uptake efficiency. If the Abi-exosome itself is unstable upon storage at −80° C., storage at −20° C. or 4° C. may also be considered.

While the literature outlines increased CD44 expression in MDA-MB-231 cells, CD44 expression is also relatively high in healthy peripheral blood mononuclear cells (Cahall et al., *Breast Cancer* (Auckl). 9(Suppl 1):1-11 (2015)). Since the exosomes used in the disclosed experiments are derived from peripheral blood mononuclear cells, it is possible that they also contain higher expression of CD44, but due to their small size and low concentration, CD44 expression could not be assessed. High CD44 expression on exosomal surfaces could result in the CD44-label targeting the surface of exosomes themselves instead of successfully integrating into the exosomal membrane to form Abi-exosomes. However, dynamic light scattering confirmed that the antibody label is in fact inserted into the exosome, and not targeting a protein on the surface due to the size distribution of Abi-exosomes compared to exosomes alone. In other words, if the antibody-label was not inserted into the exosome, the particle size increase would be up to two times higher based on the component sizes.

Example 5: Abi-Exosomes that Target Hepatocytes

The human liver HEPG2 cancer cell line has been has been the focus of many in vitro studies related to the functioning of liver cells and liver cancer [58-60]. The endocytotic asialoglycoprotein receptor 1 (ASGR1) is highly expressed on the surface of HEPG2 cells compared to other cell lines and primary hepatocytes [61]. The ASGR1 receptor forms a trimer and mediates the internalization of desialylated serum glycoproteins through receptor-mediated endocytosis [62]. This receptor has been successfully used to facilitate small molecule uptake into HEPG2 cells through the ASGR1 receptor [63-65]. Galactosamine covalently linked to albumin and nanoparticles loaded with pullulan and arabinogalactan has selectively delivered the anti-cancer drug doxorubicin to HEPG2 cancer cells [63,64]. Pegylated liposomes modified with lactoferrin successfully targeted ASGR1 and delivered the fluorophore coumarin-6 to isolated HEPG2 cells and HEPG2 cells implanted on nude mice [65]. Antisense oligonucleotides have been delivered to HEPG2 cells by linking to the ASGR1 substrate N-acetylgalactosamine [66]. It is believed that ASGR1 Abs have never been used to facilitate molecular uptake through ASGR1 on the surface of HEPG2 cells. In this study, Abi-exosomes were bioengineered with the polyclonal antibody (abCAM, #ab49355) for the ASGR1 receptor ($ASGR1_{PAB}$), which targets the extracellular domain of the ASGR1 receptor. To gauge the degree of uptake miRNA, the mEVs were internalized with mmu-miR-298-5p as a probe miRNA, since it is a mouse miRNA that is not known to affect human genes [67,68].

Materials and Methods

Cell culture

The human liver cancer HepG2 cells were purchased from American type culture collection (ATCC, Maryland, MD). HepG2 cells were grown and maintained in Eagle's minimum essential medium (EMEM) (Corning). Both the media were supplemented with 10% fetal bovine serum (FBS) (Atlanta Biologicals, Flowery Branch, GA) and 5% penicillin/streptomycin (Thermo Fisher, Waltham, MA), and the cells were incubated in a humidified atmosphere of 5% $CO_2$ at 37° C.

Anti-ASGR1 Antibody

Anti-Asialoglycoprotein Receptor 1/HL-1 antibody (ab49355) from abCAM, Product Number: ab49355.

miR-298-5p cargo having a sequence:

```
(miRBase Accession No. M10000398)
                      (SEQ ID NO: 3)
GGCAGAGGAGGGCUGUUCUUCCC
```

miRNA Delivery to HepG2 Cells by Functionalized Vesicles

The Abi-exosomes were bioengineered from exosomes, as described in the Examples above. The antibody used with the Abi-exosomes was the Anti-ASGR1 antibody, which specifically targets a receptor found on the surface of liver cells. Ten μl (3.8 μg) of mouse miR-298-5p were electroporated into the 3.8 μg Abi-exosomes or 3.8 μg exosomes using the Bio-Rad (Hercules, CA) at 150 v, 125 μF capacitance. Afterward, the Abi-exosomes exosomes were suspended in 400 μl serum-free Eagle's Minimum Essential Medium (EMEM) medium.

A six-well plate was plated to a concentration of 200,000 Hep-G2 cells/well. These Hep-G2 cells were serum-starved for 24 hours after they were adherent to the plate to ensure that all the cells were in the GI-arrest phase of the cell cycle. After 24 hours, the Hep-G2 cells were untreated, treated with the transfection reagent DharmaFECT (Thermo Fisher Scientific, Waltham, MA), treated with DharmaFECT and mouse miR-298-5p, treated with Abi-exosomes containing mmu-miR-298-5p, or treated with exosomes containing mouse miR-298-5p. The RNA was extracted 72 hours after the treatment using TRIzol Reagent (Invitrogen, Carlsbad, CA). Complementary DNA (cDNA) was prepared from intracellular RNA using the Taqman microRNA Reverse Transcription Kit for mmu-miR-298-5p (Thermo Fisher Scientific, Waltham, MA). The cDNA was then run in a 384-well format in a qRT-PCR assay using Taqman Universal PCR MasterMix (Thermo Fisher Scientific, Waltham, MA) and the ABI 7900HT machine (Applied Biosystems, Foster City, CA,). The qRT-PCR fluorescence results were analyzed using GraphPad Prism 7 and normalized against background fluorescence using control U6 small nuclear RNA (snRNA) and untreated cells.

Alternatively, cells were exposed to various combinations of miRNA, vesicles and modified vesicles to determine their uptake of miRNA. The cells were counted using a hemocytometer on a Zeiss Invertoskop 40 C inverted microscope (Xeiss, Oberkochen, Germany). The cells were plated to approximately 200,000 cells per well in a 6-well VWR tissue culture-treated plates (Radnor, PA) and incubated ~12 hours (overnight). Afterwards, the media was replenished with 2.7 mL of fresh 10% EMEM media. The cells were also serum starved for ~12 hours before treatment. For experiments with all vesicles, 400 μl of them were electroporated with ~3.5 μg miRNA were added to the 6-well plates. For experiments involving the DharmaFECT™ 4 transfection reagent, the wells were treated as per the manufacturer's instructions with an equivalent amount of miRNA and liquid volume in the wells. The final volume in all the wells was approximately 3 ml. Prior to RNA extraction, the treated plates were incubated for 72 hours under a humidifying conditions at 37° C. with 5% $CO_2$ in a Thermo Fisher Scientific Napco Series 8000 WJ $CO_2$ incubator (Thermo Fisher, Waltham, MA).

RNA Extraction and Quantitative RT-PCR (qRT-PCR)

TRIzol Reagent (Invitrogen, Carlsbad, CA) was used to isolate intracellular RNA as per the manufacturer's protocol. All RNA was stored at −80° C. Complementary DNA (cDNA) was prepared from intracellular RNA (i.e., microRNA and the housekeeping U6 small nuclear (snRNA)) using the TaqMan™ microRNA Reverse Transcription Kit (Thermo Fisher Scientific, Waltham, MA). The cDNA was analyzed on an Applied Biosystems 7900HT Fast Real-Time PCR System (Applied Biosystems, Foster City, CA) in a 384-well microplate with the TaqMan™ Universal PCR MasterMix (Thermo Fisher Scientific, Waltham, MA). For measurements of miRNA transfer efficiency, TaqMan™ MicroRNA assay (Thermo Fisher Scientific, Waltham, MA) kits with specific fluorescent cDNA primers for the miRNA (human and mouse) and fluorescent cDNA primers for the U6 snRNA reference. The DNA was quantitated on the qRT-PCR instrument using the threshold cycle (CT) method using the DNA related to the U6 snRNA gene as a reference to calculate $\Delta\Delta C_T$ values, which correlates to the relative miRNA yield [42-45]. This was exported into Microsoft Excel format to calculate fold difference and analyzed in GraphPad Prism 7 (GraphPad, San Diego, CA). The $\Delta\Delta C_T$ values were normalized against a condition of interest in the figures to indicate the relative amount of miRNA delivered to the cells for the purpose of making comparisons of the relative miRNA expression levels.

In-Vitro Time Course for miRNA Uptake

To determine the real-time cargo release by the bioengineered vesicles in-vitro, six well VWR culture treated plates (Radnor, PA) were plated with HepG2 cells at a density of 100,000 cells/well counted using a hemocytometer on a Zeiss Invertoskop 40 C inverted microscope (Xeiss, Oberkochen, Germany). After the cells adhered, the cells were serum-starved for one day. The next day, the cells were treated with functionalized vesicles containing 3.8 μg of mmu-miR-298-5p. Before extracting RNA, the cells were incubated for 12 h, 24 h, 36 h, 48 h, and 72 h in a humid atmosphere at 37° C. with 5% $CO_2$ in a Thermo Fisher Scientific Napco Series 8000 WJ $CO_2$ incubator (Waltham, MA).

RNA was extracted using TRIzol reagent (Invitrogen, Carlsbad, CA) as per the manufacturer's protocol. MiRNA and U6 snRNA, the endogenous control, was quantified using the TaqMan™ microRNA reverse transcription (Thermo Fisher Scientific, Waltham, MA) and the TaqMan™ Universal PCR MasterMix (Thermo Fisher Scientific, Waltham, MA). The TaqMan™ microRNA assays are specifically designed to extend the 3' prime ends of the target to produce a template which is then polymerized and analyzed using a standard TaqMan real-time PCR. The 384 micro-plate is read on an Applied Biosystems 7900HT Fast Real-Time PCR System (Applied Biosystems, Foster City, CA) using the cycle threshold ($C_T$) method. The $AC_T$ values were calculated by normalizing the CT values to the endogenous control (U6 housekeeping snRNA). The baseline of ACT values is corrected with respect to the untreated control to give $AAC_T$ values, converted to fold difference, and analyzed in Microsoft Excel (Microsoft, Redmond, WA) and GraphPad Prism 7 (GraphPad, San Diego, CA).

Results

Abi-exosomes were bioengineered with the anti-asialoglycoprotein receptor 1/HL-1 (Anti-ASGR1) antibody to target hepatocytes. The efficiency of these Abi-exosomes to deliver microRNA (miRNA) to hepatocytes was determined with the mouse 5' miRNA called mmu-miR-298-5p, which will suppress mouse P-glycoprotein (Pgp) expression (Xie, et al., *Front. Neurosci.* 12 (2018), doi.org/10.3389/fnins.2018.00602. Haenisch, et al., *Br. J. Clin. Pharmacol,* 77: 587-596 (2014) doi.org/10.1111/bcp.12251, Bao, et al., Targeted gene therapy of ovarian cancer using an ovarian-specific promoter, *Gynecol. Oncol.* 84: 228-234 (2002). doi.org/10.1006/gyno.2001.6490), in the immortalized human liver carcinoma cells called Hep-G2 cells (Donato, et al., *Methods Mol. Biol.* Clifton NJ. 1250: 77-93 (2015). doi.org/10.1007/978-1-4939-2074-7_5). Using mouse mmu-miR-298-5p to determine the efficiency of miRNA transfer to human hepatocytes is advantageous because Hep-G2 cells do not express mouse Pgp and are therefore insensitive to miR-298-5p. These experiments also demonstrate the potential for in vivo targeting of Pgp in the mouse liver.

Figure 6A:
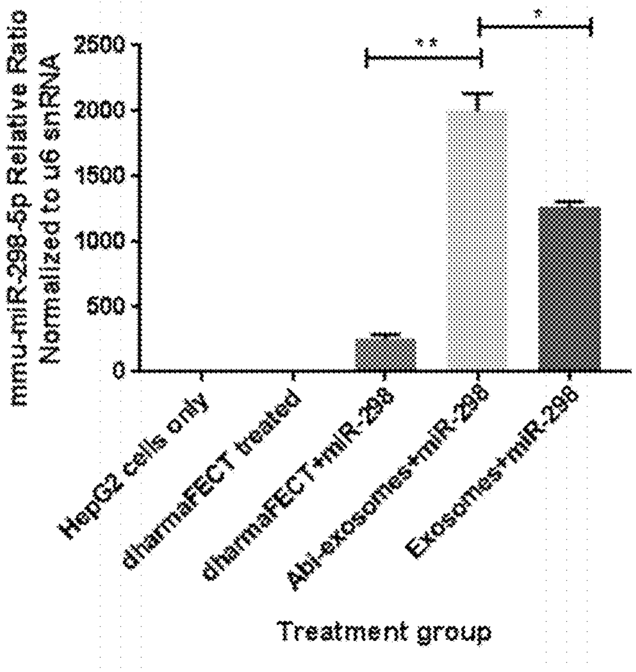
FIG. 6A is a bar graph showing the efficiency of mmu-miR-298-5p incorporation into Hep-G2 cells determined from qRT-PCR analysis. The columns from left to right: Hep-G2 cells only (Cells Only); Hep-G2 cells and DharmaFECT (DharmaFECT only); Hep-G2 cells, 3.8 μg mmu-miR-298-5p, and DharmaFECT (miR-298); Abi-exosomes with the anti-ASGR-1 antibodies and miR-298-5p (Abi-exosomes+miR-298); exosomes with mmu-miR-298-5p (Exosomes+miR-298). The column values represent an average, and the error bars represent the standard deviation from quadruplicates. Statistics: ** p-value<0.01; * p-value<0.05.

FIG. 6A shows the relative ratio determined from quantitative real-time PCR (qRT-PCR) analysis of mouse mmu-miR-298-5p compared to the control Hep-G2 cells. The far two left columns are the negative controls. In the far left column, the Hep-G2 cells were untreated and demonstrate an absence of mouse mmu-miR-298-5p. The column to the right of this column shows mmu-miR-298-5p produced from qRT-PCR analysis in Hep-G2 cells with DharmaFECT, which is a transfection reagent. Again, qRT-PCR analysis of Hep-G2 cells treated only with DharmaFECT did not detect the nucleic acid of interest, which demonstrates they lack mmu-miR-298-5p. In the next column, adding rat mmu-miR-298-5p and DharmaFECT to Hep-G2 cells produced a relative quantitative amplification of the nucleic acid of 254.4±32.1, indicating significant incorporation of 3.8 μg mouse mmu-miR-298-5p into Hep-G2 cells. The next column shows the results of incorporating mmu-miR-298-5p into Hep-G2 cells, facilitated by the hepatocyte targeting of Abi-exosomes. The relative quantification was about 8-fold greater than samples utilizing DharmaFECT or 2001.2±134.8, showing that Abi-exosomes can more efficiently incorporate 3.8 μg of mmu-miR-298-5p. In contrast, the relative ratio of mmu-miR-298-5p reflecting miR incorporation into exosomes not containing anti-ASGR1 (hepatocyte-targeting) antibodies is shown on the far right. The relative ratio normalized to control was 1266.8±40.1, indicating that the exosomes were only half as efficient as Abi-exosomes at incorporating 3.8 μg of mmu-miR-298-5p.

Figure 6B:
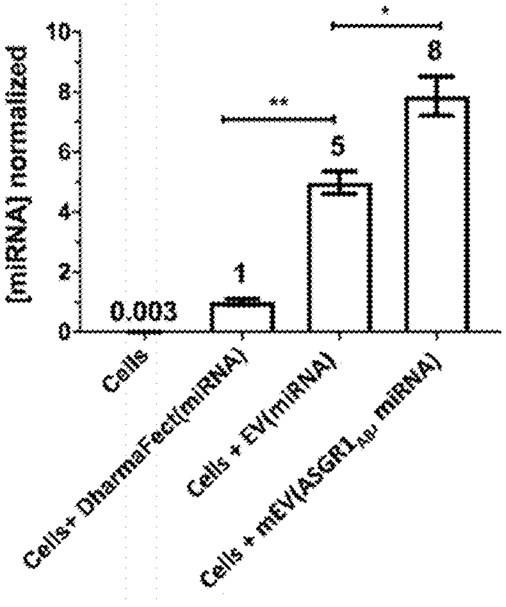
FIG. 6B is also a bar graph showing relative uptake efficiency of miRNA into HEPG2 cells treated with DharmaFect 4, EVs, mEVs, and mLNPs and Time release profile of mmu-miR-298 by mEVs and mLNPs. The conditions are described: Cells: untreated HEPG2 cells; Cells+Extracellular vesicles (Evs): HEPG2 cells treated with unmodified exosomes; Extracellular vesicles(miRNA): Exosomes electroporated with probe miRNA; Cells+DharmaFect(miRNA): HEPG2 cells treated with DharmaFect 4 and the probe miRNA; Cells+Abi-exosomes(ASGR1, miRNA): HEPG2 cells treated with Modified EVs bioengineered with the ASGR1 antibody and containing miRNA. The columns were normalized against the intracellular miRNA concentration of DharmaFect 4 treated cells.

See also FIG. 6B. The results shown in FIG. 6B were also used to gauge the uptake of 3.8 μg of mmu-miR-298-5p into the HEPG2 cell line using various treatments. As in FIG. 6A, for the purpose of comparison, the relative uptake of mmu-miR-298-5p were normalized against HEPG2 cells treated with DharmaFect 4 transfection reagent with 3.8 μg miRNA (DharmaFect(miRNA)). Effectively none of the miRNA was detected in untreated miRNA cells. This graph shows relative uptake efficiency was 5-fold higher in HEPG2 cells treated with EVs electroporated with mmu-miR-298-5p (EV (miRNA)). Constructing mEVs with the ASGR1 Ab improved uptake efficiency by 60% (mEV(ASGR1$_{PAB}$, miRNA). The improvement of uptake efficiency is about a third of the mRNA uptake by HEPG2 cells treated with exosomes genetically engineered with an Apolipoprotein A1 targeting ligand [36]. The reduced miRNA uptake may be due to the requirement that receptor-mediated endocytosis requires the interaction of all extracellular domains within the ASGR1 receptor trimer [62]. In contrast, the internalization of exosomes with an Apolipoprotein A1 targeting ligand only requires binding to a single monomer of the scavenger receptor, class B, type I (SR-BI) for internalization, although the receptor can form clusters [62,69,70].

Figure 6C:
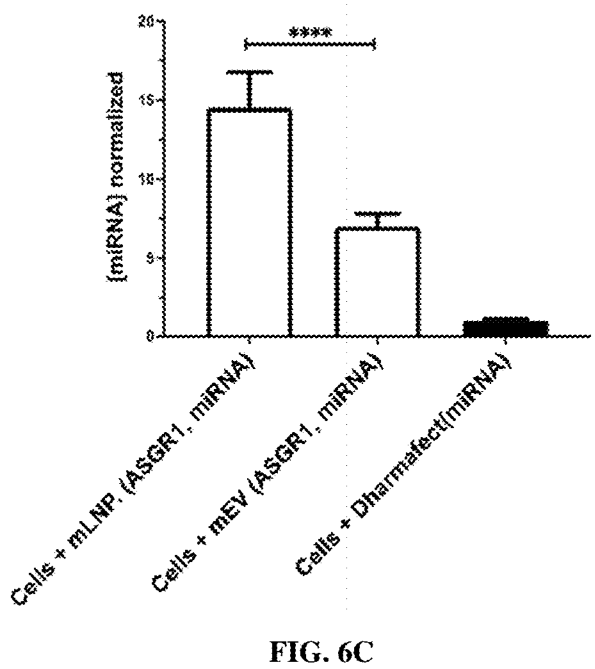
FIG. 6C is a bar graph showing the relative ratio of miR-298-5p delivered in HepG2 cells treated by mLNPs (open) and mEVs (grey) in comparison to the untreated cells (black). The data was normalized to U6 and expressed as mean±SD (****p<0.0001).

Modified LNPs with AGR1PAB were also made and loaded with 3.8 μg mmu-miR-298 (mLNP(ASGR1$_{PAB}$, mmu-miR-298)) as a probe miRNA. FIG. 6C shows the relative miRNA uptake by HepG2 cells treated with mLNPs (ASGR1$_{PAB}$, mmu-miR-298). For the purpose of comparison, HepG2 cells were also treated with mEVs(ASGR1$_{PAB}$, mmu-miR-298). The miRNA uptake was normalized against the miRNA present in cells treated with DharmaFECT4 (mmu-miR-298). Relative uptake was almost 2-fold higher in cells treated with mLNPs (ASGR1$_{PAB}$, mmu-miR-298) in comparison to those treated with mEVs (ASGR1$_{PAB}$, mmu-miR-298). The mLNPs may have more functionalized lipids than mEVs as indicated by the DLS experiments. The miRNA delivery by mLNPs (ASGR1$_{PAB}$, mmu-miR-298) in comparison to the untreated group (500 fold) was significantly higher than the delivery of miR-7 by the cationic liposomes (60-fold) in ovarian cancer cells [71].

Figure 6D:
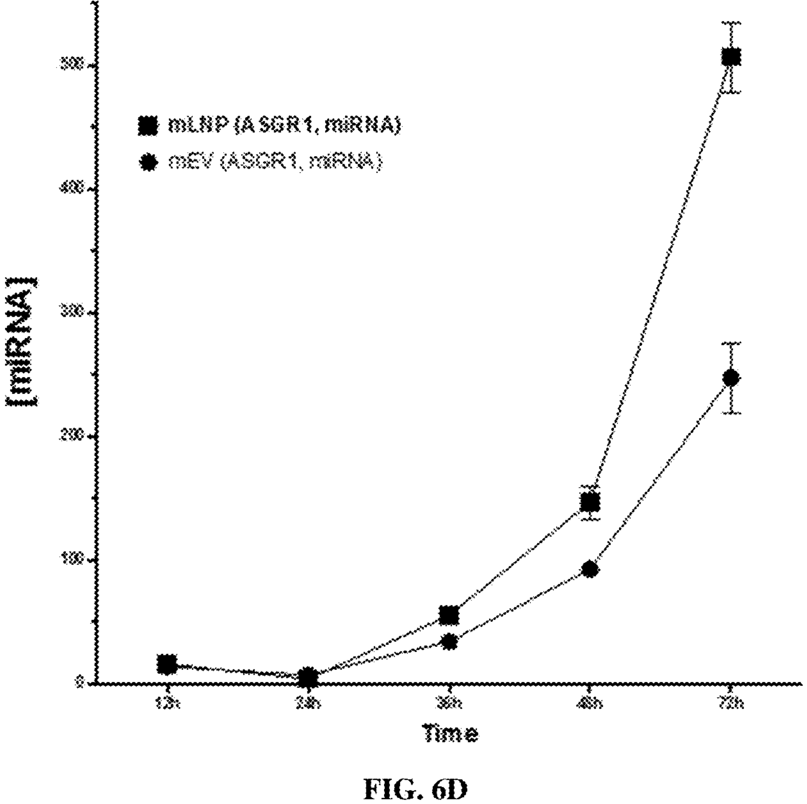
FIG. 6D is a bar graph showing the relative amount of miRNA delivered by mEVs and mLNPs to cells when harvested at different time points: 12, 24,36,48, and 72 hours. The levels were normalized against the endogenous levels of miRNA present in untreated cells.

Along with delivery efficiency analysis at 72 h, it was also important to analyze the miRNA delivered by the modified vesicles at time periods leading to 72 h to evaluate the time-release profile of miRNA at 12 h, 24 h, 36 h, 48 h, 72 h. An exponential increase in miRNA uptake was observed with almost 146-fold delivery by mLNPs (ASGR1$_{PAB}$, mmu-miR-298) and 92-fold delivery by mEVs(ASGR1$_{PAB}$, mmu-miR-298) at 48 h when compared to the untreated cells (FIG. 6D). The delivery spiked after 48 hours, reaching to 500-fold efficiency by mLNPs and 250-fold efficiency by mEVs at 72 h. Both mEVs and mLNPs showed a parallel increase in miRNA uptake efficiency. Because the miRNA increase was exponential, maximal miRNA uptake efficiency was not reached. In previous studies, maximal uptake efficiency was reached between 48 and 72 hours [71-75].

Example 6: Dynamic Light Scattering (DLS) Technique Reveals that the "Detergent-Dialysis Method" has Significant Effects on the Size of Modified Vesicles Versus the "Functionalized Lipid Insertion Technique"

Abbreviations, as used herein, particularly in Examples 6-12, and FIGS. 6B-15C, and their descriptions:

Ab, antibody; Ct, cycle threshold; CMC, critical micelle concentration; EV, extravascular vesicle; FA, fatty acid; HepG2, human liver cancer cell line; HCC, hepatocellular carcinoma; LNP, liposomal nanoparticle; miR, microRNA; miRNA, microRNA; mEV, modified extravascular vesicle; mLNP, modified liposome; PBS, Phosphate-Buffered Saline.

Materials and Methods

Cell Culture

Human donors were enrolled for blood collection in compliance with the World Medical Association's Declaration of Helsinki and the Human Research Protection Program and Institutional Review Board guidelines for human subject research at the University of Georgia. Enrolled healthy volunteers signed consent forms to inform them about the study. The human blood protocol (University of Georgia IRB no STUDY00006632) and the consent form were reviewed and approved by the Institutional Review Board of the University of Georgia.

The human liver cancer HepG2 cells were purchased from American type culture collection (ATCC, Maryland, MD). HepG2 cells were grown and maintained in Eagle's minimum essential medium (EMEM) (Coming). Both the media were supplemented with 10% fetal bovine serum (FBS) (Atlanta Biologicals, Flowery Branch, GA) and 5% penicillin/streptomycin (Thermo Fisher, Waltham, MA), and the cells were incubated in a humidified atmosphere of 5% $CO_2$ at 37° C.

Materials and Reagents

Fatty acids for fatty acid label, 1,2-distearoyl-sn-glycero-3-phosphoethanolamine-N-[maleimide(polyethylene glycol)-2000](DSPE-PEG2000-maleimide), and fluorescent 1,2-distearoyl-sn-glycero-3-phosphoethanolamine-N-(7-nitro-2-1,3-benzoxadiazol-4-yl) (NBD-DSPE) were purchased from Avanti Polar lipids (Alabaster, AL). HEPES (4-(2-hydroxyethyl)-1-piperazineethanesulfonic acid), n-dodecyl-p-D-maltoside (DDM) detergent, and Histopaque 1077 Reagent were purchased from Sigma Aldrich (St. Louis, MO). For the construction of liposomal nanoparticles (LNPs), *Escherichia coli* (*E. coli*) polar lipid extract was ordered from Avanti Polar lipids (Alabaster, AL), and chloroform was acquired from Sigma Aldrich (St. Louis, MO). Anti-Asialoglycoprotein receptor 1 (ASGPR1)/HL-1 antibody (ab49355) and Recombinant anti-ACE2 antibody (ab108252) was acquired from abCAM (Cambridge, MA). Anti-NPHS2 (podocin) polyclonal antibody (MBS3013144) was acquired from MyBioSource (San Diego, CA). GFP monoclonal antibody (GF28R) (MA5-15256) and VDR Monoclonal Antibody (9A7) (MA1-710) were obtained from Therno Fisher (Waltham, MA).

MiRNA mimics (mmu-miR-298-5p (0.38 mg/ml), hsa-miR-26a-5p (0.28 mg/ml)), and TaqMan™ MicroRNA assay were ordered from Thermo Fisher Scientific (Waltham, MA). Six ml Becton, Dickinson, and Company (BD) (Franklin Lakes, NJ) hematological tubes spray-coated with 1.8 mg/ml of dipotassium ethylene diamine tetraacetic acid (EDTA), and the blood separation agent Histopaque® 1077 Reagent, which is a solution of polysucrose and sodium diatrizoate (1.077 g/mL), was obtained from Sigma-Aldrich (St. Louis, MO). DharmaFECT™ 4 transfection reagent, which has been validated for many cell types, was bought from Horizon (Cambridge, UK).

Isolation of Extracellular Vesicles (EVs)

Approximately, 10 ml of human blood were put into EDTA-coated BD hematological tubes to declot them. The PBMCs were isolated as described with some modifications [31]. Five ml of EDTA-treated blood samples were layered onto an equal amount of Histopaque® 1077 Reagent in a 15 ml conical tube. The tube was centrifuged at approximately 400 g (1478 rpm) for 30 minutes and 4° C. in an Eppendorf 5810R centrifuge (Hamburg, Germany), which separated the blood into plasma, PBMC, and erythrocyte layers. The top plasma layer is removed and discarded. The turbid middle layer of PBMCs was removed and put into a clean 15 ml conical tube. The tube was centrifuged at approximately 450 g (1917 rpm) for 10 minutes at 4° C. The supernatant was carefully removed using a transfer pipette. The resulting PBMC pellet was washed with 5 ml of an isotonic Phosphate-Buffered Saline (PBS) (137 mM NaCl, 2 mM KCl, 10 mM $Na_2HPO4$, 1.8 mM $KH_2PO4$) solution and centrifuged twice at 300 g (1278 rpm). This pellet was suspended in RPMI growth media without glutamine, and phenol red (Corning, NY, USA [32]) and added a 1M HEPES buffer solution (pH 7.4) to a final concentration of 25 mM HEPES to provide additional buffering capacity for the media. Cells were then transferred to a sterile Cellstar T-75 culture flask with a red filter screw cap containing RPMI (with glutamine and phenol red) supplemented with 10% fetal bovine serum (FBS) and penicillin/streptomycin. This solution was incubated about −12 hours (overnight) in a humidified atmosphere at 37° C. and 5% $CO_2$ in ThermoFisher Scientific Napco Series 8000 WJ $CO_2$ incubator (Waltham, MA). Afterward, the media was transferred with a sterilized transfer pipette into 2 ml microcentrifuge tubes. The microcentrifuge tubes were centrifuged at 10,000 g (~14,000 rpm) for 5 min. on a table top centrifuge at room temperature. About 1 ml of supernatant from each microcentrifuge tube was transferred to a new 2 ml microcentrifuge tube. Four hundred microliters of precipitation buffer B from the Qiagen (Formerly, Exiqon) miRCURY Exosome Isolation Kit (Qiagen, Germantown, MD) was added to the supernatant in each tube. The microcentrifuge tubes were inverted and vortexed and allowed to incubate −12 hours (overnight) at 4° C. The longer incubation time improved the EVs yield from the PBMCs. The remaining steps follow the manufacturer's instructions for the Qiagen miRCURY Exosome Isolation Kit. The EVs were resuspended in 300 ml of the resuspension buffer supplied by the kit, combined in one tube, and stored at −80° C. until needed. The total protein concentration of the EVs was measured using the Pierce Bicinchoninic Acid (BCA) Protein Assay Kit (Thermo Fisher Scientific, Waltham, MA) to estimate the concentration and the yield, which was ~10 μg.

Preparation of Liposomal Nanoparticles (LNPs)

Unilamellar liposomal nanoparticles (LNPs) were prepared using the filter extrusion method [33]. The LNPs were composed of 80% w/v *E. coli* Avanti polar lipids with a defined lipid profile and 20% w/v cholesterol as described previously [34]. Briefly, lipids and cholesterol were mixed in 10 ml chloroform to get a final concentration of 10 mg/ml. This solution was evaporated to dryness in a Rotavapor Model R-114 (Buchi). After evaporation, the film was reconstituted in 0.1 mM EGTA and 50 mM Tris/HCl. This suspension was freeze-thawed at least ten times using liquid nitrogen and extruded 11 times through a LIPEX extruder (Northern Lipids) with a 400 nm cutoff Millipore filter (EMD Millipore).

Functionalized Vesicles Produced by the "Functionalized Lipid Insertion Method"

A 200 μl solution isotonic PBS solution containing a 100 μM of fluorescent NBD-DSPE, a 100 M of DSPE-PEG2000-maleimide, 0.1% w/v DDM detergent (10X the critical micelle concentration (CMC)) was made and will be referred to as FA solution. The NBD-DSPE fluorescence was monitored at 550 nm by exciting at 445-460 nm using a SpectraMax M2 Plate Reader (Molecular Devices, Sunnyvale, CA) to track FA insertion and to monitor EVs and LNPs assembly. To remove excess DDM detergent, the FA solution was dialyzed using 0.5 mL Slide-A-Lyzer MINI Dialysis units with a 10 KD cut-off filter (Thermo Fisher Scientific, Waltham, MA) against 2 L isotonic PBS for 2 h at 4° C. Almost identical fluorescence for the NBD-DSPE was measured after dialysis showing that the lipids remained in solution. To ensure that all DSPE-PEG2000 maleimide were conjugated, two-fold excess the targeting antibody (-200 M) was added to the dialyzed FA solution and incubated at room temperature for 1 hour. A 100 μl of purified 10 mg/ml EVs or LNPs were added to this 200 μl of the NBD-DSPE and DSPE-PEG2000-Antibody solution and briefly centrifuged. The molar ratio of vesicle lipid to NBD-DPSE and DSPE-PEG2000-Antibody was approximately 75:1:1. This 300 μl solution was incubated for 1 hour at room temperature to allow slow mixing and to prevent any potential disruption of the vesicles. After incubation, the solution was dialyzed in a 0.5 mL 10 KD cut-off Slide-A-Lyzer MINI Dialysis unit against 2 L of isotonic PBS buffer for two hours at 4° C. Dialysis slowly removes DDM detergent that is surrounding and solubilizing the FAs. The exposed FA hydrophobic surfaces entropically drive the FA ends of DSPE-PEG2000-Antibody and NBD-DPSE into the vesicle bilayer to minimize their exposure to water to form functionalized vesicles. A similar procedure has been used for directionally inserting a membrane protein transporter into a liposome bilayer, whose directional orientation was confirmed enzymatically and through atomic force microscopy (AFM) [52,53]. Afterward, the mEV solution was incubated with 100 μl of precipitation buffer B from the Qiagen miRCURY Exosome Isolation Kit for −12 hours (overnight) at 4° C. (Final volume=−250 ml), and the mLNPs solution was centrifuged at 14,000 rpm for 30 minutes to obtain a pellet. To pellet the mEVs, the solution was centrifuged at 104,000 g (30,472 rpm) in a Beckman TLA 110 rotor for one hour at 20° C. in a Beckman TLX ultracentrifuge. The supernatant was carefully removed, and the mLNP/mEV pellet was suspended in 100 ml isotonic PBS, which will be called the functionalized vesicle solution. The purpose of centrifuging the functionalized vesicles and removing the supernatant is to remove any remaining antibodies that have not been cross-linked to the DPSE-PEG2000-Maleimide FA. The concentration of mEVs was measured by protein quantification using Pierce Bicinchoninic Acid (BCA) assay, and concentration of mLNPs was determined by tracking the amount of the lipid that was used throughout the experiments.

Functionalized Vesicles Produced by the "Detergent-Dialysis Method."

The production of modified vesicles by the "Detergent-Dialysis Method" was done as previously described [16-23]. Basically, the lipids, proteins if present, and the derivatized lipids are dissolved in detergent several times higher than the CMC [16-23]. These solutions are then extensively dialyzed to remove the detergent [16-23]. The dialysis-driven detergent removal process causes the lipids, the proteins, and the derivatized lipids randomly form into modified vesicles of indeterminate sizes [16-23]. Differences between this method and the "Functionalized Lipid Insertion Method" are described in the text and FIGS. 7A-7D and 8A-8B.

Lipids functionalized with antibodies (i.e., FA-PEG2000-Antibody) were made as described above. About a milligram of the following mixtures were mixed at three times the CMC of DDM (0.03%) following procedures similar to [16]. 1) *E. coli* Avanti polar lipids to form liposomes. 2) *E. coli* Avanti polar lipids, NBD-DSPE, and DSPE-PEG2000-Antibody with molar ratios of 75:1:1. 3) PBMC-derived EVs to form EV-derived liposomes. 4) PBMC-derived EVs, NBD-DSPE, and DSPE-PEG2000-Antibody with molar ratios of 75:1:1. The solutions in 200 1 Eppendorf tubes were sonicated in a Kendal ultrasonic cleaner HB23 (Kendal) at 25° C. until the solutions clarified indicating that the components had been completely dissolved by detergent. The mixtures were then dialyzed extensively as described [16] by putting 50 1 of them into 0.2 mL Slide-A-Lyzer MINI Dialysis units with a 10 KD cut-off filter (Thermo Fisher Scientific, Waltham, MA) against 2 L isotonic PBS for at least 45 hours at room temperature.

Characterizing Functionalized Vesicles

Dynamic light scattering (DLS) was used to characterize extracellular vesicles (EVs), liposomal nanoparticles (LNPs), modified extracellular vesicles (mEVs), and modified liposomal nanoparticles (mLNPs) to determine the effects of the "Detergent-Dialysis Method" and the "Functionalized Lipid Insertion Method" on the size of the functionalized vesicles (FIGS. 9A-9E). DLS is a well-established technique to analyze the size distribution of nanovesicles such as EVs and LNPs [35-39]. The DLS experiments were performed on a Malvern Zetasizer Nano ZS (Malvern Panalytical, Malvern, UK) using a Malvern 45 ml ultra-micro cuvette (ZEN2112). Prior to analyzing the samples using DLS, all samples were centrifuged at ~21,000 g (14,000 rpm) for 30 min. using a Microfuge™ 22R (Beckman Coulter, Brea, CA) at 4° C. The DLS experiments were analyzed using the Zetasizer Software Version 8 (Malvern Panalytical, Worcestershire, United Kingdom), assuming refractive index of 1.330 and a viscosity of 0.8872, which are parameters typically used for lipid-containing vesicles [40]. The size distribution curves in this manuscript were rendered on Igor Pro 6.3 (WaveMetrics, Portland, OR). Protein concentrations of the EVs were determined using Pierce Bis-cinchonic assay kit (BCA) and of LNPs was determined by tracking the lipid concentration throughout the experiments.

Statistics

One-way analysis of variance (ANOVA) test were used to determine statistical significance between groups comparing relative miRNA expression. A confidence interval of 95% with all p-values less than 0.05 was considered significant (*). Student's T-Test was also used to compare two groups to one another, also with a 95% confidence interval. Data was analyzed with Microsoft Excel (Microsoft, Redmond, WA) and GraphPad Prism 7 (GraphPad, San Diego, CA).

Results

The DLS technique is a well-established method for estimating the sizes of different particles based on their dynamic scattering properties [54]. The technique has been used to estimate the size distribution of vesicles, including EVs and LNPs [38,55]. The DLS technique is used here to determine the differences in modified vesicles produced through the "Detergent-Dialysis Method" and the "Functionalized-Lipid Insertion Method." Because mEVs and mLNPs are assembled all at once with the "Detergent-Dialysis Method," experiments were designed to determine if there would be significant changes in the size distribution of modified vesicles determined by the initial components in the detergent mixture.

Figures 9A, 9B, 9C, 9D, 9E:
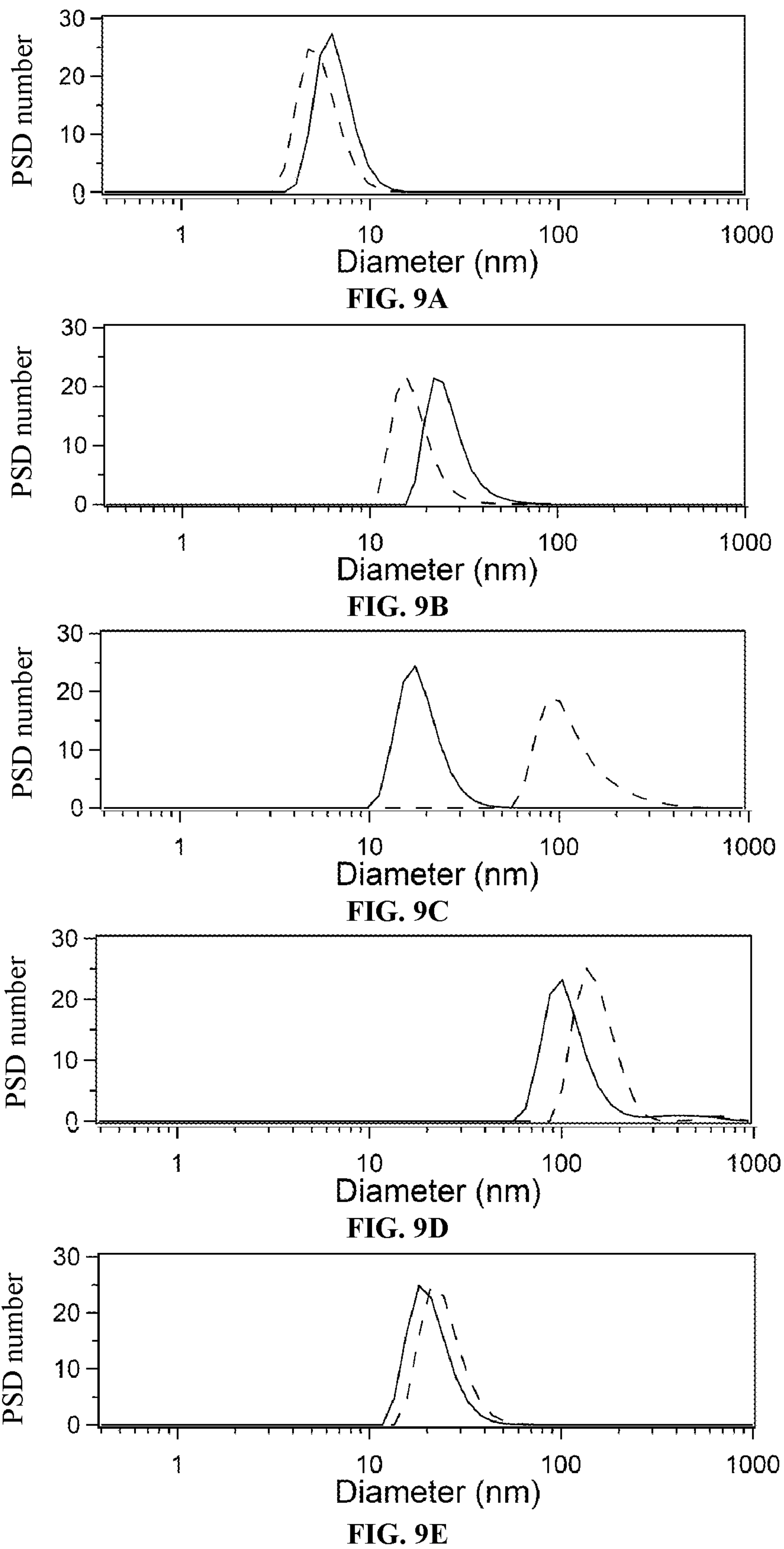
FIGS. 9A-9E are plots showing the percent size distribution (PSD) number of functionalized vesicles determined by dynamic light scattering (DLS). Detergent DDM micelles (solid line) and DDM-solubilized FAs (dashed line) (9A). The "Detergent-Dialysis Method" was used (9B) to produce the distributions of LNPs (solid line) and mLNPs (dashed line) and (9C) to produce the distributions of EVs (solid line) and mEVs (dashed line) line. The solid lines in panels (9D) and (9E) show the PSD distributions produced for LNPs using the extrusion approach [2], and EVs through isolation and purification protocols. The dashed lines in panels (9D) and (9E) show the distributions produced for mLNPs and mEVs using the "Functionalized Lipid Insertion Method." The FAs shown in panel 9A are NBD-DSPE and DSPE-PEG2000-maleimide.

FIGS. 9A-9E shows DLS measurements of functionalized vesicles produced by the two methods. The predominant particle size was determined in each of the solutions by comparing the particle size distribution (PSD) to the diameter in nm. FIG. 9A shows the negative controls with the predominate DDM micelle size (solid line) and a detergent-solubilized NBD-DSPE or DPSE-PEG2000-maleimide micelle size (dotted line) present in solution. The DDM micelle was 6.8±1.6 nm in diameter, while the detergent-solubilized FAs were slightly smaller at 5.7±1.4 nm, which is consistent with the sizes that you would expect for these molecules.

FIGS. 9B and 9C show vesicles produced using the "Detergent-Dialysis Method." The LNP (solid line) had an average diameter of 87.8±34.7 nm, which is similar to previous observations [19]. mLNP (dotted line) had half the diameter of the LNP at 51.2±19.5 nm. This size difference indicates that the size of LNPs may be sensitive to their lipid compositions. FIG. 9C shows the EVs (solid line) and mEVs (dotted line) produced using the "Detergent-Dialysis Method." The EVs produced using this method had an average size of 19.7±5.6 nm. In contrast, the diameter of mEVs increased 6-fold to 131±64.5 nm showing that the presence of functionalized lipids during dialysis significantly altered its size.

FIG. 9D and FIG. 9E show the unmodified vesicles and modified vesicles produced using the "Functionalized-Lipid Insertion Method" described in this manuscript. FIG. 9D shows the average particle size of LNPs that are unmodified (solid line). They have an average diameter of 115.6±35.0 nm. LNPs modified using the "Functionalized-Lipid Insertion Method" (dotted line) increased a little over 30% to 160.3±37.4 nm. A 40 nm increase in diameter is consistent with the length of a PEG2000 and IgG antibody sticking outside of the mLNP [56,57]. The unmodified EVs shown in FIG. 9E (solid line) was 21.2±5.9 nm, which is similar to the size of EVs processed with the "Detergent-Dialysis Method" (FIG. 9C, dotted line). In FIG. 9E (dotted line), the EVs increased only 17% or 5 nm to 24.7±6.9 nm. Because EVs have a considerable number of intrinsic membrane proteins, one possibility is that less of the functionalized lipid (i.e., DPSE-PEG2000-Antibody) was able to integrate into the EV because there is less space in the lipid bilayer to accommodate the functionalized lipid. Changes in the modified vesicle size were relatively modest with mEVs and mLNPs created by the "Functionalized Lipid Insertion Method" indicating that their original structures are largely intact.

Example 7: MEVs Reduce HepG2 Cell Proliferation by Enhancing Hsa-miR-26a-5p Uptake Materials and Methods Loading Functionalized Vesicles with miRNA Electroporation was used to load miRNA in the vesicles, as it is an efficient method to load oligonucleotides into vesicles [36,41]. Equal amounts of mEVs or mLNPs were added with an equal amount of miRNA mimics (Thermo fisher, Waltham, MA) in SFM for a total volume of 400 μl. The solution was put into a 0.4 cm gap Bio-Rad (Hercules, CA) electroporation cuvettes. Typical amounts of the miRNA, as well as the vesicles, varied between 1-3.8 mg in in-vitro experiments and 80-110 mg in in-vivo experiments. Samples were electroporated at 150 V, and 10-15 ms at exponential wave pulse in a Bio-Rad Gene Pulser X-Cell electroporator (Hercules, CA). Thereafter, the samples were incubated at room temperature and at 4° C. for 30 minutes to allow the vesicles to recover.

Results

The functional effects of treating HepG2 cells was tested with the mEVs(ASGR1pAB) and mLNPs(ASGR1pAB) loaded with miRNA hsa-miR-26a-5p. The miRNA Hsa-miR-26a-5p was chosen because it has a strong effect on cancer metastasis and growth by reducing cancer cell proliferation and cell death [36].

Wound healing assays with bright field microscopy have been shown to be an effective means to gauging cell proliferation and migration [76,77]. The approach was used to gauge the effect of mEVs and mLNPs treatment of HEPG2 cells in FIG. 10A. For untreated cells, the wound closure decreased almost in half meaning that cell proliferation was not inhibited. The cells treated with empty EVs, unmodified extracellular vesicles electroporated with hsa-miR-26a (i.e., EVs(hsa-miR-26a)) and empty modified extracellular vesicles with the polyclonal antibody for the ASGR1 receptor (i.e., mEV($ASGR1_{PAB}$)) had an almost similar extent of wound closure as the untreated cells meaning no effect on cell proliferation. The wound area for HepG2 cells after treatment with mEVs($ASGR1_{PAB}$, hsa-miR-26a) and mLNPs($ASGR1_{PAB}$, hsa-miR-26a) almost completely inhibited wound closure demonstrating the functional effect of hsa-miR-26a. Only the functionalized vesicles with miRNA had significant effects on HepG2 wound closure.

Figures 10A, 10B:
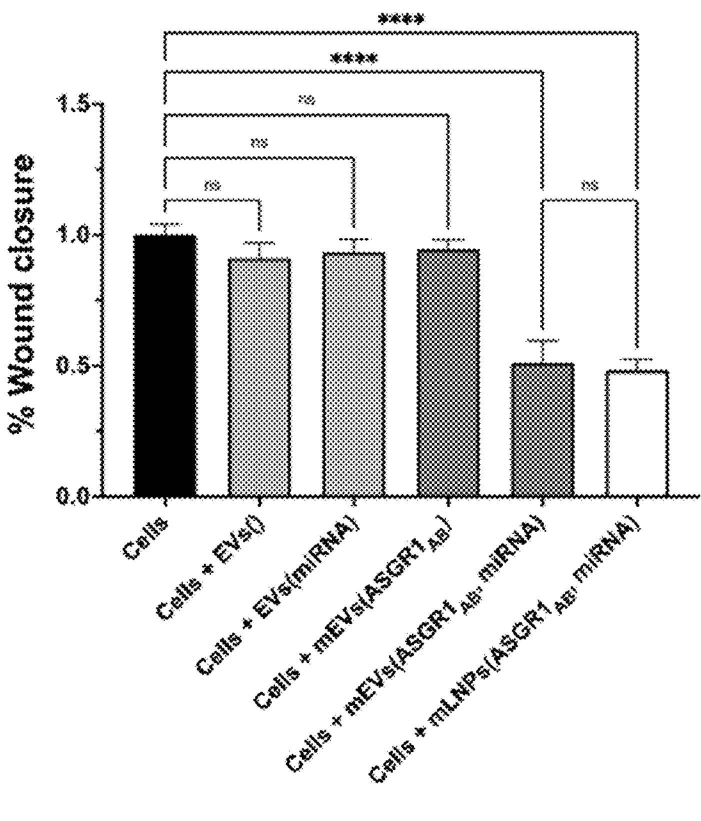
FIGS. 10A-10B are graphs showing the functional effects of hsa-miR-26a-5p in HEPG2 cells treated with mEVs ($ASGR1_{PAB}$).

This wound closure over the period of 72 hours was assessed quantitatively in FIG. 10A. The percent wound closure by all the treatment groups was normalized to the amount of wound healed in the untreated cells. The results show that relative amount of wound closure in the cells treated with empty EVs, EVs(hsa-miR-26a) and mEVs ($ASGR1_{pAB}$) was virtually identical to untreated cells. For EVs(hsa-miR-26a), the lack of effect on cell proliferation may be due to inefficient uptake of the hsa-miR-26a miRNA by the HepG2 cells. In contrast, wound closure by cells treated with mEVs(ASGR1PAB, hsa-miR-26a) or mLNPs (ASGR1pAB, hsa-miR-26a) inhibited cell proliferation by 50%.

Along with wound closure, relative wound area was also analyzed for three time points as shown in FIG. 10B. The wound in untreated HepG2 cells closed at a rate of 16±3%/day (bottom line, circles). This is close to the 19%/day wound closure observed for HepG2 closure treated with exosomes containing hsa-miR-26a (calculated from FIG. 10A in [36]). After 3 days, the wound area was reduced to 52±8% of the original area. The amount relative wound area in the cells treated with EVs delivering miRNA (i.e., EVs (hsa-miR-26a)) was reduced at the rate of 13.9±1.5%/day thus not differing significantly from untreated cells. Treating the HepG2 cells with mEVs(ASGR1PAB, hsa-miR-26a) decreased the rate of closure to 5±4.3%/day (diamonds) and with mLNPs($ASGR1_{PAB}$, hsa-miR-26a) decreased the rate of closure to 6.7±1.8%/day (triangles). Both the mEVs and mLNPs performed better than the wound closure inhibition observed for HepG2 cells treated with exosomes modified with the Apo A1 targeting ligand and containing hsa-miR-26a, which only decreased to 10%/day (calculated from FIG. 10A in [36]).

Example 8: Process of In Vivo Targeting of Modified Vesicles

Materials and Methods

Animal Studies

Eighteen Nu/Nu male nude mice, 48 Nu/Nu female nude mice for targeting studies, and 18 female C57/BL6 mice for immune reactivity studies were ordered from Jackson labs (Maine, USA). All mice were intraperitoneally (IP)-injected with a 25-gauge needle with 200 μl or 400 μl of solutions containing SFM or functionalized vesicles (i.e., mEVs or mLNPs) in SFM. Unless otherwise specified, each of the functionalized vesicles contained 114 g of mmu-miR-298 microRNA. All the mice were anesthetized using isoflorane (Milipore Sigma, Burlington, MA).

Figure 12A:
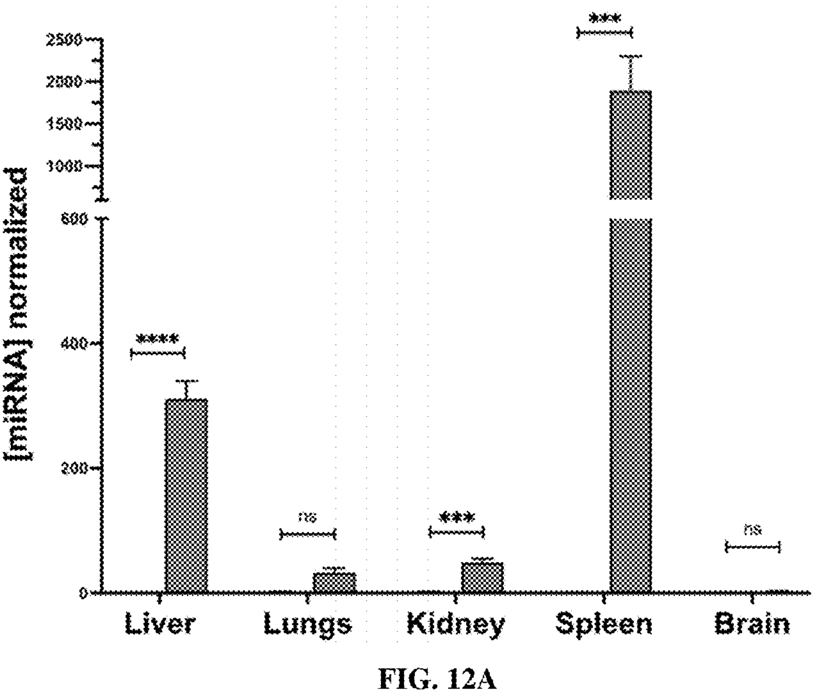
FIGS. 12A and 12B are bar graphs showing the uptake of miRNA in organs of mice treated with mEVs and mLNPs with non-targeting green fluorescent GFP antibodies. The relative-fold uptake of miRNA in the organs of mice treated with (12A) mEVs and (12B) mLNPs loaded with mmu-miR-298 and engineered with the GFP antibody (GFPAB) versus mice that were not treated (black) are shown. The data was normalized to the U6 housekeeping gene and expressed as mean±SEM (*p<0.001, **p<0.0001).
Figure 12B:
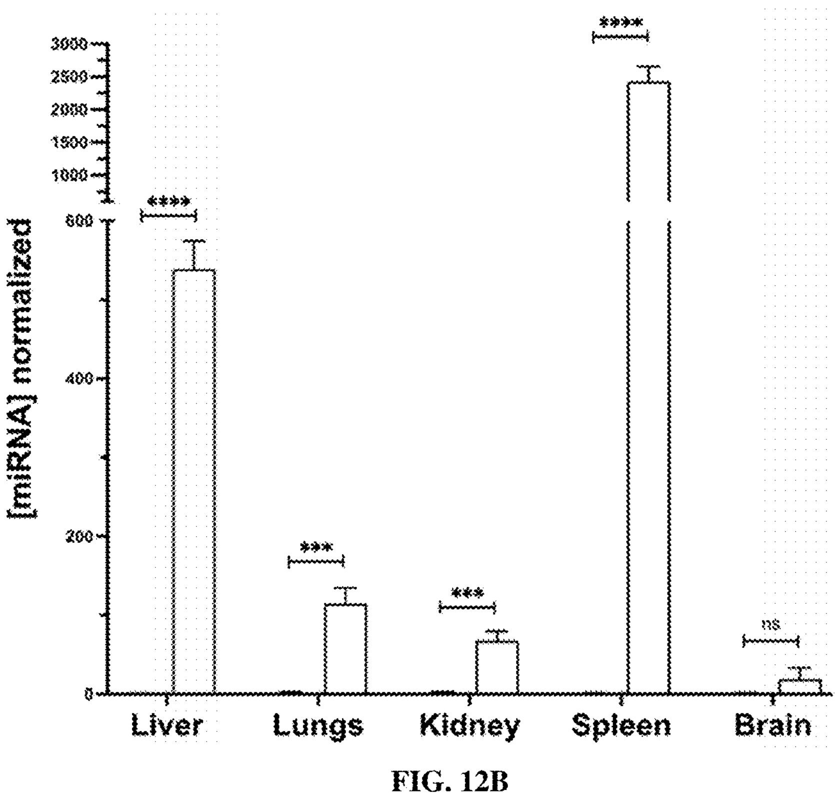

As a negative control, mEVs and mLNPs were bioengineered with the GFP monoclonal antibody ($GF28R_{MAB}$) since they are not known to interact with any mouse proteins (FIGS. 12A-12B). The functionalized vesicles are abbreviated mEV($GF28R_{MAB}$) and mLNP($GF28R_{MAB}$) to denote their modifications. In the experiment, 12 male Nu/Nu nude mice aged 5-7 weeks were divided into 3 groups (n=3). One group of mice were interperitoneally (IP)-administered 200 μl of SFM. The next two groups were IP-administered 200 μl mEVs($GF28R_{MAB}$) and mLNPs($GF28R_{MAB}$) electroporated with miRNA (i.e., mmu-miR-298). These functionalized vesicles are abbreviated mEV($GF28R_{MAB}$, mmu-miR-298) and mLNP($GF28R_{MAB}$, mmu-miR-298) to denote their modifications and their miRNA contents.

Figure 13A:
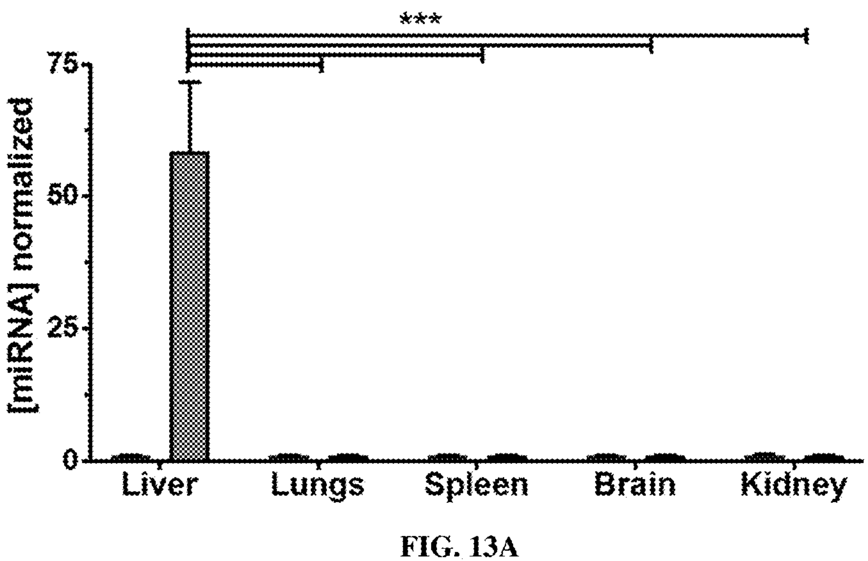
FIGS. 13A and 13B are bar graphs showing the targeting of mmu-miR-298 with the ASGR1 antibody in mice. The figures show the fold-difference of mmu-miR-298 uptake in various organs of mice after being treated with mEVs (n=3) (13A) and mLNPs (n=6) (13B) versus the serum free media control. The data was normalized to U6 and expressed as mean±SEM (**p<0.0001, *p<0.001, **p<0.01, *p<0.05). Injection volume: 250-300 ul.
Figure 13B:
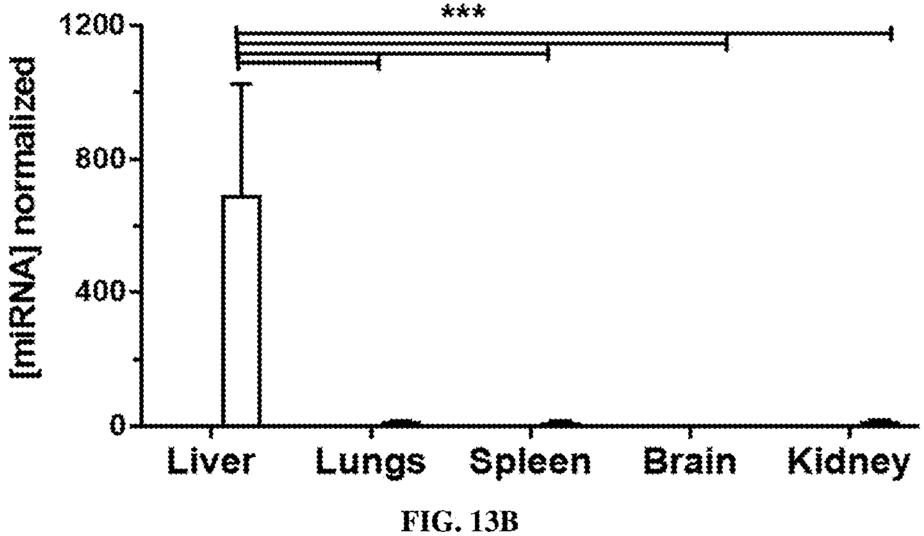

The targeting ability against the endocytotic liver ASGR1 receptor was tested with mLNPs and mEVs bioengineered with the ASGR1 polycolonal antibody ($ASGR1_{PAB}$) (FIGS. 13A-13B). For experiments involving mEVs($ASGR1p_{AB}$), six Nu/Nu male mice aged 15-17 weeks were randomly divided into two groups (n=3). For the experiments involving mLNPs($ASGR1^{PAB}$), 18 Nu/Nu female mice aged 5-8 weeks were divided into 3 groups (n=6). The mice then received IP injections with a total volume 400 μl per mouse. The solutions contained SFM only (untreated), mEVs ($ASGR1_{PAB}$, mmu-miR-298), or mLNPs($ASGRI_{PAB}$, mmu-miR-298).

Figure 14A:
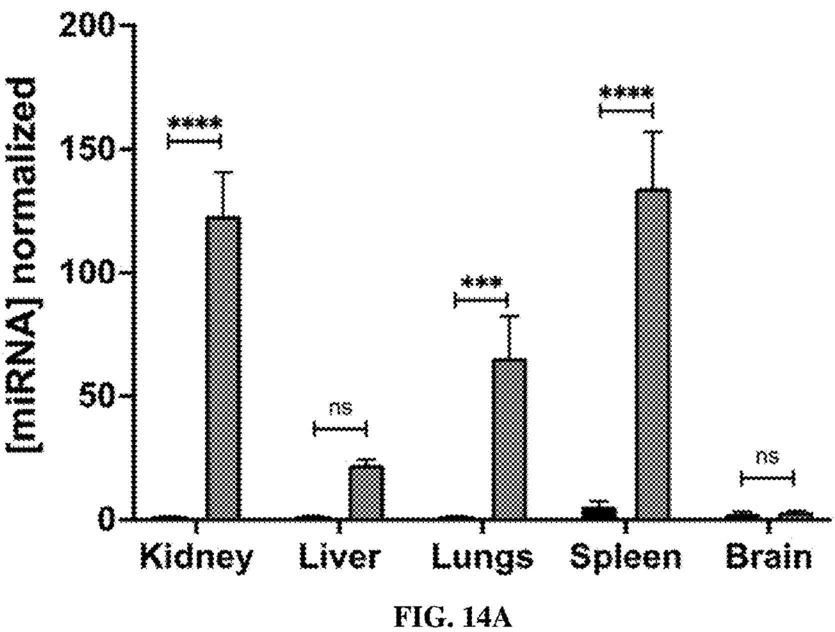
FIGS. 14A and 14B are bar graphs showing the relative mmu-miR-298 uptake by organs with treatment of mEVs and mLNPs bioengineered with NPHS2 antibody. Modified exosomes (n=3) (14A) and modified liposomes (n=6) (14B) bioengineered with a NPHS2 antibody in mice. The relative mmu-miR-298 uptake of various organs are shown on the x-axis with mice treated with serum free media (black) and mEVs/mLNPs treated (white). All the data were normalized to the constitutive level of U6 snRNA and represent the mean±SEM (**p<0.0001, *p<0.001, **p<0.01, *p<0.05). Dose: 114 ug; Injection volume: 250-300 ul.
Figure 14B:
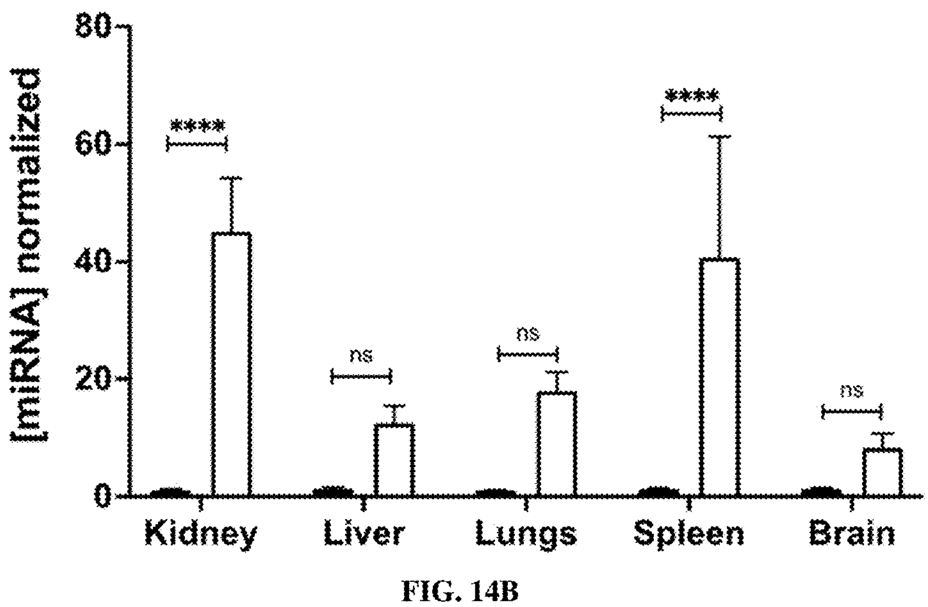

Functionalized vesicles, mLNPs and mEVs, were bioengineered with the NPHS2 polyclonal antibody abbreviated mLNP($NPHS2_{PAB}$) and mEV($NPHS2_{PAB}$), which targets the kidney-related NPHS2 integral membrane protein (FIGS. 14A-14B). Six Nu/Nu female mice aged 5-8 weeks were divided into two groups (n=3). These mice were IP administered 400 μl containing SFM only, mEVs($NPHS2_{PAB}$, mmu-miR-298) or mLNPs(NPHS2pAB, mmu-miR-298).

Functionalized vesicles mEVs and mLNPs were bioengineered with the Angiotensin converting enzyme 2 monoclonal antibody ($ACE2_{MAB}$) against membrane-associated ACE2 enzyme, which is part of the Renin-angiotensin system that controls blood pressure (FIGS. 15A-15B) [46]. This antibody was chosen to test the immunoreactivity of functionalized vesicles made by the "Functionalized Lipid Insertion Method" because ACE2 is expressed in many tissues ensuring direct interaction with them by the functionalized vesicles [47]. Eighteen female C57/BL6 mice aged 5-8 weeks were divided into three groups (n=6). These groups received 400 1 IP injections of SFM only, mEVs (ACE2MAB, mmu-miR-298), mLNPs($ACE2_{MAB}$, mmu-miR-298).

Quantification of miRNA Delivered In-Vivo

After 72 hours, the mice were euthanized using carbon dioxide [48]. After euthanasia, mouse necropsy was performed. To assess the amount of miRNA delivered, approximately 100 mg sections of each tissue were obtained. The sections were suspended in 1 ml TRIzol reagent (Invitrogen, Carlsbad, CA, USA) in a 1.5 ml microcentrifuge tube. The tissues were homogenized with the use of a 1000 μl pipette tip and a Bel-Art™ Pro Culture Cordless Homogenizer Unit (Thermo Fisher, Waltham, MA). The samples were then centrifuged at 12000 g for five minutes at 4° C. to remove tissue debris using a Microfuge™ 22R centrifuge (Beckman Coulter, Brea, CA). The RNA was extracted thereafter according to the Invitrogen protocol [49]. After RNA extraction, the RNA concentration was quantified using NanoDrop™ 2000/2000c Spectrophotometer (Thermo Fisher Scientific, Waltham, MA). The concentration was determined using the preset extinction coefficient for single-stranded RNA in the spectrophotometer (i.e., 0.025 $(\mu g/ml)^{-1}\ cm^{-1}$), and the RNA purity (>99%) was measured by the ratio of 260 nm to 280 nm (260 nm/280 nm). MiRNA delivered and the housekeeping U6 snRNA, the endogenous control, was quantified using the TaqMan™ microRNA reverse transcription, and the TaqMan™ Universal PCR MasterMix (Thermo Fisher Scientific, Waltham, MA) as explained in the earlier section.

Results

Figure 11:
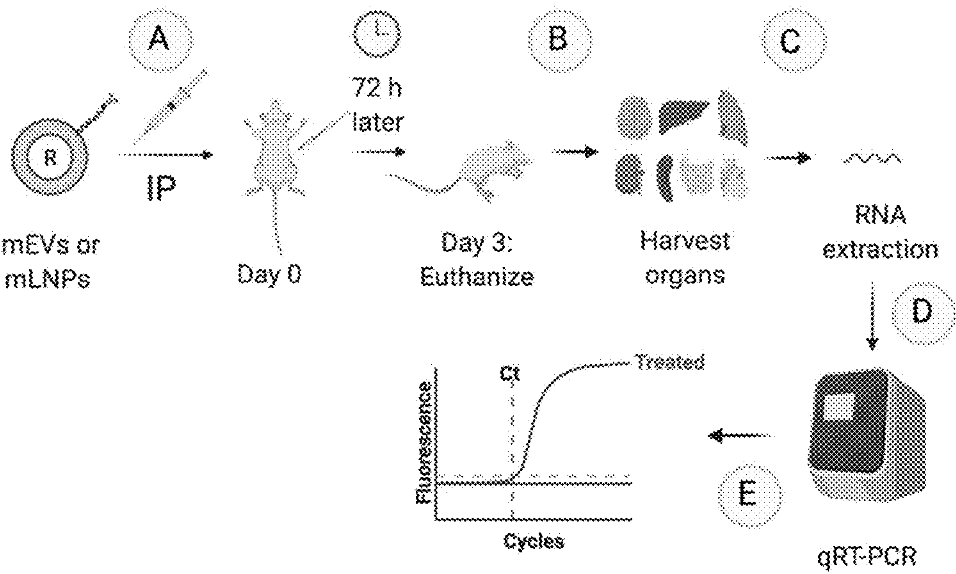
FIG. 11 is an flow chart illustrating an In vivo strategy for administering mEVs and mLNPs into mice. Step A: On Day 0, mEVs or mLNPs loaded with miRNA (R) are intraperitoneal (IP) injected into a mouse. Step B: Three days later the mouse is euthanized, and the organs are harvested. Step C: RNA is harvested from the organs using a standard TRIzol™ RNA extraction protocol. Step D: The amount of purified RNA from each of the organs is analyzed by qRT-PCR. Step E: The relative level of miRNA uptake by organs from mEV and mLNP treatment was determined using the delta-delta Ct method. Abbreviations: R, miRNA.

The uptake of miRNA in mice after treatment with mEVs and mLNPs is shown in FIG. 11. Modified vesicles, mEVs, and mLNPs are loaded with miRNA by electroporation and injected intraperitoneally (IP) into mice (FIG. 11, step A) as done previously with unmodified exosomes [74,78] and liposomes [79,80]. IP administration is easier than intravenous (IV) administration, and target organs are more readily accessible due to access to the lymphatic system [81-85]. The treated mice are euthanized after three days using carbon dioxide followed by cervical dislocation, and their organs are harvested (FIG. 11, step B). The tissue was analyzed using RNA extraction protocols that are described in the Materials and Methods (FIG. 11, step C). Using primers specific for the miRNA and qRT-PCR, the relative miRNA concentration taken up in the organs is compared to the relative concentration of the U6 housekeeping gene (FIG. 11, step D). The crossover threshold (Ct) is determined for the miRNA and the U6 housekeeping genes. Finally, the relative-fold miRNA uptake in the mouse organs is determined by the AACt method (FIG. 11, step E).

Example 9: In Vivo miRNA Delivery by Functionalized Vesicles with a Non-Interacting Antibody As a negative control for in-vivo targeting ability of mEVs and mLNPs, mice were treated with modified vesicles loaded with miRNA and the rabbit polyclonal green fluorescent protein antibody ($GFP_{PAB}$) as the non-targeting antibody. Polyclonal antibodies have higher avidity than monoclonal antibodies but can show cross-reactivity to non-target proteins [86]. At least in mice, the $GFP_{PAB}$ (Novus, NB600-308) only targets GFP and not other proteins [87,88]. FIGS. 12A-12B show the uptake of mmu-miR-298 treated with modified vesicles with the $GFP_{PAB}$ and containing mmu-miR-298 (i.e., mEV($GFP_{PAB}$, mmu-miR-298) and mLNP($GFP_{PAB}$, mmu-miR-298)). Significant miRNA uptake in all the organs of mice treated with non-targeting mEVs and mLNPs was within 30% between all the organs that were investigated. This distribution in uptake efficiencies is consistent with the mEVs and mLNPs lacking specific organ targeting ability. The highest miRNA uptake with the modified vesicles was observed in the mouse spleen, which is is directly connected to the lymphatic system and is considered a lymphoid organ [89]. The liver had about a third of the miRNA uptake than the spleen. The kidney and the lungs had only 20% of the miRNA uptake of liver and 5% of the miRNA uptake of spleen. Less than 1% of miRNA uptake was observed in the brain. The miRNA uptake in mice follows a very similar pattern for biotin-labeled liposomal uptake in the organs of rats, with the exception of liposomal uptake in the lungs [90].

Example 10: In Vivo Targeted miRNA Delivery to the Liver by Functionalized Vesicles with the ASGR1 Antibody After achieving success in delivering miRNAs by both mEVs and mLNPs bioengineered with ASGR1 antibody to hepatocellular carcinoma HepG2 cells (Example 5, FIG. 6A-6D), experiments were designed to assess the capability of these vehicles in targeting liver in vivo utilizing the same antibody. Mice were treated with mEVs($ASGR1_{PAB}$, mmu-miR-298) and mLNPs($ASGR1_{PAB}$, mmu-miR-298) like the in vitro experiments.

FIGS. 13A and 13B show the uptake of miRNA by liver, lungs, spleen, kidney and brain in mice treated with mEVs (ASGR1PAB, mmu-miR-298) and mEVs(ASGR1PAB, mmu-miR-298) normalized to the endogenous levels of mmu-miR-298 that is present in mice. MiRNA delivery from both mEVs and mLNPs was almost completely to the liver, while being relatively non-significant in other organs. The high specificity for the mEVs and mLNPs to the liver may be due to the target of $ASGR1_{PAB}$ being the ASGR1 receptor, which is naturally endocytotic.

Example 11: In Vivo Targeted miRNA Delivery to the Kidney by Modified Vesicles with the NPHS2 Antibody NPHS2 (a.k.a. Podocin), is a non-endocytotic protein associated with the kidney [91]. Modified vesicles engineered were engineered with an NPHS2 polyclonal antibody ($NPHS2_{PAB}$) to see how well these vesicles would target the kidney with mmu-miR-298. FIG. 14A shows the amount of miRNA delivered by mEVs($NPHS2_{PAB}$, mnu-niiR-298) to five major organs: kidney, liver, lungs, spleen, and brain. The amount of miRNA was normalized to the endogenous levels of miRNA (i.e., mmu-niR-298) present in untreated mice. The distribution of microRNA uptake was significantly different than mEVs and mLNPs engineered with the $GFP_{PAB}$ (FIGS. 12A, 12B) indicating that the $NPHS2_{PAB}$ on the modified vesicles affected the organ targeting. However, these modified vesicles were less specific than mEVs and mLNPs with $ASGRI_{PAB}$ (FIGS. 13A, 13B), which may be due to the fact that the NPHS2 protein is not naturally endocytoic [91] or cross-reactivity of a polyclonal antibody [92,93]. The mmu-miR-298 delivered to the kidney and spleen was the highest of all the organs and was 125-150 fold higher than untreated mice. Since the spleen is not known to express the NPHS2 protein, the high uptake of the spleen is likely due to the route of administration. The lungs and the liver showed significantly less uptake at ~25 fold and ~60 fold respectively. No significant microRNA uptake was found in the brain. Modified LNPs (i.e., nLNPs(NPHS2$_{PAB}$, mmnu-miR-298)) also showed a very similar delivery distribution (FIG. 14B) as mEVs(NPHS2$_{PAB}$, mmu-miR-298), inferring that the NPHS2$_{PAB}$ had similar targeting effects in both of these modified vesicles.

Example 12: Immunogenic Effects of miRNA Delivery by Modified Vesicles with the Relatively Non-Specific ACE2 Antibody

Materials and Methods

Cytokine Assay to Probe Immunogenicity

To explore whether the bioengineered functionalized vesicles elicit any immune response in-vivo, a cytokine assay was conducted. Around 1 ml blood was withdrawn immediately after euthanizing the animals in a BD Microtainer® tubes containing serum separator (SST™) (Becton, Dickinson and Company, Franklin lakes, NJ). The blood was allowed to clot at room temperature for 30 minutes. The tubes were then centrifuged at 1000 g for 15 minutes at 4° C. using a Microfuge™ 22R (Beckman Coulter, Brea, CA) and the serum was then stored at −80° C. Before performing the assay, the serum was centrifuge at 10,000 g for 10 minutes at 4° C. using a Microfuge™ 22R. The cytokine assay was conducted using Bio-plex Pro™ Mouse cytokine Th1/Th2 assay kit following the manufacturer's protocols (Bio-Rad, Hercules, CA) [50]. The kit is basically immunoassays coupled with magnetic beads for detecting eight inflammatory factors that are GM-CSF, IFN-g, IL-2, IL-4, IL-5, IL-10, IL-12 (p70), and TNF-α. After completing the assay, the plate was read using a Luminex Magpix system (Luminex, Austin, TX).

Results

To explore the immunogenicity of mEVs and mLNPs of in vivo targeting, a targeting vesicle was engineered with a monoclonal antibody against the membrane-associated angiotensin-converting enzyme 2 (ACE2) (ACE2MAB). This enzyme is ubiquitously expressed in many organs throughout the body and plays a key role in controlling blood pressure [47,94-97]. In rodents, ACE2 mRNA levels were found highest in the ileum in both mice and rats, followed by kidney, almost equal levels in lungs, bladder, stomach followed by a colon, adipose tissue, atrium, brainstem, forebrain, and ventricle whereas lowest levels were found in the spleen for both[98]. A different but pervasive pattern in protein levels was observed with highest in the atrium (124.5%) and ventricle (131.7%), moderate expression in kidney (100%), lesser in the lung (19.7%), testis (28.7%), thymus (44.4%), and least amount in the spleen [98]. Therefore, targeting of mEVs and mLNPs with ACE2MAB will be relatively non-specific, but more evenly distributed among the organs than mEVs and mLNPs with GFP$_{PAB}$, which primarily targeted the spleen (FIGS. 12A, 12B).

Figure 15A:
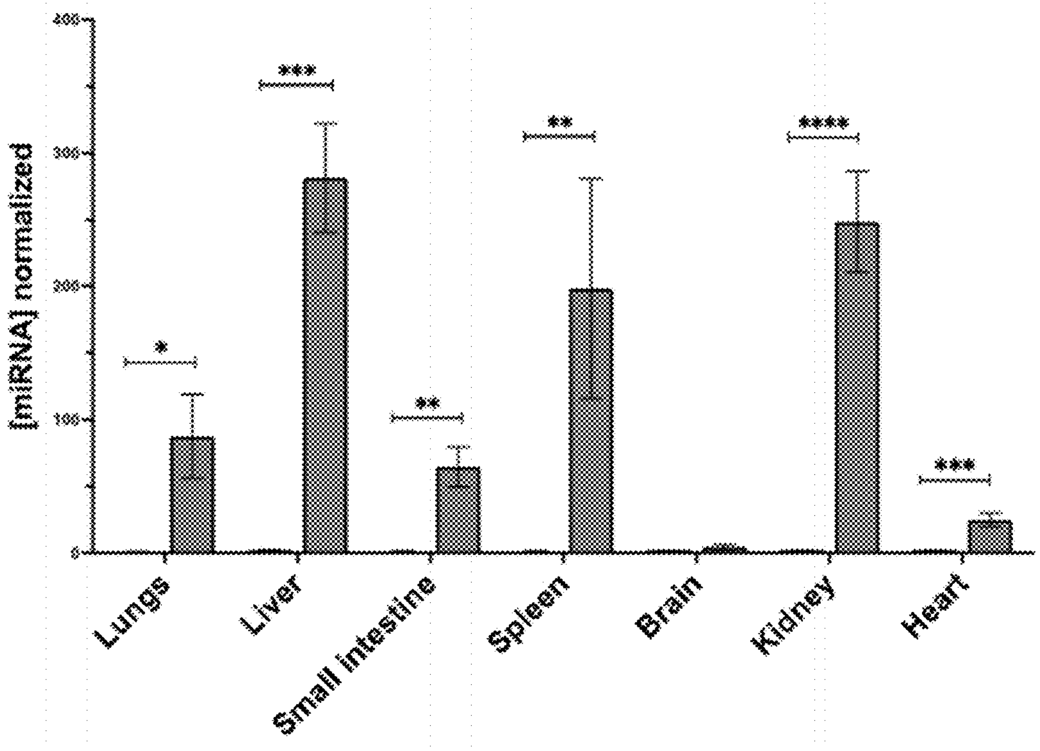
FIGS. 15A-15C illustrate ACE2 targeting and immune reactivity of mEV(ACE2) and mLNP(ACE2) in-vivo.
Figure 15B:
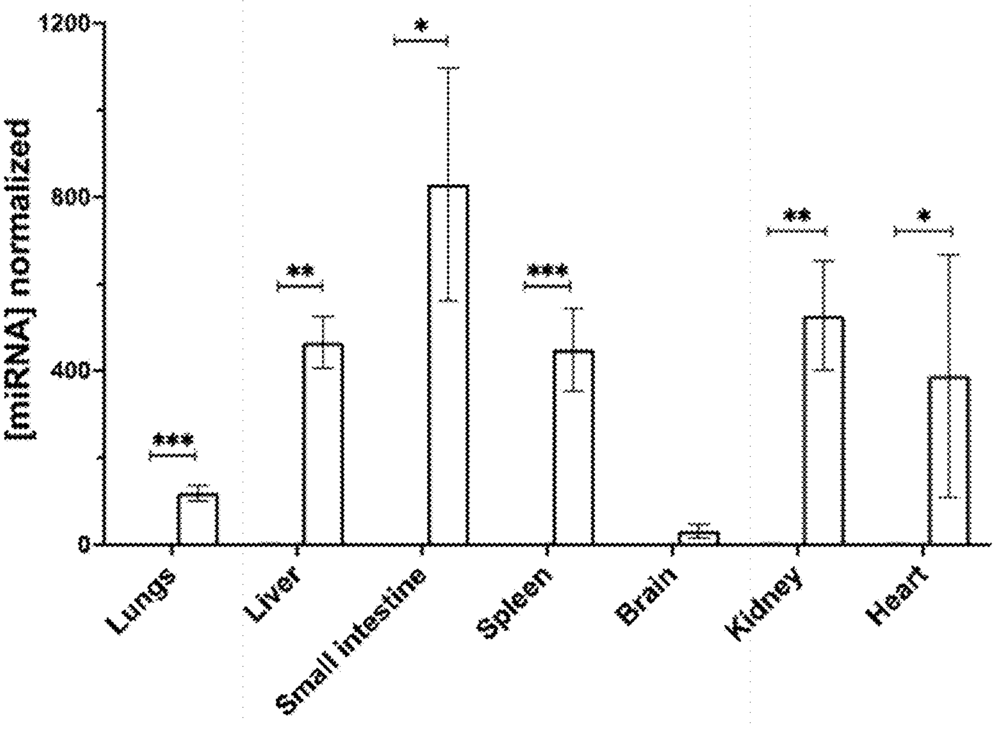
Figure 15C:
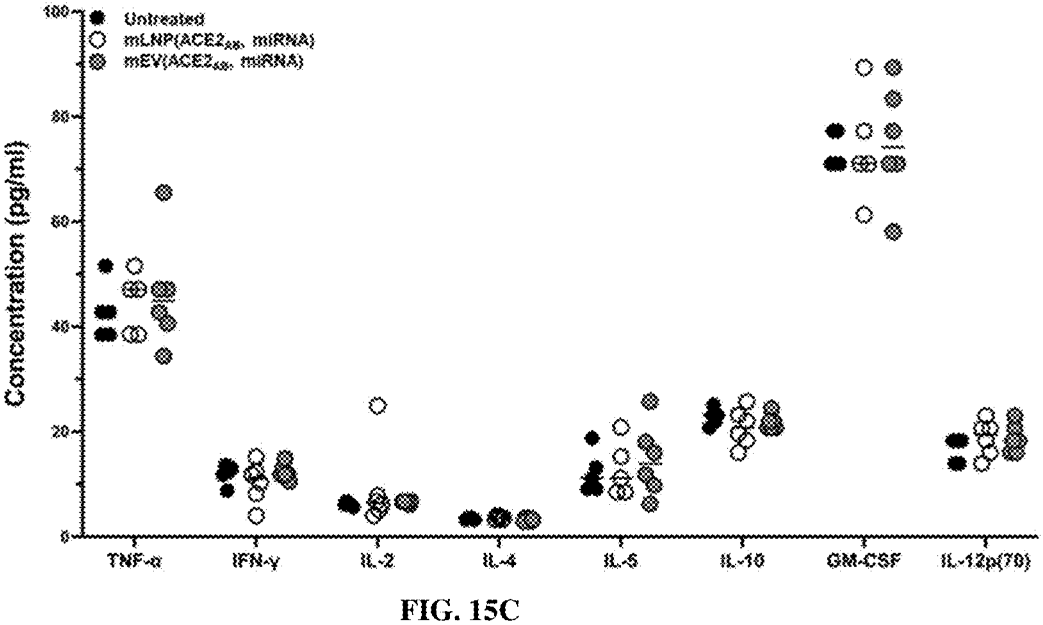

FIGS. 15A-15C shows the uptake of mmu-miR-298 and their effects on the cytokine levels after treatment of mice with miRNA-loaded mEVs and mLNPs engineered with ACE2$_{MAB}$. In FIG. 15A, the relative miRNA uptake was analyzed in various organs to determine possible immunogenic effects, including the lungs, liver, small intestine, spleen, brain, kidney, and heart. Increased levels of miR-298 were observed in all the analyzed organized versus the untreated controls. Highest levels were delivered in the small intestine (~830 fold) followed by the kidney (~530 fold), spleen (~400 fold), liver (~400 fold), heart (~388 fold), lungs (~100 fold), and brain of mice treated by mLNPs(ACE2$_{MAB}$, mmu-miR-298). Except for the spleen, these relative miRNA uptake levels are consistent with the protein expression levels of the ACE2 protein in rodents and humans [47,97,98]. The distribution of miRNA delivery to organs by mEVs(ACE2$_{MAB}$, mmu-miR-298) differed significantly from mLNPs. From high to low fold miRNA uptake by mEV treated mice versus untreated mice, the miRNA uptake in mice by mEVs was ~280 fold in the liver, ~250 fold in the kidneys, ~200 fold in the spleen, ~200 fold in the lungs, ~90 fold in the small intestine, ~70 fold in the heart and ~25 fold in the brain (FIG. 15B). Since there is almost no ACE2 enzyme in the spleen [98], the relatively high miRNA uptake after treatment with mEVs and mLNPs is likely due to the route of administration rather than specific targeting by ACE2$_{MAB}$ of the modified vesicles.

To assess the acute immunogenicity of the vehicles, an 8-panel Th1/Th2 Bio-plex was used to conduct cytokine profiling on the serum samples derived from the mice treated with the modified vehicles, a common technique to analyze immunogenicity of both exosomes and liposome [99-101]. FIG. 15C shows the levels of 8 major anti- and pro-inflammatory cytokines, GM-CSF, IFN-Y, IL-1p, IL-2, IL-4, IL-5, IL-10, and TNF-α in mice when treated with mEVs (ACE2$_{MAB}$, mmu-miR-298) and mLNPs(ACE2$_{MAB}$, mmu-miR-298) in comparison to the natural levels in endogenous mice. No significant change in the levels of any of the cytokines was observed in mice when treated with the modified vesicles. With all the in vivo experiments described herein (e.g., FIGS. 12A-15C), no physical manifestations of an immune response were observed by treatment with mEVs and mLNPs such as redness, itching, or sudden loss of hair.

The provided experiments utilized a "Functionalized Lipid Insertion Method" to bioengineer targeting functionalized vesicles with a surface coated with PEG-linked Abs that are referred to as mEVs or mLNPs. The approach is different from the "Detergent-Dialysis Method" discussed elsewhere [16-23].

These functionalized vesicles are versatile and can target surface receptors. Both mEVs and mLNPs could efficiently deliver miRNA to the HEPG2 cell line. The in-vitro miRNA uptake efficiency was 8-fold and 15-fold higher than the transfection reagent by mEVs and mLNPs respectively. mEVs treatment of cells with growth-affecting miRNA caused significant effects on mRNA expression and cellular growth. Targeted delivery of miRNA to liver (more than 80%) and kidney (more than 50%) was achieved by both mEVs and mLNPs in-vivo. The modified vesicles also were essentially non-immunogenic (FIGS. 15A-15C).

Unmodified exosomes can have oligonucleotide uptake efficiencies and target cells like mEVs [102,103]. Exosomes derived from the human hepatoma Huh7 cell line appear to target the human embryonic kidney cell line over human PBMCs or a human lymphoblast cell line [102]. The miRNA uptake efficiencies for the human embryonic kidney cell line treated with exosomes were 5-200-fold higher than the other cell lines [102]. A study with exosomes derived from MDA- MB-231 cells and H-29 colon cancer cells indicated that efficient exosomal targeting relied on complementary interactions [103]. Unmodified exosomes are the simplest to produce but predicting the exosomal target typically requires analyzing the oligonucleotide uptake in a range of tissues and cell lines to determine specificity.

To control targeting to cells and improve uptake of oligonucleotides, methods have been developed to modify the surfaces of natural vesicles [14]. Targeting and miRNA uptake of CD8+ T-cell derived exosomes to effector T-cells was improved by having a constitutive exosomal protein bound with antibodies [14]. Unfortunately, this simple approach does not have broader applicability to exosomal targeting beyond T-cells. Another strategy to exploit constitutive exosomal proteins is to fuse them with a targeting proteins by genetic engineering [104]. Exosomes were genetically-engineered with a lysosomal protein (Lamp2b) and the rabies viral glycoprotein (RVG) [72]. They were able to enhance siRNA uptake efficiency in cells as well as overcome the blood-brain barrier (BBB) in mice [41]. Exosomes have been genetically-engineered with fusion proteins of the lysosomal protein (Lamp2) with the green fluorescent protein (GFP) for fluorescent tracking and with the HER2 affibody for targeting [105]. Exosomes have also been genetically-engineered with a construct made from the vesicular stomatitis virus glycoprotein with improved loading, delivery and tracking [106]. Development of modified exosomes by genetic engineering is limited by the complexity of engineering the fusion protein construct as well as getting the construct to express in budding exosomes [104].

Highly PEGylated exosomes with a relatively low surface density of Abs than Abi-exosomes was developed using a two-stage process to deliver anticancer drugs cells [15]. The modified exosomes provided only a ~30% increase in anticancer drug uptake by a human pancreatic cancer cell line [15].

Similarly, modified and unmodified LNPs have been used to deliver miRNA. Cationic liposomes have been used as transfection agents deliver miRNA such as miR-7 to ovarian cancer cells, miR-143 and −145 in human colorectal tumors, and miR-122 in liver cells achieving up to 80% efficiency [71,107,108]. Cationic liposomes typically consist of a cationic lipid, a neutral lipid and/or cholesterol and a PEG-lipid. Cationic liposomes are known to form ion pairs with anionic phospholipids of the endosomal membrane leading to the release of cargo efficiently. This makes them one of the promising drug delivery vehicles. Cationic liposomes can form complexes with oligonucleotides such as miRNA and are known as lipoplexes. For instance, a cationic based lipoplex delivery system has been used to deliver miR-29b, and miR-133b to non-small cell lung cancer cells. The lipoplexes achieved over 2-fold delivery efficiency in comparison to the transfection reagent in vitro. In addition to low delivery efficiency, when injected intravenously, only 30% accumulation was achieved in the target organ, lungs, with highest amount found in liver, followed by kidney and spleen [109,110].

However, the traditional process of preparing lipoplexes unfortunately renders them unoptimizable down the process and increases the risk of interaction of cationic lipids with other tissues making them non-specific limiting their potential as targeted drug delivery vehicles.

In addition to cationic liposomes, liposomes can also be conjugated with target specific vectors to design cell specific vehicles. Targeted liposomes have been prepared by conjugating Aptamer (AS1411), a target specific single stranded oligonucleotide, using thioether linkage between DSPE-PEG2000 maleimide on liposomal surface. These Aptamer functionalized liposomes were used to deliver miR-29b to A2780 cells, ovarian cancer cells[111]. Another study prepared a liposome-polycation-hyaluronic acid (LPH) modified with GC4 single chain variable fragment, a tumor targeting monoclonal antibody to deliver siRNA and miRNA to B16F10, metastatic lung cancer cells. The GC4 targeted liposomes achieved 40% delivery of siRNA in the tumor and highest accumulation was achieved in liver (>50%) when dosed intravenously to the tumor bearing mice [112]. An antibody against CD59 receptor, a receptor overexpressed in the cervical cancers, was conjugated to Cisplatin (CDDP)/miR1284-loaded liposomes. CD59 conjugated vehicles showed significant increase in miRNA induced cytotoxicity in cervical cancer cells and prolonged blood circulation of cisplatin [75].

All these studies have used post-conjugation method to modify liposomes, where they attach derivatized PEGylated lipids to the liposomes while preparing liposomes followed by conjugation of antibody. This method is more complicated, as lipid derivatives are functionalized even before preparing liposomes. However, post-insertion methods: attachment of antibodies to derivatized lipids first, and then inserting antibody derivatized lipids in PEGylated liposomes, gives more versatility in designing or modifying liposomes as-desired. Post-insertion method is a simpler, more flexible method and has been shown to be as effective as if not more than the post conjugation method [113]. Post-insertion method has been used to attach target specific antibodies such as CD44 and CD133 to deliver cargoes like small molecules like doxorubicin or antibodies like anti-IL6R antibody[114,115]. It is believed that this method has not been used to deliver miRNAs. Also, using the disclosed methods, miRNAs can be loaded using electroporation in comparison to the loading techniques used in the above mentioned studies such as sonication, incubation, or lipid hydration.

Considering the versatility of mEVs and mLNPs, they are simple and efficient modified therapeutic delivery vehicles. Fluorescence tracking, PEGylation and Ab targeting are integrated into a single dialysis step followed by electroporation for oligonucleotide loading. Industrial methods for dialyzing and electroporation are available [116,117]. Synthetic methods are available to produce large amounts of miRNA [118]. Innovative large-scale production of monoclonal Abs are being developed from plants [119]. Currently, getting EVs can be rate-limiting for industrial manufacturing, but methods are being developed for obtaining them from abundant sources such as milk [120,121], and methods are available to upscale liposome preparation, including microfluidics [122,123].

For long-term viability, EVs and by extension mEVs are most often stored at −80° C., but month-long room temperature storage has been shown after lyophilization and in the presence of trehalose [30,124]. In contrast, lyophilized LNPs can last up to a year at 4° C. or room temperature in an oxygen-free environment [125-128]. MicroRNAs are typically stored at −80° C. [129], but methods are available to increase temperature stability through chemical modification [73]. MiRNA also has the potential for slowly leaking from functionalized vesicles [130].

In sum, herein, is provided a scalable and straightforward approach to produce functionalized vesicles, referred to as the "Functionalized Lipid Insertion Method." This method differs significantly from an older approach referred to as the "Detergent-Dialysis Method." In the "Detergent-Dialysis Method," all the components in the functionalized vesicle are solubilized with excess detergent that requires extensive dialysis and often column chromatography for removal. The vesicle formation process in this method randomizes all of the components' orientations, including the functionalized lipid. With the "Functionalized Lipid Insertion Method," only the functionalized lipid is detergent-solubilized during dialysis. This approach greatly reduces the dialysis time by reducing the detergent concentration, keeps the original vesicle intact and preferentially orients the functionalized lipid within the lipid bilayer of the functionalized vesicle. The dynamic light scattering (DLS) technique showed that the size of functionalized vesicles using the "Detergent-Dialysis Method" were highly dependent on the starting conditions compared with the "Functionalized Lipid Insertion Method." In vitro, functionalized vesicles using the "Functionalized Lipid Insertion Method" are able to selectively deliver miRNA and functionally affect hepatocellular carcinoma (HCC) HepG2 cells. Functionalized vesicles by this method can also target delivery of miRNA in mice without significant immunogenicity.

BIBLIOGRAPHY

[1] J.K. Patra, G. Das, L.F. Fraceto, E.V.R. Campos, M. del P. Rodriguez-Torres, L. S. Acosta-Torres, L. A. Diaz-Torres, R. Grillo, M. K. Swamy, S. Sharma, S. Habtemariam, H.-S. Shin, Nano based drug delivery systems: recent developments and future prospects, Journal of Nanobiotechnology. 16 (2018) 71.

[2] D. Das, N. Maity, A. H. V, Nanotechnology: a revolution in targeted drug delivery, International Journal of Basic & Clinical Pharmacology. 6 (2017) 2766-2773.

[3] B. S. Zolnik, A. Gonzalez-Fernandez, N. Sadrieh, M. A. Dobrovolskaia, Nanoparticles and the Immune System, Endocrinology. 151 (2010) 458-465.

[4] S. Su, P. M. Kang, Systemic Review of Biodegradable Nanomaterials in Nanomedicine, Nanomaterials (Basel). 10 (2020).

[5] X. Li, L. Wang, Y. Fan, Q. Feng, F. Cui, Biocompatibility and Toxicity of Nanoparticles and Nanotubes, Journal of Nanomaterials. 2012 (2012) e548389.

[6] F. Alexis, E. Pridgen, L. K. Molnar, O. C. Farokhzad, Factors Affecting the Clearance and Biodistribution of Polymeric Nanoparticles, Mol Pharm. 5 (2008) 505-515.

[7] S. T. Jahan, S.M.A. Sadat, M. Walliser, A. Haddadi, Targeted Therapeutic Nanoparticles: An Immense Promise to Fight against Cancer, Journal of Drug Delivery. 2017 (2017) e9090325.

[8] X. Luan, K. Sansanaphongpricha, I. Myers, H. Chen, H. Yuan, D. Sun, Engineering exosomes as refined biological nanoplatforms for drug delivery, Acta Pharmacologica Sinica. 38 (2017) 754-763.

[9] A. Akbarzadeh, R. Rezaei-Sadabady, S. Davaran, S. W. Joo, N. Zarghami, Y. Hanifehpour, M. Samiei, M. Kouhi, K. Nejati-Koshki, Liposome: classification, preparation, and applications, Nanoscale Res Lett. 8 (2013) 102.

[10] R. Kalluri, V. S. LeBleu, The biology, function, and biomedical applications of exosomes, Science. 367 (2020).

[11] J. Qin, Q. Xu, Functions and application of exosomes, Acta Pol Pharm. 71 (2014) 537-43.

[12] R. R. Sawant, V. P. Torchilin, Challenges in Development of Targeted Liposomal Therapeutics, AAPS J. 14 (2012) 303-315.

[13] A. Samad, Y. Sultana, M. Agil, Liposomal drug delivery systems: an update review, Curr Drug Deliv. 4 (2007) 297-305.

[14] K. Bryniarski, W. Ptak, A. Jayakumar, K. Pullmann, M. J. Caplan, A. Chairoungdua, J. Lu, B. D. Adams, E. Sikora, K. Nazimek, S. Marquez, S. H. Kleinstein, P. Sangwung, Y. Iwakiri, E. Delgato, F. Redegeld, B. R. Blokhuis, J. Wojcikowski, A. W. Daniel, T. G. Kormelink, P. W. Askenase, Antigen-specific, antibody-coated, exosome-like nanovesicles deliver suppressor T-cell microRNA-150 to effector T cells to inhibit contact sensitivity, Journal of Allergy and Clinical Immunology. 132 (2013) 170-181.e9.

[15] Y. Si, S. Kim, E. Zhang, Y. Tang, R. Jaskula-Sztul, J. M. Markert, H. Chen, L. Zhou, X. (Margaret) Liu, Targeted Exosomes for Drug Delivery: Biomanufacturing, Surface Tagging, and Validation, Biotechnology Journal. 15 (2020) 1900163.

[16] A. Huang, L. Huang, S. J. Kennel, Monoclonal antibody covalently coupled with fatty acid. A reagent for in vitro liposome targeting., Journal of Biological Chemistry. 255 (1980) 8015-8018.

[17] J. L. Rigaud, D. Levy, Reconstitution of membrane proteins into liposomes, Methods in Enzymology. 372 (2003) 65-86.

[18] L. E. Westerman, P. E. Jensen, Liposomes Composed of Reconstituted Membranes for Induction of Tumor-Specific Immunity, in: Methods in Enzymology, Academic Press, 2003: pp. 118-127.

[19] A. Huang, S. J. Kennel, L. Huang, Immunoliposome labeling: A sensitive and specific method for cell surface labeling, Journal of Immunological Methods. 46 (1981) 141-151.

[20] H. Alpes, K. Allmann, H. Plattner, J. Reichert, R. Rick, S. Schulz, Formation of large unilamellar vesicles using alkyl maltoside detergents, Biochimica et Biophysica Acta (BBA)—Biomembranes. 862 (1986) 294-302.

[21] L. Huang, U.S. Pat. No. 4,957,735 —Target-sensitive immunoliposomes-preparation and characterization, 4957735, 1990. (accessed Aug. 31, 2021).

[22] R.J.Y. Ho, B. T. Rouse, L. Huang, Target-sensitive immunoliposomes: preparation and characterization, Biochemistry. 25 (1986) 5500-5506.

[23] M. Micklus, N. Greig, S. Rapoport, Targeting of liposomes to the blood-brain barrier, US20020025313A1, 2002. (accessed Aug. 21, 2021).

[24] Y. Cheng, Q. Zeng, Q. Han, W. Xia, Effect of pH, temperature and freezing-thawing on quantity changes and cellular uptake of exosomes, Protein Cell. 10 (2019) 295-299.

[25] H. Ma, C. 6'Figain, R. O'Kennedy, Antibody stability: A key to performance—Analysis, influences and improvement, Biochimie. 177 (2020) 213-225.

[26] R. Rupaimoole, F. J. Slack, MicroRNA therapeutics: towards a new era for the management of cancer and other diseases, Nat Rev Drug Discov. 16(2017)203-222.

[27] J. O'Brien, H. Hayder, Y. Zayed, C. Peng, Overview of MicroRNA Biogenesis, Mechanisms of Actions, and Circulation, Front. Endocrinol. 9 (2018).

[28] C. E. Condrat, D. C. Thompson, M. G. Barbu, O. L. Bugnar, A. Boboc, D. Cretoiu, N. Suciu, S. M. Cretoiu, S. C. Voinea, miRNAs as Biomarkers in Disease: Latest Findings Regarding Their Role in Diagnosis and Prognosis, Cells. 9 (2020).

[29] W. Si, J. Shen, H. Zheng, W. Fan, The role and mechanisms of action of microRNAs in cancer drug resistance, Clinical Epigenetics. 11 (2019) 25.

[30] A. Jeyaram, S. M. Jay, Preservation and Storage Stability of Extracellular Vesicles for Therapeutic Applications, AAPS J. 20 (2017) 1.

[31] S. K. Panda, B. Ravindran, F. Histopaque, Isolation of human PBMCs, Bio-Protocol. 3 (2013) e323.

[32] G. E. Moore, R. E. Gerner, H. A. Franklin, Culture of Normal Human Leukocytes, JAMA. 199 (1967) 519-524.

[33] B. Mui, L. Chow, M. J. Hope, Extrusion technique to generate liposomes of defined size, Methods in Enzymology. 367 (2003) 3-14.

[34] K. V. Ledwitch, R. W. Barnes, A. G. Roberts, Unravelling the complex drug-drug interactions of the cardiovascular drugs, verapamil and digoxin, with P-glycoprotein, Biosci. Rep. 36 (2016) 1-14.

[35] S. Hupfeld, A. M. Holsxter, M. Skar, C. B. Frantzen, M. Brandl, Liposome Size Analysis by Dynamic/Static Light Scattering upon Size Exclusion-/Field Flow-Fractionation, Journal of Nanoscience and Nanotechnology. 6 (2006) 3025-3031.

[36] G. Liang, S. Kan, Y. Zhu, S. Feng, W. Feng, S. Gao, Engineered exosome-mediated delivery of functionally active miR-26a and its enhanced suppression effect in HepG2 cells, Int J Nanomedicine. 13 (2018) 585-599.

[37] O. L6pez, A. de la Maza, L. Coderch, C. L6pez-Iglesias, E. Wehrli, J. L. Parra, Direct formation of mixed micelles in the solubilization of phospholipid liposomes by TRITON™ X-100 (2-[4-(2,4,4-trimethylpentan-2-yl)phenoxy]ethanol), FEBS Letters. 426 (1998) 314-318.

[38] V. Palmieri, D. Lucchetti, I. Gatto, A. Maiorana, M. Marcantoni, G. Maulucci, M. Papi, R. Pola, M. De Spirito, A. Sgambato, Dynamic light scattering for the characterization and counting of extracellular vesicles: a powerful noninvasive tool, J Nanopart Res. 16 (2014) 2583.

[39] R. Szatanek, M. Baj-Krzyworzeka, J. Zimoch, M. Lekka, M. Siedlar, J. Baran, The Methods of Choice for Extracellular Vesicles (EVs) Characterization, Int J Mol Sci. 18 (2017).

[40] I. Makra, P. Terejanszky, R. E. Gyurcsinyi, A method based on light scattering to estimate the concentration of virus particles without the need for virus particle standards, MethodsX. 2 (2015) 91-99.

[41] L. Alvarez-Erviti, Y. Seow, H. Yin, C. Betts, S. Lakhal, M.J.A. Wood, Delivery of siRNA to the mouse brain by systemic injection of targeted exosomes, Nature Biotechnology. 29 (2011) 341-345.

[42] M. W. Pfaffl, Relative quantitation, in: M. T. Dorak (Ed.), Real-Time PCR, 1st edition, Taylor & Francis, 2007.

[43] A. L. Didychuk, S. E. Butcher, D. A. Brow, The life of U6 small nuclear RNA, from cradle to grave, RNA. 24 (2018) 437-460.

[44] R. L. Causin, D. Pessôa-Pereira, K.C.B. Souza, A. F. Evangelista, R.M.V. Reis, J.H.T.G. Fregnani, M.M.C. Marques, Identification and performance evaluation of housekeeping genes for microRNA expression normalization by reverse transcription-quantitative PCR using liquid-based cervical cytology samples, Oncol Lett. 18 (2019) 4753-4761.

[45] T. D. Schmittgen, K. J. Livak, Analyzing real-time PCR data by the comparative C T method, Nature Protocols. 3 (2008) 1101-1108.

[46] I. Hamming, M. Cooper, B. Haagmans, N. Hooper, R. Korstanje, A. Osterhaus, W. Timens, A. Turner, G. Navis, H. van Goor, The emerging role of ACE2 in physiology and disease, J Pathol. 212 (2007) 1-11.

[47] I. Hamming, W. Timens, M. Bulthuis, A. Lely, G. Navis, H. van Goor, Tissue distribution of ACE2 protein, the functional receptor for SARS coronavirus. A first step in understanding SARS pathogenesis, J Pathol. 203 (2004) 631-637.

[48] C. Km, S. Ml, R. An, K. La, Carbon Dioxide for Euthanasia: Concerns Regarding Pain and Distress, With Special Reference to Mice and Rats, Laboratory Animals. 39 (2005).

[49] TRIzol Products-US, (n.d.). (accessed May 16, 2020).

[50] Bio-Plex Pro™ Mouse Cytokine, Chemokine, and Growth Factor Assays I Life Science Research I Bio-Rad, (n.d.). (accessed Dec. 11, 2020).

[51] L. A. Mulcahy, R. C. Pink, D.R.F. Carter, Routes and mechanisms of extracellular vesicle uptake, J Extracell Vesicles. 3 (2014).

[52] G. Costaguta, G. S. Payne, Overview of Protein Trafficking Mechanisms, in: N. Segev (Ed.), Trafficking Inside Cells: Pathways, Mechanisms and Regulation, Springer, New York, NY, 2009: pp. 105-118.

[53] A. Perrakis, W. H. Moolenaar, Autotaxin: structure-function and signaling, J. Lipid Res. 55 (2014) 1010-1018.

[54] J. Stetefeld, S. A. McKenna, T. R. Patel, Dynamic light scattering: a practical guide and applications in biomedical sciences, Biophys Rev. 8 (2016) 409-427.

[55] P. M. Carvalho, M. R. Felicio, N.C. Santos, S. Gongalves, M. M. Domingues, Application of Light Scattering Techniques to Nanoparticle Characterization and Development, Frontiers in Chemistry. 6 (2018) 237.

[56] K. L. Linegar, A. E. Adeniran, A. F. Kostko, M. A. Anisimov, Hydrodynamic radius of polyethylene glycol in solution obtained by dynamic light scattering, Colloid J. 72 (2010) 279-281.

[57] S. Niimi, [Determination of the particle size and relative light scattering intensity of aggregates of human IgG and humanized monoclonal antibody product induced by various stress using dynamic light scattering], Kokuritsu Iyakuhin Shokuhin Eisei Kenkyusho Hokoku. (2011) 55-60.

[58] M. T. Donato, L. Tolosa, M. J. G6mez-Lech6n, Culture and Functional 20 Characterization of Human Hepatoma HepG2 Cells, Methods Mol. Biol. 1250 (2015) 77-93.

[59] S. Wilkening, F. Stahl, A. Bader, Comparison of Primary Human Hepatocytes and Hepatoma Cell Line Hepg2 with Regard to Their Biotransformation Properties, Drug Metab Dispos. 31 (2003) 1035-1042.

[60] G.-H. Qiu, X. Xie, F. Xu, X. Shi, Y. Wang, L. Deng, Distinctive pharmacological differences between liver cancer cell lines HepG2 and Hep3B, Cytotechnology. 67 (2015) 1-12.

[61] D. Witzigmann, L. Quagliata, S. H. Schenk, C. Quintavalle, L. M. Terracciano, J. Huwyler, Variable asialoglycoprotein receptor 1 expression in liver disease: Implications for therapeutic intervention, Hepatology Research. 46 (2016) 686-696.

[62] S. Das, P. Kudale, P. Dandekar, P. V. Devarajan, Asialoglycoprotein Receptor and Targeting Strategies, in: P. V. Devarajan, P. Dandekar, A. A. D'Souza (Eds.), Targeted Intracellular Drug Delivery by Receptor Mediated Endocytosis, Springer International Publishing, Cham, 2019: pp. 353-381.

[63] Z. Shen, W. Wei, H. Tanaka, K. Kohama, G. Ma, T. Dobashi, Y. Maki, H. Wang, J. Bi, S. Dai, A galactosamine-mediated drug delivery carrier for targeted liver cancer therapy, Pharmacological Research. 64 (2011) 410-419.

[64] S. Pranatharthiharan, M. D. Patel, V. C. Malshe, V. Pujari, A. Gorakshakar, M. Madkaikar, K. Ghosh, P. V.

Devarajan, Asialoglycoprotein receptor targeted delivery of doxorubicin nanoparticles for hepatocellular carcinoma, Drug Delivery. 24 (2017) 20-29.

[65] M. Wei, Y. Xu, Q. Zou, L. Tu, C. Tang, T. Xu, L. Deng, C. Wu, Hepatocellular carcinoma targeting effect of PEGylated liposomes modified with lactoferrin, European Journal of Pharmaceutical Sciences. 46 (2012) 131-141.

[66] A. A. D'Souza, P. V. Devarajan, Asialoglycoprotein receptor mediated hepatocyte targeting—Strategies and applications, Journal of Controlled Release. 203 (2015) 126-139.

[67] D. Barbagallo, S. Piro, A. G. Condorelli, L. G. Mascali, F. Urbano, N. Parrinello, A. Monello, L. Statello, M. Ragusa, A. M. Rabuazzo, C. Di Pietro, F. Purrello, M. Purrello, miR-296-3p, miR-298-5p and their downstream networks are causally involved in the higher resistance of mammalian pancreatic a cells to cytokine-induced apoptosis as compared to $ cells, BMC Genomics. 14 (2013) 62.

[68] P. Huang, T. Liu, X. Luo, X. Sun, Microarray analysis of microRNA expression patterns involved in Ap-induced retinal degeneration, Invest. Ophthalmol. Vis. Sci. 57 (2016). (accessed Feb. 19, 2021).

[69] P. E. Marques, S. Nyegaard, R. F. Collins, F. Troise, S. A. Freeman, W. S. Trimble, S. Grinstein, Multimerization and Retention of the Scavenger Receptor SR-B1 in the Plasma Membrane, Developmental Cell. 50 (2019) 283-295.e5.

[70] D. Sahoo, Y. F. Darlington, D. Pop, D. L. Williams, M. A. Connelly, Scavenger receptor class B Type I (SR-BI) assembles into detergent-sensitive dimers and tetramers, Biochimica et Biophysica Acta (BBA) —Molecular and Cell Biology of Lipids. 1771 (2007) 807-817.

[71] X. Cui, K. Song, X. Lu, W. Feng, W. Di, Liposomal Delivery of MicroRNA-7 Targeting EGFR to Inhibit the Growth, Invasion, and Migration of Ovarian Cancer, ACS Omega. (2021).

[72] M.T.D. Martino, V. Campani, G. Misso, M.E.G. Cantafio, A. Gulla, U. Foresta, P. H. Guzzi, M. Castellano, A. Grimaldi, V. Gigantino, R. Franco, S. Lusa, M. Cannataro, P. Tagliaferri, G. D. Rosa, P. Tassone, M. Caraglia, In Vivo Activity of MiR-34a Mimics Delivered by Stable Nucleic Acid Lipid Particles (SNALPs) against Multiple Myeloma, PLOS ONE. 9 (2014) e90005.

[73] E. W. R., W. H., N. Y., C. J., Improving the Stability of Aptamers by Chemical Modification, Current Medicinal Chemistry. 18 (2011) 4126-4138.

[74] M. Alexander, R. Hu, M. C. Runtsch, D. A. Kagele, T. L. Mosbruger, T. Tolmachova, M. C. Seabra, J. L. Round, D. M. Ward, R. M. O'Connell, Exosome-delivered microRNAs modulate the inflammatory response to endotoxin, Nature Communications. 6 (2015) 1-16.

[75] L. Wang, T.-T. Liang, CD59 receptor targeted delivery of miRNA-1284 and cisplatin-loaded liposomes for effective therapeutic efficacy against cervical cancer cells, AMB Express. 10 (2020) 1-11.

[76] A. Stamm, K. Reimers, S. Strau3, P. Vogt, T. Scheper, I. Pepelanova, In vitro wound healing assays—state of the art, BioNanoMaterials. 17 (2016) 79-87.

[77] J.E.N. Jonkman, J. A. Cathcart, F. Xu, M. E. Bartolini, J. E. Amon, K. M. Stevens, P. Colarusso, An introduction to the wound healing assay using live-cell microscopy, Cell Adhesion & Migration. 8 (2014) 440-451.

[78] D. Sun, X. Zhuang, W. Grizzle, D. Miller, H.-G. Zhang, A novel nanoparticle drug delivery system: The anti-inflammatory activity of curcumin is enhanced when encapsulated in exosomes, AACR, 2011.

[79] A. E. Bulboaca, P. M. Boarescu, S. D. Bolboaca, M. Blidaru, D. Festila, G. Dogaru, C. A. Nicula, Comparative Effect Of Curcumin Versus Liposomal Curcumin On Systemic Pro-Inflammatory Cytokines Profile, MCP-1 And RANTES In Experimental Diabetes Mellitus, Int J Nanomedicine. 14 (2019) 8961-8972.

[80] R. S. Araúdjo, A.L.M. Silveira, E. L. de Sales e Souza, R. H. Freire, C. M. de Souza, D. C. Reis, B.R.C. Costa, M. A. Sugimoto, J. N. Silveira, F. dos Santos Martins, G. D. Cassali, J.I.A. Leite, L. P. Sousa, A.V.M. Ferreira, M. C. Oliveira, V. N. Cardoso, Intestinal toxicity evaluation of long-circulating and pH-sensitive liposomes loaded with cisplatin, European Journal of Pharmaceutical Sciences. 106 (2017) 142-151.

[81] M. J. Haney, Y. Zhao, J. Fay, H. Duhyeong, M. Wang, H. Wang, Z. Li, Y. Z. Lee, M. K. Karuppan, N. El-Hage, A. V. Kabanov, E. V. Batrakova, Genetically modified macrophages accomplish targeted gene delivery to the inflamed brain in transgenic Parkin Q311X(A) mice: importance of administration routes, Scientific Reports. 10 (2020) 11818.

[82] O.P.B. Wiklander, J. Z. Nordin, A. O'Loughlin, Y. Gustafsson, G. 15 Corso, I. Mager, P. Vader, Y. Lee, H. Sork, Y. Seow, N. Heldring, L. Alvarez-Erviti, C. E. Smith, K. Le Blanc, P. Macchiarini, P. Jungebluth, M.J.A. Wood, S. E. Andaloussi, Extracellular vesicle in vivo biodistribution is determined by cell source, route of administration and targeting, J Extracell Vesicles. 4 (2015) 10.3402/jev.v4.26316.

[83] P. Rosa, F. Clementi, Absorption and Tissue Distribution of Doxorubicin Entrapped in Liposomes following Intravenous or Intraperitoneal Administration, PHA. 26 (1983) 221-229.

[84] G. Lee, S. Han, I. Inocencio, E. Cao, J. Hong, A.R.J. Phillips, J. A. Windsor, C.J.H. Porter, N. L. Trevaskis, Lymphatic Uptake of Liposomes after Intraperitoneal Administration Primarily Occurs via the Diaphragmatic Lymphatics and is Dependent on Liposome Surface Properties, Mol. Pharmaceutics. 16 (2019) 4987-4999.

[85] Z. Xueying, L. Zhelong, S. Wenqi, Y. Guodong, X. Changyang, Y. Lijun, Delivery Efficacy Differences of Intravenous and Intraperitoneal Injection of Exosomes: Perspectives from Tracking Dye Labeled and MiRNA Encapsulated Exosomes, Current Drug Delivery. 17 (2020) 186-194.

[86] E. A. Greenfield, ed., Antibodies A Laboratory Manual, Second edition, Illustrated edition, Cold Spring Harbor Laboratory Press, Cold Spring Harbor, New York, 2013.

[87] H. Kim, N.C. Berens, N. E. Ochandarena, B. D. Philpot, Region and Cell Type Distribution of TCF4 in the Postnatal Mouse Brain, Frontiers in Neuroanatomy. 14 (2020) 42.

[88] M. Dell'Aringa, R. L. Reinhardt, Notch signaling represents an important checkpoint between follicular T-helper and canonical T-helper 2 cell fate, Mucosal Immunol. 11 (2018) 1079-1091.

[89] R. E. Mebius, G. Kraal, Structure and function of the spleen, Nat Rev Immunol. 5 (2005) 606-616.

[90] L. A. Medina, R. Klipper, W. T. Phillips, B. Goins, Pharmacokinetics and biodistribution of [11 11*n*]-avidin and [99mTc]-biotin-liposomes injected in the pleural space for the targeting of mediastinal nodes, Nuclear Medicine and Biology. 31 (2004) 41-51. doi.org/10.1016/SO969-8051(03)00122-7.

[91] K. Schwarz, M. Simons, J. Reiser, M. A. Saleem, C. Faul, W. Kriz, A. S. Shaw, L. B. Holzman, P. Mundel, Podocin, a raft-associated component of the glomerular slit diaphragm, interacts with CD2AP and nephrin, J Clin Invest. 108 (2001) 1621-1629.

[92] Polyclonal vs. monoclonal antibodies, (n.d.). (accessed Jul. 30, 2021).

[93] What is a polyclonal antibody?-Ximbio FAQ, (n.d.). (accessed Jul. 30, 2021).

[94] P. Towler, B. Staker, S. G. Prasad, S. Menon, J. Tang, T. Parsons, D. Ryan, M. Fisher, D. Williams, N. A. Dales, M. A. Patane, M. W. Pantoliano, ACE2 X-Ray Structures Reveal a Large Hinge-bending Motion Important for Inhibitor Binding and Catalysis*, Journal of Biological Chemistry. 279 (2004) 17996-18007.

[95] A. J. Turner, Chapter 25-ACE2 Cell Biology, Regulation, and Physiological Functions, in: T. Unger, U. M. Steckelings, R.A.S. dos Santos (Eds.), The Protective Arm of the Renin Angiotensin System (RAS), Academic Press, Boston, 2015: pp. 185-189.

[96] M. Donoghue, F. Hsieh, E. Baronas, K. Godbout, M. Gosselin, N. Stagliano, M. Donovan, B. Woolf, K. Robison, R. Jeyaseelan, R. E. Breitbart, S. Acton, A novel angiotensin-converting enzyme-related carboxypeptidase (ACE2) converts angiotensin I to angiotensin 1-9, Circ Res. 87 (2000) El-9.

[97] D. Harmer, M. Gilbert, R. Borman, K. L. Clark, Quantitative mRNA expression profiling of ACE 2, a novel homologue of angiotensin converting enzyme, FEBS Letters. 532 (2002) 107-110.

[98] F. Gembardt, A. Sterner-Kock, H. Imboden, M. Spalteholz, F. Reibitz, H.-P. Schultheiss, W.-E. Siems, T. Walther, Organ-specific distribution of ACE2 mRNA and correlating peptidase activity in rodents, Peptides. 26 (2005) 1270-1277.

[99] R. Munagala, F. Agil, J. Jeyabalan, R. C. Gupta, Bovine milk-derived exosomes for drug delivery, Cancer Letters. 371 (2016) 48-61.

[100] S. Kodidela, S. Ranjit, N. Sinha, C. McArthur, A. Kumar, S. Kumar, Cytokine profiling of exosomes derived from the plasma of HIV-infected alcohol drinkers and cigarette smokers, PLOS ONE. 13 (2018) e0201144.

[101] M. T. Abrams, M. L. Koser, J. Seitzer, S. C. Williams, M. A. DiPietro, W. Wang, A. W. Shaw, X. Mao, V. Jadhav, J. P. Davide, P. A. Burke, A. B. Sachs, S. M. Stirdivant, L. Sepp-Lorenzino, Evaluation of Efficacy, Biodistribution, and Inflammation for a Potent siRNA Nanoparticle: Effect of Dexamethasone Co-treatment, Molecular Therapy. 18 (2010) 171-180.

[102] Q. Pan, V. Ramakrishnaiah, S. Henry, S. Fouraschen, P. E. de Ruiter, J. Kwekkeboom, H. W. Tilanus, H.L.A. Janssen, L.J.W. van der Laan, Hepatic cell-to-cell transmission of small silencing RNA can extend the therapeutic reach of RNA interference (RNAi), Gut. 61 (2012) 1330-1339.

[103] H. Nie, X. Xie, D. Zhang, Y. Zhou, B. Li, F. Li, F. Li, Y. Cheng, H. Mei, H. Meng, L. Jia, Use of lung-specific exosomes for miRNA-126 delivery in non-small cell lung cancer, Nanoscale. 12 (2020) 877-887.

[104] C. Liu, C. Su, Design strategies and application progress of therapeutic exosomes, Theranostics. 9 (2019) 1015-1028.

[105] G. Liang, Y. Zhu, D.J. Ali, T. Tian, H. Xu, K. Si, B. Sun, B. Chen, Z. Xiao, Engineered exosomes for targeted co-delivery of miR-21 inhibitor and chemotherapeutics to reverse drug resistance in colon cancer, Journal of Nanobiotechnology. 18 (2020) 10.

[106] C. Meyer, J. Losacco, Z. Stickney, L. Li, G. Marriott, B. Lu, Pseudotyping exosomes for enhanced protein delivery in mammalian cells, IJN. 12 (2017) 3153-3170.

[107] S. Hsu, B. Yu, X. Wang, Y. Lu, C. R. Schmidt, R. J. Lee, L. J. Lee, S. T. Jacob, K. Ghoshal, Cationic lipid nanoparticles for therapeutic delivery of siRNA and miRNA to murine liver tumor, Nanomedicine: Nanotechnology, Biology and Medicine. 9 (2013) 1169-1180.

[108] Y. Akao, Y. Nakagawa, I. Hirata, A. Iio, T. Itoh, K. Kojima, R. Nakashima, Y. Kitade, T. Naoe, Role of anti-oncomirs miR-143 and -145 in human colorectal tumors, Cancer Gene Ther. 17 (2010) 398-408.

[109] Y. Wu, M. Crawford, B. Yu, Y. Mao, S. P. Nana-Sinkam, L. J. Lee, MicroRNA Delivery by Cationic Lipoplexes for Lung Cancer Therapy, Mol. Pharmaceutics. 8 (2011) 1381-1389.

[110] Y. Wu, M. Crawford, Y. Mao, R. J. Lee, I. C. Davis, T. S. Elton, L. J. Lee, S. P. Nana-Sinkam, Therapeutic Delivery of MicroRNA-29b by Cationic Lipoplexes for Lung Cancer, Molecular Therapy—Nucleic Acids. 2 (2013) e84.

[111] L. Jiang, H. Wang, S. Chen, Aptamer (AS1411)-Conjugated Liposome for Enhanced Therapeutic Efficacy of miRNA-29b in Ovarian Cancer, Journal of Nanoscience and Nanotechnology. 20 (2020) 2025-2031.

[112] Y. Chen, X. Zhu, X. Zhang, B. Liu, L. Huang, Nanoparticles Modified With Tumor-targeting scFv Deliver siRNA and miRNA for Cancer Therapy, Molecular Therapy. 18 (2010) 1650-1656.

[113] D. L. Iden, T. M. Allen, In vitro and in vivo comparison of immunoliposomes made by conventional coupling techniques with those made by a new post-insertion approach, Biochimica et Biophysica Acta (BBA)—Biomembranes. 1513 (2001) 207-216.

[114] C. Guo, Y. Chen, W. Gao, A. Chang, Y. Ye, W. Shen, Y. Luo, S. Yang, P. Sun, R. Xiang, N. Li, Liposomal Nanoparticles Carrying anti-IL6R Antibody to the Tumour Microenvironment Inhibit Metastasis in Two Molecular Subtypes of Breast Cancer Mouse Models, Theranostics. 7 (2017) 775-788.

[115] Optimization of post-insertion method to conjugate Doxil with anti-CD133 monoclonal antibodies: Investigating the specific binding and cytotoxicity to colorectal cancer cells in vitro—ScienceDirect, (n.d.). (accessed Sep. 14, 2021).

[116] R. W. Baker, B. T. Low, Membrane Separation*, in: Reference Module in Chemistry, Molecular Sciences and Chemical Engineering, Elsevier, 2015.

[117] M. Sack, J. Sigler, S. Frenzel, Chr. Eing, J. Arnold, Th. Michelberger, W. Frey, F. Attmann, L. Stukenbrock, G. Miller, Research on Industrial-Scale Electroporation Devices Fostering the Extraction of Substances from Biological Tissue, Food Eng. Rev. 2 (2010) 147-156.

[118] S. Kosuri, G. M. Church, Large-scale de novo DNA synthesis: technologies and applications, Nature Methods. 11 (2014) 499-507.

[119] J. F. Buyel, R. M. Twyman, R. Fischer, Very-Large-Scale Production of Monoclonal Antibodies in Plants, in: Process Scale Purification of Antibodies, John Wiley & Sons, Ltd, 2017: pp. 655-672.

[120] A. T. Reiner, K. W. Witwer, B.W.M. van Balkom, J. de Beer, C. Brodie, R. L. Corteling, S. Gabrielsson, M. Gimona, A. G. Ibrahim, D. de Kleijn, C. P. Lai, J. L6tvall, H. A. del Portillo, I.G. Reischl, M. Riazifar, C. Salomon, H. Tahara, W.S. Toh, M.H.M. Wauben, V.K. Yang, Y. Yang, R.W.Y. Yeo, H. Yin, B. Giebel, E. Rohde, S.K. Lim, Concise Review: Developing Best-Practice Models for the Therapeutic Use of Extracellular Vesicles, STEM CELLS Translational Medicine. 6 (2017) 1730-1739.

[121] B. Adriano, N. M. Cotto, N. Chauhan, M. Jaggi, S. C. Chauhan, M. M. Yallapu, Milk exosomes: Nature's abundant nanoplatform for theranostic applications, Bioactive Materials. 6 (2021) 2479-2490.

[122] B. Yu, R. J. Lee, L. J. Lee, Chapter 7-Microfluidic Methods for Production of Liposomes, in: Methods in Enzymology, Academic Press, 2009: pp. 129-141.

[123] C. Walsh, K. Ou, N. M. Belliveau, T. J. Leaver, A. W. Wild, J. Huft, P. J. Lin, S. Chen, A. K. Leung, J. B. Lee, C. L. Hansen, R. J. Taylor, E. C. Ramsay, P. R. Cullis, Microfluidic-based manufacture of siRNA-lipid nanoparticles for therapeutic applications, Methods Mol Biol. 1141 (2014) 109-120.

[124] C. Charoenviriyakul, Y. Takahashi, M. Nishikawa, Y. Takakura, Preservation of exosomes at room temperature using lyophilization, International Journal of Pharmaceutics. 553 (2018) 1-7.

[125] P. J. Stevens, R. J. Lee, Formulation kit for liposomal doxorubicin composed of lyophilized liposomes, Anticancer Res. 23 (2003) 439-442.

[126] Full article: Preparation and Characterization of Lyophilized Liposomes with Incorporated Quercetin, (n.d.). (accessed Sep. 14, 2021).

[127] M. Glavas-Dodov, E. Fredro-Kumbaradzi, K. Goracinova, M. Simonoska, S. Calis, S. Trajkovic-Jolevska, A. A. Hincal, The effects of lyophilization on the stability of liposomes containing 5-FU, International Journal of Pharmaceutics. 291 (2005) 79-86.

[128] T. Hernandez-Caselles, J. Villalain, J. C. G6mez-Fernandez, Stability of Liposomes on Long Term Storage, Journal of Pharmacy and Pharmacology. 42 (1990) 397-400.

[129] P. R. Matias-Garcia, R. Wilson, V. Mussack, E. Reischl, M. Waldenberger, C. Gieger, G. Anton, A. Peters, A. Kuehn-Steven, Impact of long-term storage and freeze-thawing on eight circulating microRNAs in plasma samples, PLOS ONE. 15 (2020) e0227648.

[130] Q. Ge, Y. Zhou, J. Lu, Y. Bai, X. Xie, Z. Lu, miRNA in Plasma Exosome is Stable under Different Storage Conditions, Molecules. 19 (2014) 1568-1575.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of making functionalized lipid vesicles comprising a lipid membrane, the method comprising mixing in the presence of detergent, lipid vesicles comprising one or more lipids with one or more types of lipid conjugates, each type of lipid conjugate comprising a lipid component and a functional element and dialyzing the mixture for an effective amount of time for the lipid conjugate(s) to insert into the lipid vesicles and form functionalized lipid vesicles.

2. The method of claim 1, wherein the lipid conjugate is formed by one or more of the steps of (i) mixing or otherwise suspending the lipid component, or a precursor thereof, in a solution comprising a concentration of detergent near the critical micelle concentration to form a suspension, (ii) dialyzing the suspension to remove excess detergent, and encourage formation of stable micelles in the suspension, (iii) adding, mixing, or otherwise contacting the suspension with the functional element, under conditions suitable for the functional element to conjugate, or otherwise link, to the lipid component to form the lipid conjugate.

3. The method of claim 2, wherein the detergent is of a type and amount suitable for stabilizing the hydrophobic regions of the lipid component, or precursor thereof, in a semi-aqueous solution.

4. The method of claim 3, wherein dialysis of the mixture removes the detergent.

5. The method of claim 4, wherein the detergent is n-dodecyl-β-D-maltoside (DDM).

6. The method of claim 1, wherein the lipid vesicles are naturally occurring.

7. The method of claim 6, wherein the lipid vesicle are isolated from cultured or uncultured tissue, cells, or fluid.

8. The method of claim 7, wherein the fluid is derived from, or conditioned by, cultured cells.

9. The method of claim 7, wherein the fluid is blood, plasma, lymph liquid, malignant pleural effusion, amniotic liquid, breast milk, semen, saliva or urine.

10. The method of claim 9, wherein the lipid vesicles are exosomes.

11. The method of claim 1, wherein the lipid vesicles are synthetic.

12. The method of claim 1, wherein the functional element is a small molecule, protein or polypeptide, carbohydrate, nucleic acid, or a combination thereof.

13. The method of claim 12, wherein the functional element is a targeting moiety that increases attachment, binding, or association of the functionalized lipid vesicle to a target cell(s), tissues(s), and/or microenvironment(s) relative to the lipid vesicle, optionally wherein the targeting moiety is an antibody.

14. The method of claim 13, wherein the targeting moiety targets cluster of differentiation 44 (CD44), cluster of differentiation 29 (CD29)/Integrin beta-1, ectonucleotide pyrophosphatase/phosphodiesterase 2 (ENPP2)/autotaxin, or intercellular adhesion molecule (I-CAM).

15. The method of claim 13, wherein the targeting moiety targets Asialoglycoprotein receptor 1 (ASGR1).

16. The method of claim 1, further comprising loading the lipid vesicles or functionalized lipid vesicles with an active agent.

17. The method of claim 16 wherein the active agent is a nucleic acid, optionally wherein the nucleic acid is a micro RNA (miRNA), and the loading of the active agent comprises electroporation.

18. The method of claim 17, wherein the loading comprises incubating the lipid vesicles or functionalized lipid vesicles for at least 30 minutes at ambient temperature (10-25° C.) followed by at least 30 minutes at 4° C.

19. A functionalized lipid vesicle formed according to the method of claim 1.

20. A method of treating a subject in need thereof comprising administering to the subject an effective amount of functionalized lipid vesicles formed according to the method of claim 1.

* * * * *